United States Patent
Iliev et al.

(10) Patent No.: US 11,712,436 B2
(45) Date of Patent: Aug. 1, 2023

(54) THERANOSTIC TEST FOR ANTIFUNGAL TREATMENT OF INFLAMMATORY DISEASES

(71) Applicant: Cornell University, Ithaca, NY (US)

(72) Inventors: Iliyan Iliev, New York, NY (US); Irina Leonardi, New York, NY (US)

(73) Assignee: Cornell University, Ithaca, NY (US)

( * ) Notice: Subject to any disclaimer, the term of this patent is extended or adjusted under 35 U.S.C. 154(b) by 293 days.

(21) Appl. No.: 16/955,718

(22) PCT Filed: Dec. 20, 2018

(86) PCT No.: PCT/US2018/066892
§ 371 (c)(1),
(2) Date: Jun. 18, 2020

(87) PCT Pub. No.: WO2019/126556
PCT Pub. Date: Jun. 27, 2019

(65) Prior Publication Data
US 2021/0069156 A1  Mar. 11, 2021

Related U.S. Application Data

(60) Provisional application No. 62/608,324, filed on Dec. 20, 2017.

(51) Int. Cl.
*A61K 31/4196* (2006.01)
*A61P 1/04* (2006.01)
*C12Q 1/6883* (2018.01)
*A61P 29/00* (2006.01)

(52) U.S. Cl.
CPC .......... *A61K 31/4196* (2013.01); *A61P 1/04* (2018.01); *A61P 29/00* (2018.01); *C12Q 1/6883* (2013.01); *C12Q 2600/106* (2013.01); *C12Q 2600/156* (2013.01)

(58) Field of Classification Search
CPC .............. A61K 31/343; A61K 31/4174; A61K 31/4196; A61K 31/7048; A61K 31/10; A61P 1/04; A61P 29/00; A61P 37/00; C12Q 1/6883; C12Q 2600/106; C12Q 2600/156
See application file for complete search history.

(56) References Cited

U.S. PATENT DOCUMENTS

2005/0049208 A1* 3/2005 Kaufmann .......... A61K 31/4178
514/397
2007/0110685 A1 5/2007 Auspitz et al.

OTHER PUBLICATIONS

Shah et al., Diabetes, publ. 2011, vol. 60, pp. 1512-1518 (Year: 2011).*
Gerard, R., et al, An immunological link between Candida albicans colonization and Crohn's disease, Critical Reviews in Microbiology, Jul. 15, 2013, vol. 41, No. 2, pp. 135-139.
Hager, C. et al, The mycobiome: Role in health and disease, and as a potential probiotic target in gastrointestinal disease, Digestive and Liver Disease, Oct. 4, 2017, vol. 49, No. 11, pp. 1171-1176.
Leonardi, I., et al, CX3CR1+ mononuclear phagocytes control immunity to intestinal fungi, Science, Jan. 12, 2018, vol. 359, No. 6372, pp. 232-236.
Break, T., et al, CX3CR1 Is Dispensable for Control of Mucosal Candida albicans Infections in Mice and Humans, Infection and Immunity, Dec. 29, 2014, vol. 83, No. 3, pp. 958-965.
Lionakis, M.S., et al., CX3CR1-dependent renal macrophage survival promotes Candida control and host survival, The Journal of Clinical Investigation, Nov. 1, 2013, vol. 123, No. 12, pp. 5035-5051.

* cited by examiner

*Primary Examiner* — Sarah Pihonak
(74) *Attorney, Agent, or Firm* — Hodgson Russ LLP

(57) ABSTRACT

Provided is a method to identify subjects with inflammatory diseases, such as inflammatory bowel disease, for their suitability for treatment with antifungal compounds. The method comprises identification of loss-of-function in the gene CX3CR1.

12 Claims, 49 Drawing Sheets

Specification includes a Sequence Listing.

F

G

A

*P. kudriavazevii*

*S. cerevisiae*

*A. amstelodami*

*A. versicolor*

F

G

H

A

B

THERANOSTIC TEST FOR ANTIFUNGAL TREATMENT OF INFLAMMATORY DISEASES

CROSS-REFERENCE TO RELATED APPLICATIONS

This applications claims priority to U.S. Provisional application no. 62/608,324, filed on Dec. 20, 2017, the disclosure of which is incorporated herein by reference.

GOVERNMENT FUNDING

This invention was made with Government support under Grant Number DK113136 awarded by the National Institute of Diabetes and Digestive and Kidney Diseases. The United States Government has certain rights in the invention.

BACKGROUND OF THE DISCLOSURE

Intestinal fungi are an important component of the microbiota, and recent studies have unveiled their potential in modulating host immune homeostasis and inflammatory disease. Nonetheless, the mechanisms governing immunity to gut mycobiota have been unknown.

Studies on the intestinal bacteria have demonstrated that alterations in the microbiota have a dramatic impact on host immunity and contribute to several diseases of inflammatory origin. Fungi are present in the mammalian intestine, yet little is known about their ability to influence immune homeostasis. Serum antibodies against *Saccharomyces cerevisiae* mannan (ASCA) are elevated in several inflammatory diseases including Crohn's Disease (CD) (Standaert-Vitse et al., *Gastroenterology* 130, 1764-1775 (2006), Mankai et al., *Endocr Res* 38, 98-104 (2013), Riente *J Rheumatol* 31, 920-924 (2004). Systemic ASCA can develop in response to intestinal fungi (Iliev et al., *Science* 336, 1314-1317 (2012), Standaert-Vitse et al., *Gastroenterology* 130, 1764-1775 (2006), providing a possible link between the gut mycobiota and host immunity. Despite these studies, the cell subsets that initiate and regulate mucosal immune responses to the mycobiota remain unknown, and therefore, treatments based upon specific dysfuction is still not available.

SUMMARY OF THE DISCLOSURE

In this disclosure, we have identified $CX3CR1^+$ mononuclear phagocytes (MNPs) as essential for the initiation of innate and adaptive immune responses to intestinal fungi. In studies, genetic ablation of $CX3CR1^+$ MNPs led to changes in the gut fungal communities and to severe colitis that was rescued by antifungal treatment A missense mutation in the gene encoding CX3CR1 led to impaired antifungal responses in people with inflammatory bowel disease.

In an aspect, the present disclosure provides methods to treat a subject with an inflammatory disease, comprising determining if the subject has a loss-of-function mutation in CX3CR1, administering an antifungal drug to the subject if the subject has a loss of function mutation in CX3CR1. The loss-of-function mutation may be detected using a technique that can detected a mutation. In the detection method, amplification techniques (e.g., PCR or qPCR and the like) may be used. In an example, the mutation detected in CX3CR1 is rs3732378 (SEQ ID NO:1). The subject may have an inflammatory bowel disease (IBD). For example, the subject may have Crohn's disease. In an embodiment, the subject may have alcoholic liver disease, spondyloarthritis, Graves' disease, or systemic lupus erythematosus. The method may further comprise measuring the level of ASCA antibodies in the subject, and administering an antifungal drug if the subject's antibody titer, such as, for example, IgA ASCA level is less than normal. For example, the method may further comprise measuring the level of ASCA antibodies in the subject, and administering an antifungal drug if the subject's IgA ASCA level is less than 20 EU/ml or if the subject's ASCA IgG level is less than 40 EU/mL.

This disclosure also provides methods further comprising measuring gut mycobiome diversity, and administering an antifungal agent if there is dysbiosis. Gut mycobiome dysbiosis is present if there is a Shannon diversity score less than 2, or if relative number of reads of *Candida* spp. or the increase of *Basidiomycota* in respect to the total number of fungal reads is present. The fungal dysbiosis may comprise an overgrowth of one or more *Candida* spp. or one or more *Basidiomycota* species.

In an aspect, this disclosure provides a method for determining the presence or absence of one or more loss-of-function mutations in CX3CR1 gene. In an embodiment, the loss-of-function mutation is one or more of rs3732378, rs3732379, and/or rs41535248.

In an embodiment, this disclosure provides a method of treating an inflammatory disease in a subject who has been identified as having a loss-of-function mutation in CX3CR1 gene by administering to the subject a composition comprising one or more anti-fungal agents. Examples of inflammatory disease include alcoholic liver disease, spondyloarthritis, Graves' disease, or systemic lupus erythematosus In an embodiment, this disclosure provides a method of treating an inflammatory bowel disease in a subject who has been identified as having a loss-of-function mutation in CX3CR1 gene by administering to the subject a composition comprising one or more anti-fungal agents. Examples include Crohn's disease and ulcerative colitis.

Examples of antifungal drug (also referred to herein as antifungal agents) include, but are not limited to, voriconazole, fluconazole, terbinafine, caspofungin, micafungin, anidulafungin, clotrimazole, isavuconazonium, itraconazole, flucytosine, griseofulvin, and posaconazole.

DETAILED DESCRIPTION OF THE DISCLOSURE

Figure 1:
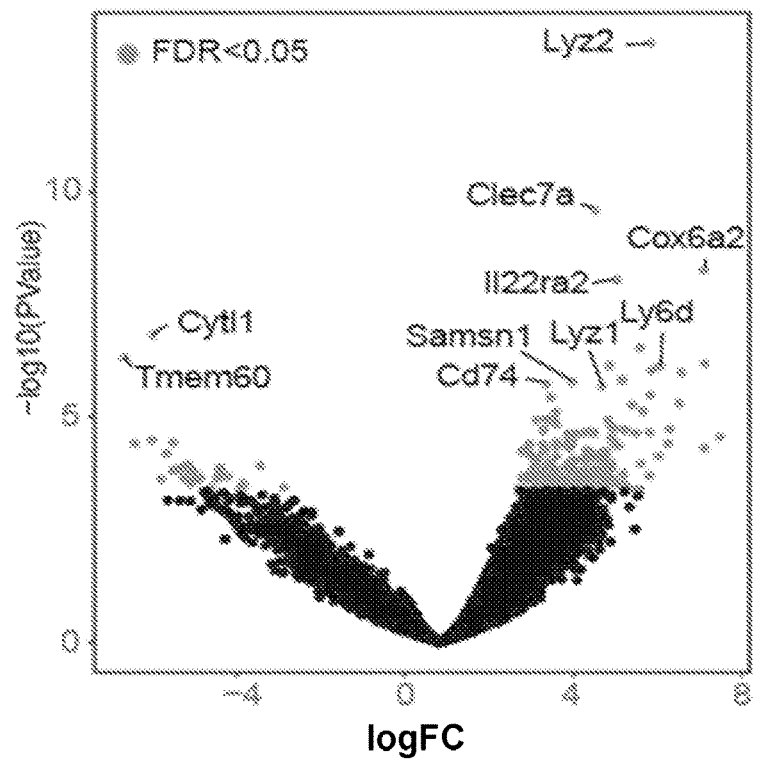
FIG. 1. CX3CR1 mononuclear cells express antifungal receptors and recognize fungi in the intestine. RNA sequencing (RNA-seq) analysis was performed comparing sorted $CD11b^+$ $CD103^+$ dendritic cells to $CX3CR1^+$ mononuclear phagocytes. P-value versus FC volcano plot comparing gene expression in the two cell subsets are shown as a volcano plot; grey dots indicate an FDR of <0.05. See also Table 1 (A). Logarithmic count per million (log(cpm)) normalization of genes involved in antigen presentation (left panel) or fungal recognition (right panel) are shown as a heat map (B). The expression of antifungal CLRs was confirmed by qRT-PCR (C). Representative flow cytometry histogram and quantification of dectin-1, dectin-2 (A) and Syk (C) expression among $CD11c^+$ $CD11b^-$ $CD103^+$; $CD11c^+$ $CD11b^+$ $CD103^+$ and $CD11c^+$ $CD11b^+$ $CX3CR1^+$ cells in C57BL6 mice (D). Representative confocal imaging (E) of the intake of RFP *C. albicans* (red) by $CX3CR1^+$ MNPs (green, $CX3CR1^+$, $DAPI^+$) and other cell types (blue, $CX3CR1^-$, $DAPI^+$) in the intestine. Bar graphs represent mean±SEM of individual mice (N=4-7), representative of at least two independent experiments.
Figure 1:
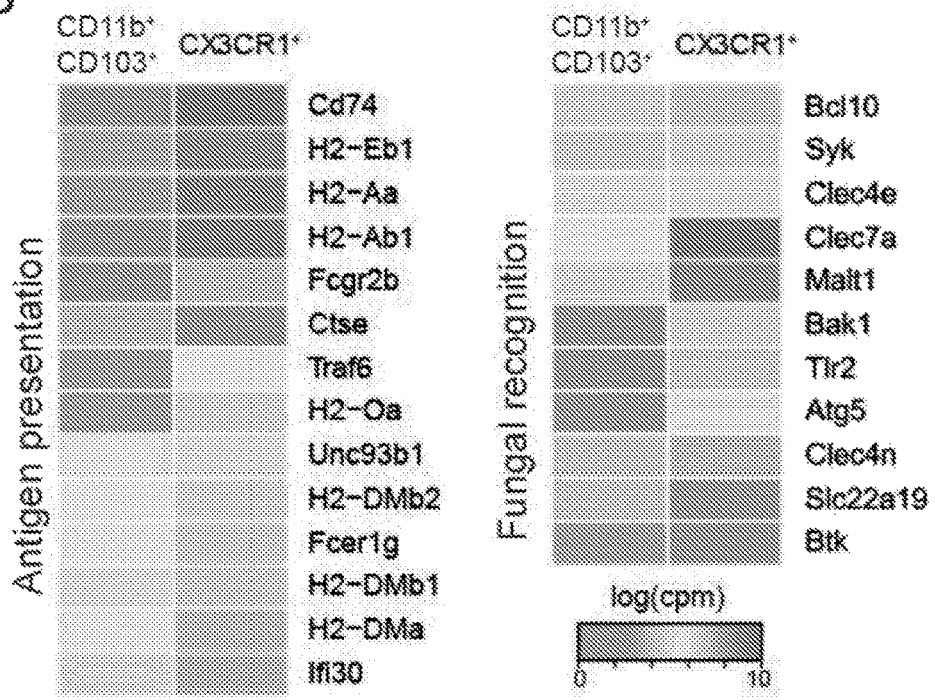
Figure 1:
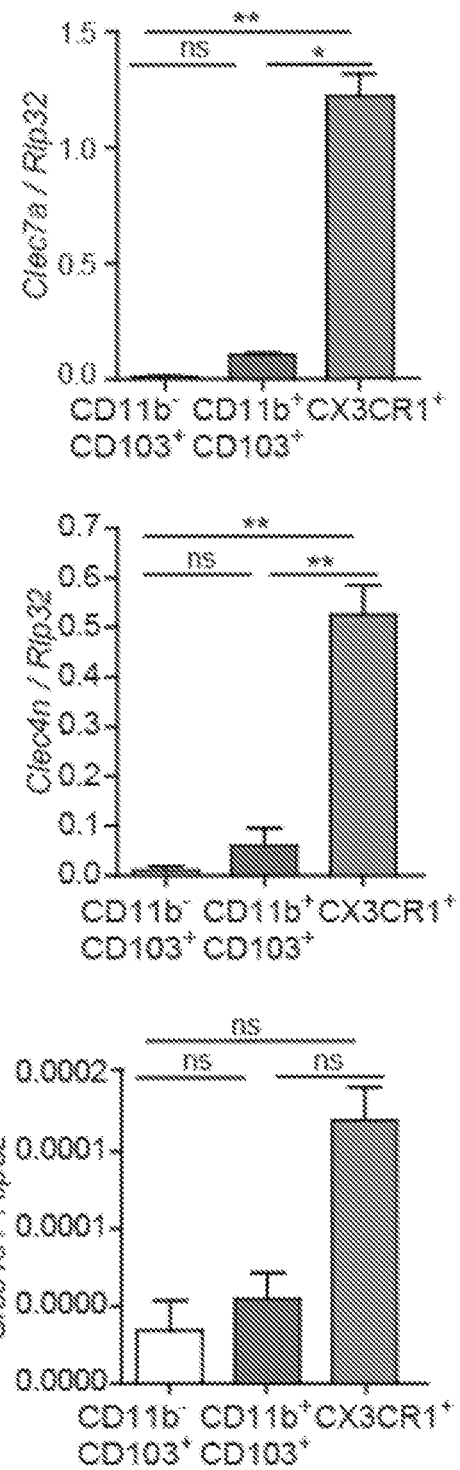
Figure 1:
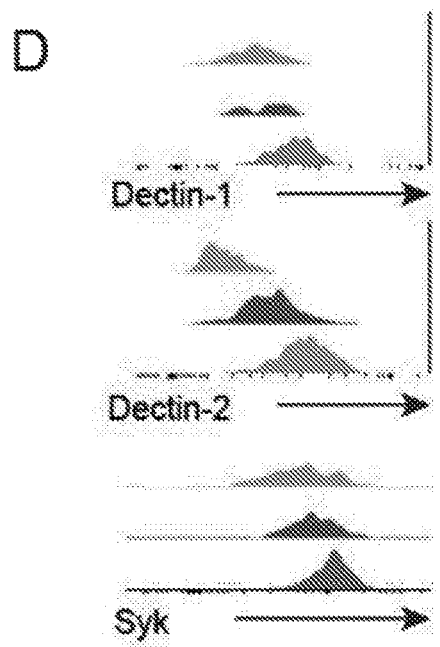
Figure 1:
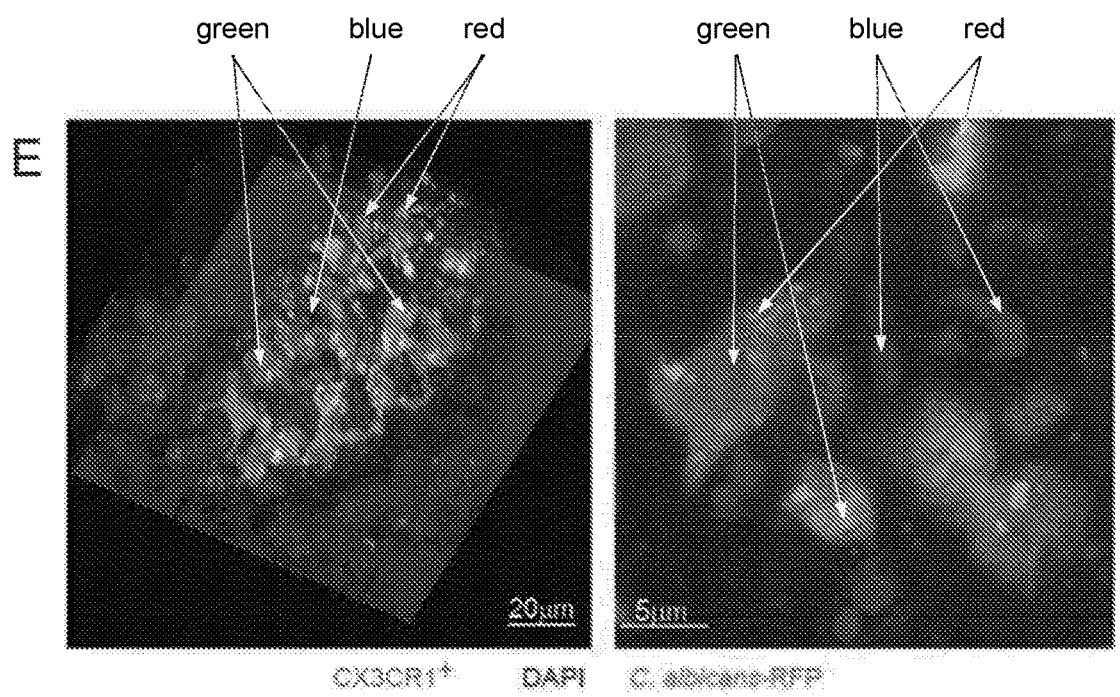

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Every numerical range given throughout this specification includes its upper and lower values, as well as every narrower numerical range that falls within it, as if such narrower numerical ranges were all expressly written herein.

All nucleotide sequences described herein, their RNA and DNA equivalents, and complimentary sequences are included in this disclosure. The disclosure includes all combinations of probes described herein, cells that are fixed to a substrate and which comprise probes that are directly and/or indirectly detectably labeled, and/or are hybridized to mRNA within fixed cells, and kits for performing assays as described herein. All polynucleotide and amino acid sequences associated with GenBank accession numbers (or other similar databases) described in this disclosure are incorporated herein by reference as those sequences are listed in the database as of the priority filing date of this application or patent.

The terms "a" or "an" are intended to include the singular as well as the plural of the particular item being reference. Any reference to a singular includes its plural and vice-versa.

The intestinal lamina propria (LP) is equipped with a cellular machinery to recognize and interact with the abundant microbiota. Several subsets of phagocytes respond to bacterial infections or to fluctuations in the commensal bacterial communities (Mowat et al., 2014, Nat Rev Immunol 14(10): 667-685). Among those, mononuclear phagocytes (MNPs), marked by the expression of the chemokine receptor CX3CR1 (CX3CR1+ MNPs), and subsets of dendritic cells (DCs) marked by the differential expression of the integrins CD11 b and CD103, have been shown to initiate immunity and prime Th17 responses to both commensal and pathogenic bacteria in the gut (Diehl et al., 2013, Nature 494(7435): 116-120; Persson et al., 2013, Immunity 38(5): 958-969; Schlitzer et al., 2013, Immunity 38(5): 970-983. Despite, their well described ability to respond to gut bacteria, their role in mucosal immunity to gut fungi has been unknown.

We identified a specific subset of gut resident phagocytes, namely the CX3CR1+ MNPs, which are able to recognize and respond to the gut mycobiota. CX3CR1+ MNPs can influence adaptive immune responses to gut fungi and control the mycobiota during experimental colitis. In humans, we found that a CX3CR1 polymorphism is strongly associated with a decrease of antifungal antibody responses in people with inflammatory bowel disease. CX3CR1 T280M is a common polymorphism (23.3% heterozygous and 4.4% homozygous (Brand et al., 2006, Am J Gastroenterol 101(1): 99-106) and has been previously associated with extra-intestinal inflammatory diseases (McDermott et al., 2001, Circ Res 89(5): 401-407; Maotti et al., 2001, Blood 97(7): 1925-1928. Gut mycobiota and CX3CR1-dependent immune responses can further contribute to extra-intestinal manifestations of inflammatory diseases. In support to this notion, antifungal antibodies are increased in patients with alcoholic liver disease, spondyloarthritis, Graves' disease and systemic lupus erythematosus (Riente et al., 2004, J Rheumatol 31(5): 920-924; Standaert-Vitse et al., 2006, Gastroenterology 130(6): 1764-1775, Mankai et al., 2013, Rheumatol Int 33(3): 665-669; Mankai et al., 2013, Endocr Res 38(2): 98-104). Altogether, our findings provide evidence for the influence of gut mycobiota on both local and systemic immunity which is mediated by the recognition of intestinal fungi by CX3CR1+ MNPs.

The method of the present disclosure comprises determining if a loss-of-function mutation is present in CX3CR1 in MNP phagocytes in a sample obtained from a subject, and if such a mutation is present, then administering an antifungal agent to the subject.

The subject may be any animal, including human and non-human animals. Non-human animals includes all vertebrates, e.g., mammals and non-mammals, such as non-human primates, sheep, dogs, cats, cows, horses, chickens, amphibians, and reptiles. The subject may also be livestock such as, cattle, swine, sheep, poultry, and horses, or pets, such as dogs and cats.

Subjects in need of the method of the present disclosure are those suffering from or at risk for an inflammatory disease, such as alcoholic liver disease, spondyloarthritis, Graves' disease and systemic lupus erythematosus, or an inflammatory bowel disease, such as Crohn's disease or ulcerative colitis. The subject is diagnosed with the condition by skilled artisans, such as a medical practitioner.

The methods of the invention described herein can be employed for subjects of any species, gender, age, ethnic population, or genotype. Accordingly, the term subject includes males and females, and it includes elderly, elderly-to-adult transition age subjects adults, adult-to-pre-adult transition age subjects, and pre-adults, including adolescents, children, and infants.

Examples of human ethnic populations include Caucasians, Asians, Hispanics, Africans, African Americans, Native Americans, Semites, and Pacific Islanders. The methods of the invention may be more appropriate for some ethnic populations such as Caucasians, especially northern European populations, as well as Asian populations.

The term subject also includes subjects of any genotype or phenotype as long as they are in need of the invention, as described above. In addition, the subject can have the genotype or phenotype for any hair color, eye color, skin color or any combination thereof.

The term subject includes a subject of any body height, body weight, or any organ or body part size or shape.

In the method of the present disclosure, a step is observing whether the genome of a subject contains at least one copy of a CX3CR1 allele having a loss-of-function genetic alteration. The determination whether or not there is a loss-of-function genetic alteration may be carried out by the medical practitioner who is examining the patient, or by a third party. For example, the determination can be carried out by a laboratory technician in a laboratory that specializes in identifying genetic alterations. The laboratory then informs the medical practitioner of the results by, for example, providing the medical practitioner with a written or oral report. In such a case, the medical practitioner observes whether the genome of the patient contains at least one copy of the gene name CX3CR1 allele having a genetic alteration by reading the report.

The genome of a patient generally contains two CX3CR1 alleles. An allele, as used herein, is any of one or more alternative forms of a gene. In an organism, two alleles of a given gene occupy corresponding loci on a pair of homologous chromosomes. For example, two alleles of a CX3CR1 gene occupy corresponding loci on chromosome 3.

The term "loss-of-function genetic alteration," as used herein, refers to any changes in one or more of the nucleic acid molecules in the nucleotide coding sequence of wild-type CX3CR1 that leads to a change in the amino acid sequence of wild-type CX3CR1 which renders the protein less functional than the wild-type protein. Examples of genetic alterations include one or more nucleotide additions, deletions, substitutions, etc., and combinations thereof. The genetic variation may, or may not, result in a frame shift.

Accordingly, the genetic alteration can occur at any nucleotide position(s) in the nucleotide sequence of CX3CR1. For example, the genetic alteration can occur at the beginning, middle or end of the nucleotide sequence.

Nucleotide additions and deletions refer to the addition and deletion, respectively, of one or more nucleotides in the nucleotide sequence of wild-type CX3CR1. If more than one nucleotide is added or deleted, the additions and deletions can be contiguous or non-contiguous. Any nucleotide (A, T, C, G), and any combination thereof, can be added or deleted. Additions and deletions may result in a frame shift, or may not result in a frame shift.

A nucleotide substitution refers to the replacement of a nucleotide with a different nucleotide. An example of a substitution is a single nucleotide polymorphism.

A single nucleotide addition, deletion, or substitution within the genome of a person is a genetic alteration, which is herein referred to as a single nucleotide polymorphism (SNP). More specifically, a SNP may be a single base insertion or deletion variant. A SNP substitution can be considered a transition or a transversion. A transition is the replacement of one purine nucleotide by another purine nucleotide, or one pyrimidine by another pyrimidine. A transversion is the replacement of a purine by a pyrimidine, or vice versa.

The standard nomenclature for representing a SNP by those skilled in the art is by a reference SNP number (rs #).

In an embodiment, the loss of function genetic alteration is a SNP in which the cytosine nucleotide at position 39265765 of wild-type CX3CR1 (GenBank no. NG 016362) in the Genome Reference Consortium Human genome build 38.1/141 (GRCh38) is substituted with the nucleotide thymine, and the resulting protein has an isoleucine at position 249 instead of a valine (V249I). The reference SNP number is rs3732379 (SEQ ID NO:2).

In an embodiment, the loss of function genetic alteration is a SNP in which the guanine nucleotide at position 39265671 of wild-type CX3CR1 in GRCh38 is substituted with the nucleotide adenine, and the resulting protein has a methionine at position 280 instead of a threonine (T280M). The reference SNP number is rs3732378 (SEQ ID NO:1). rs3732379 and rs3732378 are strongly linked.

In an embodiment, the loss of function genetic alteration is a SNP in which the guanine nucleotide at position 39266471 of wild-type CX3CR1 in GRCh38 is substituted with the nucleotide thymine and the resulting protein has an aspartate at position 13 instead of a glutamate (E13D). The reference SNP number is rs41535248 (SEQ ID NO:3).

The sequences of rs3732378, rs3732379 and rs41535248 are provided below.

```
rs3732378-
                                            (SEQ ID NO: 1)
CAGGCAACAATGGCTAAATGCAACCATCTCAGTCACACTGAGGGCCAGCCT rs3732379-
                                            (SEQ ID NO: 2)
TTAAGCGTCTCCAGGAAAATCATAATGTTGTAGGGTGTCCAGAAGAGGAAA rs41535248-
                                            (SEQ ID NO: 3)
CTGAATCAGTGACAGAAAACTTTGATTACGATGATTTGGCTGAGGCCTGTT
```

The nucleotide at the underlined position in SEQ ID NO: 1 in the wild type sequence is G. The nucleotide at the underlined position in SEQ ID NO: 2 in the wild type sequence is C. The nucleotide at the underlined position in SEQ ID NO: 3 in the wild type sequence is G.

In yet a further embodiment, the loss-of-function genetic alteration can be a combination of any of the SNPs described above.

A genetic alteration may occur within one copy or both copies of a CX3CR1 allele. A subject's homologous chromosomes may comprise identical alleles of the CX3CR1 gene at corresponding loci, in which case, the subject's CX3CR1 genotype is homozygous for the CX3CR1 gene. Alternatively, a subject's homologous chromosomes may not comprise identical alleles of the CX3CR1 gene at corresponding loci, in which case, the subject's CX3CR1 genotype is heterozygous for the CX3CR1 gene.

The subject's CX3CR1 genotype can be homozygous or heterozygous for any genetic alteration, such as those mentioned above. For example, a patient may be homozygous or heterozygous for any SNP. In an embodiment, the CX3CR1 genotype is homozygous for rs3732378. In an embodiment, the CX3CR1 genotype is heterozygous for rs3732378.

The determination of an allele having a genetic alteration can be made by any method known to those skilled in the art.

Primers for PCR amplification of T280M and V249I and other variants are known in the art. For example one set of V249I primers is (249_V: CTTCTGGACACCCTACAACG (SEQ ID NO:4); 249_I:CCTCTTCTGGACACCCTACAACA (SEQ ID NO:5); 249rev: GAGCTTAAGYGTCTCCAGGAAAATCAT) (SEQ ID NO:6) and a T280M primer set is (280_T: GGCCCTCAGTGTGACTGAGAC (SEQ ID NO:7); 280_M: GGCCCTCAGTGTGACTGAGAT (SEQ ID NO:8); 280_rev: GAGAGGATTCAGGCAACAATGGCTA) (SEQ ID NO:9). (Lopez-Lopez A, et al 2014)

Other suitable methods are provided in this disclosure including the Examples.

In another embodiment, the determination of a genetic alteration comprises observing expression of a CX3CR1 protein containing a loss of function amino acid alteration. Examples of amino acid alterations include one or more amino acid additions, deletions, substitutions, etc. and combinations thereof, e.g. any of the amino acid alterations caused by the genetic alterations described above.

An amino acid substitution that changes a codon coding for one amino acid to a codon coding for a different amino acid is referred to as a non-synonymous codon change, or missense mutation. One type of non-synonymous codon change is a nonsense mutation, which results in the formation of a stop codon, thereby leading to premature termination of a polypeptide chain and a defective protein.

In one embodiment, the amino acid alteration V249I. In another embodiment the amino acid alteration is T280M. In another embodiment the amino acid alteration is E13D.

Expression of a CX3CR1 protein having an amino acid alteration can be determined by any method known to those skilled in the art. Suitable methods are provided in the disclosure including the Examples.

In an embodiment of the invention, a step in the method of the present invention is determining an altered level of antifungal antibodies in the serum of subjects with Crohn's disease, ulcerative colitis (UC), alcoholic liver disease, spondyloarthritis, Graves' disease, or systemic lupus erythematosus. In an embodiment, the antibodies decrease in UC and increase in all other listed diseases. In an embodiment, the antifungal antibodies are anti-*Saccharomyces cerevisiae* antibody (ASCA), and are measured with any kit or CLIA test known in the art, as are the reagents used and the methods to use them. (Sandborn W J et al 2001). A person with Crohn's will generally have an ASCA of 20 EU/ml for IgA ASCA and/or 40 EU/mL IgG ASCA (Sandborn W J et al 2001), so in the method of the invention, the person with ASCA or with other antifungal antibody levels lower than these thresholds is considered an individual with fungal susceptibility. Such a person will be suitable to treatment with antifungal agents.

The observation of a depressed level of antifungal antibodies can be made by any method known to those skilled in the art. Suitable methods are provided in this disclosure including the Examples.

In an embodiment of the invention, a step in the method of the present disclosure is observing gut mycobiome dysbiosis in subjects.

Gut mycobiome dysbiosis can be measured by quantifying the prevalence of the various types of fungi present in the gut, directly or through a fecal sample, using methods known in the art for quantifying gut microbiomes. (Iliev and Leonardi 2017) For example, internal transcribed spacer (ITS)-1 based barcoding may be used. (Botschuijver S et al 2017)

In an embodiment, gut mycobiome dysbiosis is determined using the Shannon diversity score. Healthy people have a Shannon diversity score for the gut mycobiome of roughly between 2 and 3, or around 2, and people with inflammatory bowel disease with a have a Shannon diversity score lower than this.

In an embodiment, gut mycobiome dysbiosis can be determined by the relative number of reads of *Candida* spp. or the increase of Basidiomycota in respect to the total number of fungal reads. In healthy people, the presence of *Candida* spp is around 50% of total reads and in people with inflammatory bowel disease, the total will be higher. (Botschuijver S et al 2017)

The observation of a depressed level of antifungal antibodies can be made by any method known to those skilled in the art. Suitable methods are provided in the in this disclosure including the Examples.

To determine whether the genome of a patient contains at least one copy of the CX3CR1 allele containing a genetic alteration, a biological sample containing the patient's DNA can be obtained. Examples of such samples include blood, salvia, sweat, urine, any biological fluid, and epithelial cells. In general, the biological sample may be any biological material that contains DNA or RNA of the subject, such as a nucleated cell source. Non-limiting examples of cell sources include hair, skin, nucleated blood cells, buccal cells, any cells present in tissue obtained by biopsy or any other cell collection method. DNA may be extracted from the biologic sample such as the cell source or body fluid using any of the methods that are known in the art. In an embodiment, the cell source may be phagocytes, such as mononuclear phagocytes (HNPs).

The sample can be obtained by any method known to those in the art. Suitable methods include, for example, venous puncture of a vein to obtain a blood sample and cheek cell scraping to obtain a buccal sample.

DNA can be isolated from the sample by any method known to those in the art. For example, commercial kits, such as the QIAGEN System (QIAmp DNA Blood Midi Kit, Hilder, Germany) can be used to isolate DNA.

The DNA is optionally amplified by methods known in the art. One suitable method is the polymerase chain reaction (PCR) method described by Saiki et al., *Science* 239:487 (1988), U.S. Pat. No. 4,683,195 and Sambrook et al. (Eds.), Molecular Cloning, Third Edition, Cold Spring Harbor Laboratory Press, Cold Spring Harbor, New York (2001). For example, oligonucleotide primers complementary to a nucleotide sequence flanking and/or present at the site of the genetic alteration of the allele can be used to amplify the allele.

The isolated DNA can be used to determine whether an allele containing a genetic alteration is present in the sample. The presence of an allele containing a genetic alteration can be determined by any method known to those skilled in the art. One method is to sequence the isolated DNA and compare the sequence to that of wild-type CX3CR1.

Alternative methods include, for example, use of nucleic acid probes and polymerase chain reaction (PCR). Methods for making and using nucleic acid probes are well documented in the art. For example, see Keller G H and Manak M M, *DNA Probes*, 2$^{nd}$ ed., Macmillan Publishers Ltd., England (1991) and Hames B D and Higgins S J, eds., Gene Probes I and Gene Probes II, IRL Press, Oxford (1995).

Genotyping (e.g., SNP genotyping) or sequencing may involve techniques that including allele specific oligonucleotide hybridization, size analysis, sequencing, hybridization, 5' nuclease digestion, single-stranded conformation polymorphism analysis, allele specific hybridization, primer specific extension, and oligonucleotide ligation assays and the like.

As an example, the sequence of the extracted nucleic acid of the subject may be determined by any means known in the art, including but not limited to direct sequencing, hybridization with allele-specific oligonucleotides, allele-specific PCR, ligase-PCR, HOT cleavage, denaturing gradient gel electrophoresis (DDGE), and single-stranded conformational polymorphism (SSCP) analysis. Direct sequencing may be carried out by any method, such as, for example, chemical sequencing, using the Maxam-Gilbert method, by enzymatic sequencing, using the Sanger method; mass spectrometry sequencing; and sequencing using a chip-based technology. For example, DNA from an individual can be subjected to amplification by polymerase chain reaction (PCR) using specific amplification primers.

Restriction fragment length polymorphism (RFLP) analysis can be used for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press. Inc. (1990)). RFLP refers to any method for distinguishing genetic polymorphisms using a restriction enzyme, which is an endonuclease that catalyzes the degradation of nucleic acid and recognizes a specific base sequence, generally a palindrome or inverted repeat.

Allele-specific oligonucleotide hybridization can be used to detect an allele. Allele-specific oligonucleotide hybridization is based on the use of a labeled oligonucleotide probe having a sequence perfectly complementary, for example, to the sequence encompassing the allele. Under appropriate conditions, the allele-specific probe hybridizes to a nucleic acid containing the allele but not to other alleles, which have one or more nucleotide mismatches as compared to the probe. If desired, a second allele-specific oligonucleotide probe that matches an alternate allele also can be used. Further, allele-specific oligonucleotide amplification can be used to selectively amplify the particular allele by using an allele-specific oligonucleotide primer that is complementary to the nucleotide sequence of the particular allele.

A heteroduplex mobility assay (HMA) can be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

Single strand conformational, polymorphism (SSCP) can be used to detect the presence or absence of a SNP and/or a haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) can be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other methods for determining the presence or absence of a SNP and/or a haplotype include automated sequencing and RNAase mismatch techniques (Winter et al., Proc. Natl. Acad. Sci. 82:7575-7579 (1985)).

One skilled in the art will recognize many methods and materials similar or equivalent to those described herein, which could be used in the practice of the present disclosure. Indeed, the present disclosure is not limited to the methods and materials described herein.

To observe whether the patient expresses a CX3CR1 protein containing an amino acid alteration, a sample containing protein can be obtained. The sample can be any sample which contains protein. Examples of such samples include blood, skin, or a gut biopsy sample. The sample can be obtained by any method known to those in the art.

Protein can be isolated from the sample by any method known to those in the art. For example, commercial kits, such as the Mono Q ion exchange chromatography (Amersham Biosciences, Piscataway, N.J.) can be used to isolate the protein.

The protein can be used, for example, to generate antibodies. The antibody may be polyclonal or monoclonal. Polyclonal antibodies can be isolated from mammals that have been inoculated with the protein in accordance with methods known in the art.

Briefly, polyclonal antibodies may be produced by injecting a host mammal, such as a rabbit, mouse, rat, or goat, with the protein or fragment thereof capable of producing antibodies that distinguish between proteins containing amino acid alterations and wild-type protein. The peptide or peptide fragment injected may contain the wild-type sequence or the sequence containing the amino acid alteration. Sera from the mammal are extracted and screened to obtain polyclonal antibodies that are specific to the peptide or peptide fragment.

The antibodies are preferably monoclonal. Monoclonal antibodies may be produced by methods known in the art. These methods include the immunological method described by Kohler and Milstein in Nature 256, 495-497 (1975) and by Campbell in "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985); as well as the recombinant DNA method described by Huse et al. in Science 246, 1275-1281 (1989).

In order to produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein in Nature 256, 495-497 (1975). See also Campbell, "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985). In order to be useful, a peptide fragment must contain sufficient amino acid residues to define the epitope of the molecule being detected (e.g., distinguish between wild-type protein and proteins containing amino acid alterations).

The antibodies can, for example, be used to observe the presence of CX3CR1 proteins containing amino acid alterations. Suitable methods include, for example, a western blot and an ELISA assay.

In a subject with an inflammatory disease, the presence of a CX3CR1 allele is correlated with susceptibility to treatment with an antifungal compound. In an embodiment, a depressed level of antifungal antibodies in a person with Crohn's disease, alcoholic liver disease, spondyloarthritis, Graves' disease, or systemic lupus erythematosus, is correlated with susceptibility to treatment with an antifungal compound. In an embodiment, fungal dysbiosis in the gut of a person with an inflammatory disease, including an inflammatory bowel disease, is correlated with susceptibility to treatment with an antifungal compound.

A subject who is susceptible to treatment refers to a subject who will receive a clinically beneficial effect in response to the treatment. Such a subject may also be referred to as being suitable for treatment with the particular modality.

An effect that is clinically beneficial refers to an effect that yields some degree of benefit to at least some part of a patient population following treatment. For example, an effect that is clinically beneficial includes prolongation of the life span of the patient having the condition, inhibition of the progression of the condition, reduction in the rate of disease progression in the patient, remission or regression of the disease in the patient, or improvement in the quality of life of a patient having the condition.

Any method known to those of ordinary skill in the art can be used to determine whether the treatment has a clinically beneficial effect on a patient's condition. For example, a rating scale can be utilized to score the severity. The patient can then be monitored to determine the effect of the treatment over time.

Antifungal drugs are drugs that treat or prevent infections by fungal organisms. Approved antifungals drugs include the classes of polyenes, flucytosine, azoles and echinocandins, and include specific compounds voriconazole, fluconazole, terbinafine, caspofungin, natamycin, amphotericine, 5-FC, micafungin, anidulafungin, clotrimazole, isavuconazonium, itraconazole, flucytosine, griseofulvin, and posaconazole, APX001, AR-12, ASP2397, Efungumab, F901318, MGCD290, and T-2307. (Perfect J R 2017), efmaconazole, tavaborole, luliconazole, terbinafine, auric losene, E-1224, VT-1161, NDV-3, NDV-3A, SQ-109, MGCD-290, ME-1111, LACTIN-V, and combinations thereof. The anti-fungal agents include the salts thereof. In a preferred embodiment the antifungal drug can treat outgrowth by fungal species found in the human gut, including *Aspergillus* sp, *Candida* sp, *Cladosporium* sp, *Cryptococcus* sp, *Fusarium* sp, *Penicillium* sp, *Pneumocystis* sp, *Mucor* sp, *Malasezia* sp. or *Saccharomyces* sp.

The anti-fungal agents can be used at dosages known in the art. For example, in general a dosage of 0.1 microgram to 1 gram per kg may be used. Non-limiting examples of dosages and routes of administration of antifungal agents include: Amphotericin B (iv) up 0.5 to 1.0 mg/kg daily; Andidulafungin (iv) 100-200 mg on day 1 followed by 50-100 mg daily; voriconazole (iv/po) 6 mg/kg on 12 h and 24 h followed by 4 mg/kg IV q12 hr or 200 mg; fluconazole (po) 100 to 400 mg daily; terbinafine (po) 250 mg once a day; caspofungin (iv) 50-70 mg on the first day of treatment followed by 50 or 100 mg daily; micafungin (iv) 50 mg daily (prophylaxis). Or 100-150 mg daily for therapy; clotrimazole (vaginal tablet) 100 mg/day or 500 mg single dose; isavuconazonium (iv/po) 186-372 mg isavuconazonium sulfate (equivalent to 100-200 mg isavuconazole) every 8 hours for 2 days, then 372 mg daily; itraconazole (po) 100-400 mg daily; flucytosine (po) 50-150 mg/kg daily in divided doses (usually every six hours); griseofulvin (po) 250-1000 mg daily; posaconazole (po) po: 100-300 mg daily; iv: 300 mg on Day 1, then 300 mg IV qDay; ketoconazole (po) 200-400 mg daily.

The anti-fungal agents can be administered in a therapeutically effective amount. The term "therapeutically effective amount" as used herein refers to an amount of an agent sufficient to achieve, in a single or multiple doses, the intended purpose of treatment. Treatment does not have to lead to complete cure, although it may. Treatment can mean alleviation of one or more of the symptoms or markers of the indication. The exact amount desired or required will vary depending on the particular compound or composition used, its mode of administration, patient specifics and the like.

Appropriate effective amount can be determined by one of ordinary skill in the art informed by the instant disclosure using only routine experimentation. Within the meaning of the disclosure, "treatment" also includes relapse, or prophylaxis as well as the alleviation of acute or chronic signs, symptoms and/or malfunctions associated with the indication. Treatment can be orientated symptomatically, for example, to suppress symptoms. It can be effected over a short period, over a medium term, or can be a long-term treatment, such as, for example within the context of a maintenance therapy.

The anti-fungal agents can be administered in a pharmaceutical carrier as pharmaceutical compositions. The pharmaceutical compositions may be in the form of solutions, suspensions, emulsions, and solid injectable compositions that are dissolved or suspended in a solvent immediately before use. The injections may be prepared by dissolving, suspending or emulsifying one or more of the active ingredients in a diluent. Examples of diluents are distilled water for injection, physiological saline, physiologic buffer, vegetable oil, alcohol, and a combination thereof. Further, the compositions may contain stabilizers, solubilizers, suspending agents, emulsifiers, soothing agents, buffers, preservatives, etc. The pharmaceutical compositions may be formulated into a sterile solid or powdered preparation, for example, by freeze-drying, and may be used after sterilized or dissolved in sterile injectable water or other sterile diluent(s) immediately before use. The compositions can include one or more standard pharmaceutically acceptable carriers. Some examples herein of pharmaceutically acceptable carriers can be found in: *Remington: The Science and Practice of Pharmacy* (2013) 22nd Edition, Pharmaceutical Press. Oral compositions may comprise additives such as excipients carriers. Such additives can be liquids, such as water and oils, saline, glucose or the like, and auxiliary, stabilizing, thickening, or lubricating agents, wetting or emulsifying agents, or pH buffering agents, gelling or viscosity enhancing additives, detergents and solubilizing agents (e.g., TWEEN® 20, TWEEN® 80 also referred to as polysorbate 20 or 80), anti-oxidants (e.g., ascorbic acid, sodium metabisulfite), preservatives (e.g., Thimersol, benzyl alcohol), bulking substances (e.g., lactose, mannitol), flavoring agents, colors, and the like, depending upon the route of administration and the preparation desired. See "Remington's Pharmaceutical Science", 17th edition, 1985. Non-aqueous solvents or vehicles can be used such as propylene glycol, polyethylene glycol, vegetable oils, such as olive oil and corn oil, gelatin, and injectable organic esters such as ethyl oleate.

The formulations may be lyophilized and redissolved or resuspended just before use. The formulation may be sterilized by, for example, filtration through a bacteria retaining filter, by incorporating sterilizing agents into the compositions, by irradiating the compositions, or by heating the compositions. The pharmaceutical composition may be administered via any route that is appropriate, including but not limited to oral, parenteral, sublingual, transdermal, rectal, transmucosal, topical, via inhalation, via buccal administration, or combinations thereof. Parenteral administration includes, but is not limited to, intravenous, intraarterial, intraperitoneal, subcutaneous, intramuscular, intrathecal, and intraarticular. The agents(s) can also be administered in the form of an implant, which allows a slow release of the compound(s), as well as a slow controlled i.v. infusion. If administered orally, the anti-fungal agent compositions can be in the form of a tablet, capsule, pill, powder, paste, granules, elixir, solution, suspension, dispersion, gel, syrup or any other ingestible form.

The anti-fungal agent compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated.

In an embodiment, this disclosure provides a method to treat a subject with an inflammatory disease, comprising: a) determining if the subject has a loss of function mutation in CX3CR1; and b) administering an antifungal drug to the subject if the subject has a loss of function mutation in CX3CR1. The subject may have an inflammatory bowel disease, such as Crohn's disease or ulcerative colitis. Additionally, or alternatively, the subject may have alcoholic liver disease, spondyloarthritis, Graves' disease, or systemic lupus erythematosus. In an embodiment, the method may comprise or further comprise measuring the level of ASCA antibodies in the subject, and administering an antifungal drug if the IgA ASCA level is less than 20 EU/ml or if the ASCA IgG level is less than 40 EU/mL. In an embodiment, the method may comprise or further comprise measuring gut mycobiome diversity, and administering an antifungal agent if there is dysbiosis. In an embodiment, the gut mycobiome dysbiosis can be considered to be present if there is a Shannon diversity score less than 2, or if number of reads *Candida* spp are greater than 50% of total reads. The fungal dysbiosis may comprise an overgrowth of one or more *Candida* spp. or more Basidiomycota. The antifungal drug may be selected from the group including voriconazole, fluconazole, terbinafine, caspofungin, micafungin, anidulafungin, clotrimazole, isavuconazonium, itraconazole, flucytosine, griseofulvin, and posaconazole. The loss of function mutation can be detected using PCR amplification. In any of the previous embodiments, the loss of function mutation in CX3CR1 is rs3732378, rs3732379, and/or rs 41535248.

The following examples are intended to further illustrate the invention. The examples are not intended to be limiting.

EXAMPLES

The present description is further illustrated by the following examples, which should not be construed as limiting in any way. The contents of all cited references (including literature references, issued patents, published patent applications as cited throughout this application) are hereby expressly incorporated by reference.

Materials and Methods

Mice $Cx3cr1^{GFP/GFP}$, C57BL/6J, Cd11c-cre$^{+/+}$, Irf4$^{fl/fl}$, Cx3cr1$^{tm3(DTR)Litt/J}$ (Cx3cr1$^{DTR}$), Syk$^{fl/fl}$, Cx3cr1$^{tm2.1(cre/ERT2)Jung}$/J (Cx3cr1-cre/ERT2$^{+/+}$), Batf3$^{-/-}$, Thy1.1, and OVA-specific CD4$^+$ (OT-II) T-cell receptor-transgenic (H-2$^b$) mice were purchased from the Jackson Laboratories (Bar Harbor, Me.). The Cx3cr1$^{DTR}$ mice were subsequently bred to hemizygous Cd11c-cre$^{+/-}$ mice (expression of Cd11c-cre excises the foxed stop cassette, allowing for DTR expression in CD11c$^+$ cells) to allow for selective depletion of CD11c$^+$ CD11b$^+$ CX3CR1$^+$ MNPs upon administration of diphtheria toxin (DT). For depletion, mice generated through such breeding (Cd11c-cre$^{+/-}$ Cx3cr1$^{DTR}$ mice) and the respective littermate controls (Cd11c-cre$^{-/-}$ Cx3cr1$^{DTR}$) were injected for three consecutive days with 100 ng of DT i.p followed by maintenance injection every other day for the length of the experiments. Depleted mice were designated throughout the study as ΔCX3CR1 mice. Irf4$^{fl/fl}$ mice were bred to hemizygous Cd11c-cre$^{+/-}$ mice to allow for genetic ablation of CD11c$^+$ CD11b$^+$ CD103$^+$ dendritic cells (Cd11c-cre$^{+/-}$ Irf4$^{fl/fl}$ mice, designated throughout the study as ΔIrf4 mice) and the generation of littermate controls (Cd11c-cre$^{-/-}$ Irf4$^{fl/fl}$ mice). Syk$^{fl/fl}$ mice were bred to Cx3cr1-cre/ERT2$^{+/+}$ to allow for the selective depletion of Syk in CX3CR1 expressing cells upon administration of tamoxifen. For induction of Cre-ERT recombinase in Cx3cr1-cre/ERT2$^{+/-}$ mice, tamoxifen (TAM, Sigma) was dissolved in sunflower oil (Sigma) to a final concentration of 10 mg/ml, and 100 μl/mouse were injected i.p. every second day. Control littermates were injected with 100 μl sunflower oil. (Whitfield J et al 2015) GSK805 (EMD Milipore) was administered by oral gavage in corn oil at 10 mg/kg/day after being dissolved in DMSO. Control mice received DMSO alone in corn oil (Withers D R et al 2016). Mouse experiments were performed with at least four mice per group. Littermates were randomly assigned to experimental groups. Animals were used between 8 and 16 week of age. Males and females were used in approximately equal ratios. All animals were housed under specific pathogen-free conditions unless otherwise described at Weill Cornell Medicine and experiments were performed after prior approval by the Institutional Animal Care and Use Committee of Weill Cornell Medicine.

Fungal Strains and Generation of *Candida albicans* Strain Expressing OVA-II

*Candida albicans* (SC5314) and *Candida tropicalis* (ATCC 750) were obtained from the American Type Culture Collection (Manassas, Va.). *C. albicans* expressing red fluorescent protein (C.a-RFP) was generated as described. (Prieto A D et al 2014) *Rhodotorula mucilaginosa*, *Saccharomyces cerevisiae* (ATCC® MYA796™) and all *Candida* strains were cultured in aerobic conditions on Sabouraud Dextrose Broth (SDB; EMD Chemicals) at 37° C.

*Aspergillus amstelodami* (ATCC 46362) and *Aspergillus versicolor* (ATCC 52173) were cultured on SDB at 30° C. *Wallemia sebi* (FRR 1471, ATCC 42964) and *Cladosporium cladosporioides* (ATCC 38810) were grown on Sabouraud Dextrose Agar (SDA; EMD Chemicals) at RT.

Figure 11:
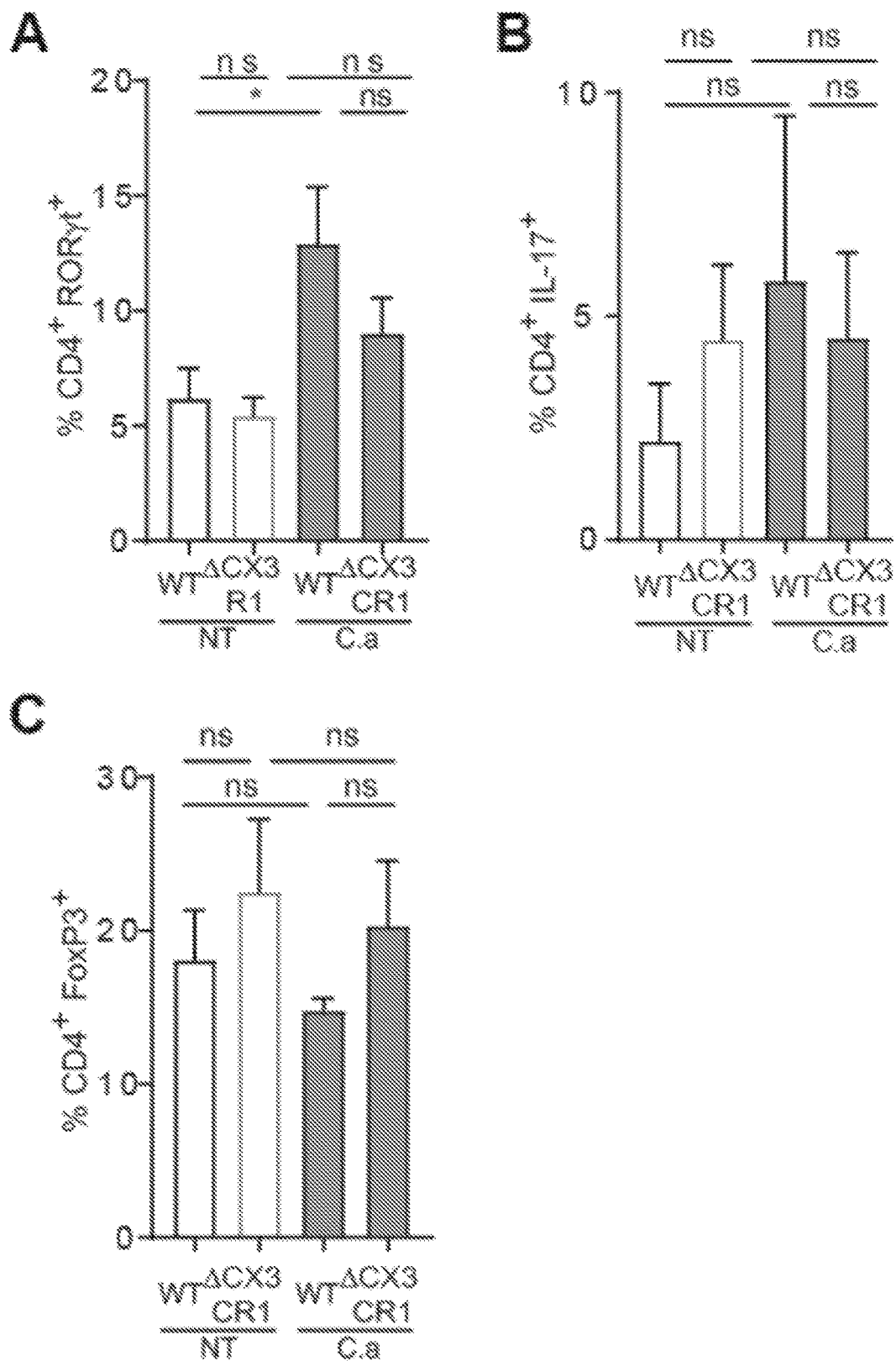
FIG. 11. Quantification of Th17 and Treg cells in the small intestine following *C. albicans* colonization. Quantification of RORγt+ Th17 (A), expression of IL-17 (B) by CD4+ T cells, FoxP3+ Treg cells (C) and in the small intestine of ΔCX3CR1 mice or wild type littermates. Data expressed as mean±SEM of individual mice, representative of two independent experiments.

For the generation of *Candida albicans* strain expressing GFP-OVA Class II Epitope fusion (C.a-OVA) standard molecular biology procedures were used. Briefly, plasmids were amplified in *Escherichia coli* DH5α strain growing in LB medium at 37° C. supplemented with ampicillin (100 mg/L). In order to generate strains expressing a GFP-OVA Class II Epitope fusion, we first constructed the OVA Class II Epitope (ISQAVHAAHAEINEAGR) (SEQ ID NO:10) using the primers o-OVAII-up (CCGGGGATCCGAATCTTTGAAAATTTCTCAAGCTGTTCACGCTGCTCACGCTGAAATTAACGAAGCTGGTAGAGAAGTTGTTGGTAGATCTGGCC) (SEQ ID NO:11) and o-OVAII-low (GCCAGATCTACCAACAACTTCTCTACCAGCTTCGTTAATTTCAGCGTGAGCAGCG TGAACAGCTTGAGAAATTTTCAAAGATTCGGATCCCCGG) (SEQ ID NO:12). PCR conditions: 94° C. for 1 minute, annealed at 55° C. for 5 min and then cooled to 4° C. The resulting small dsDNA was then digested with BamHI and BgJII and ligated to the yeast YEP352 episomal plasmid in the BamHI site. Plasmids carrying the class II epitope were selected by sequencing of the recombinant plasmids. The sequence of a *C. albicans* adapted GFP version (Morschhäuser 1998, *Mol. Gen. Genet.* 257312-420) was amplified using the primers GFPMo-up
(SEQ ID NO: 13)
(GGCCGGATCCGCGGCCGCATGAGTAAAGGAGAAGAACTTTTC)
and GFPMo-lo
(SEQ ID NO: 14)
(GGCCAGATCTTTTGTATAG TTCATCCATGCCATGTGT)

and inserted at the BamHI site of the previous construct to generate a C-terminal in frame GFP fusion. This construct (FIG. 11) was transferred to a SalI-BglII treated *C. albicans* vector pNIM1, a doxycycline inducible plasmid (Park et al., 2005, Eukaryotic. Cell 4, 1328-1342), by amplification using the primers JES13 (ATATAAATACTCGAGAAAGATGAGTAAGGGAGAAGAACTTTTC) (SEQ ID NO:15) and JES15 (ATTTAGATCTTTACATGATGCGGCCCTCCTGCAG) (SEQ ID NO:16) which introduced XhoI (SalI-compatible) and BglII sites. Finally, to make the system repressible (instead of inducible), an AvaI-KpnI piece of DNA from plasmid pNIM1R (kindly provided by Leah Cowen) replaced the AvaI-KpnI portion of the above construction. (Prieto A D et al 2014) The final plasmid, pNIM1R-GFP-OVAII was integrated at the *C. albicans* genome by digestion with SacII and KpnI, directing the integration at the ADHD region of wild type CAF2 strain. (Fonzi W A and Irwin M Y 1993) Strains were transformed by electroporation and transformants were selected as nourseothricine resistant clones on YPD medium supplemented with nourseothricine (100 mg/L). GFP and OVA Class II epitope expression were confirmed by flow cytometry and in in vivo assays as described below.

Imaging of In-Vivo and Ex-Vivo Fungal Intake by CX3CR1$^+$ Mononuclear Phagocytes For the imaging of in vivo uptake of *C. albicans*, Cx3cr1$^{GFP/GFP}$ were bred to C57BL/6J mice and the resulting heterozygous mice were fed for 3 consecutive days with 1·10$^8$ cfu/mouse C.a-RFP. Mice were sacrificed at day 4, colon were excised and gently flushed with cold PBS to remove feces. Colons were cut in segments, flushed twice with PBS, fixed and stained as described below. For the imaging of the ex-vivo uptake of fungi, colons from Cx3cr1$^{GFP/+}$ mice were excised and gently flushed with complete 37° C. RPMI media to remove the feces. Colon segments were closed with surgical threads and fungi (2·10$^7$/ml in complete RPMI) were injected. Colon sections were incubated in complete RPMI media for 2 h at 37° C. in an incubator at 5% CO$_2$. The colon sections were opened and gently flushed multiple time to remove the unbound fungi. All sections were subsequently fixed for 2 h in 2% PFA and incubated in 20% sucrose for 30' at RT. Sections were washed and blocked with 1 ml PBS, 2% BSA, followed by Hoechst or DAPI staining. Sections were finally washed 3× with water and mounted on glass chamber with Invitrogen Prolong Gold Antifade (ThermoFisher). Images were acquired on a Leica TCS SP confocal microscope with a Leica PL APO 100×/1.4 oil immersion lens.

Genotyping and Serological Analysis

Crohn's disease subjects were recruited by the IBD Center at Cedars-Sinai Medical Center following informed consent and IRB approval. DNA samples from human peripheral blood or B-lymphoblastoid cell line specimens were processed using an Illumina Infinium HumanExome+ BeadChip at Cedars-Sinai Medical Center and underwent rigorous quality control as previously described. (Li D et al 2016) Three missense SNPs passing quality control spanned the CX3CR1 gene (rs3732378, rs3732379, rs41535248) and a total of 503 Jewish CD subjects with complete data in genetic and serological markers were included in the genetic analysis. Serological evaluation was performed by ELISA as described below.

Detection of Anti-Fungal and Anti-Bacterial Antibodies in the Mouse and Human Serum The level of antibodies in the mouse or human serum that react with bacterial or fungal antigens was determined by a sandwich enzyme-linked immunosorbent assay (ELISA). Briefly, to obtain bacterial or fungal lysates for ELISA the overnight fungal or bacterial colonies were prepared through freeze and thawing disruption followed by 5 pulses of sonication. Such microbial lysates, *Saccharomyces cerevisiae* mannan (Sigma) or bacterial flagellin (Cbir-1) were used as the coating antigen in ELISA assay. ELISA detection of IgG was carried out as previously described. (Landers C J et al 2002) Samples were read at 405 nm on a microtiter plate reader (Menlo Park, Calif.).

Induction of DSS Colitis and Fungal Targeting with Fluconazole $Cx3cr1^{DTR}$ or littermate control mice were injected with DT for three consecutive days, prior to the induction of colitis with 3% (w/v) Dextran sulfate sodium (DSS, MP Biomedicals, LLC, Aurora, Ohio) in the drinking water. DT was then administered every second day and DSS water was removed at day 7. To target intestinal fungi, mice were given Fluconazole (0.5 mg/ml, Sigma) in the drinking water for the duration of the DSS treatment, starting 4 days prior the first DSS dose. In some experiments, mice were orally supplemented with *Candida tropicalis* or *Candida albicans* ($1 \cdot 10^8$ yeast/mouse/dose) every other day starting 2 days prior the DSS treatment. Control groups were orally gavaged with PBS at the same time points. Body weight and the presence of occult blood were assessed daily. Due to the increased intestinal disease susceptibility of $\Delta CX3CR1$ mice, all mice were sacrificed at days 7 to 10 from the first DSS dose. Colons and mLNs were removed for analysis. Distal colonic samples were fixed in 5% formalin and paraffin embedded. Slides were stained with hematoxylin and eosin (H&E) and imaged by light microscopy.

Colonization of Germ-Free Mice.

For microbiota transfer experiments, poop was collected and pooled from 5 $\Delta CX3CR1$ mice and from 5 control littermates after 1 week of treatment with DT. The pellets were resuspended in PBS and gavaged to 6 week-old germ-free mice. 16S rRNA qPCR of fecal content was used to confirm colonization. 2.5% DSS was administered in the drinking water and mice were sacrificed at day 7 as described above Assessment of *Candida* Induced Immune Response and Adoptive Transfer of CD4+ Thy 1.1+ OT-II Cells.

Cefoperazone (0.4 mg/ml; Sigma-Aldrich, St. Louis, Mo.) was provided to mice ad libitum in drinking water for the whole length of the experiments. Mice were fed with $5 \cdot 10^8$ *C. albicans* cells at day 1, 4 and 7 after the start of the cefoperazone water. Mice were sacrificed at day 10 and sampled as described below.

For the analysis of *Candida* specific T cell responses, Spleens and mesenteric lymph nodes of CD4$^+$ Thy1.1$^+$ OT-II donor mice were removed by dissection. Tissues were mashed onto a nylon screen, and the cells obtained were pooled, washed twice in Hanks' balanced salt solution (HBSS; Sigma-Aldrich), and resuspended at $1 \cdot 10^8$ cells/ml. Transgenic CD4+ Thy 1.1+ OT-II T cells were isolated by negative selection, using MagniSort™ Mouse CD4$^+$ T cell Enrichment Kit (eBioscience), according to the manufacturer's protocol. The purity of the CD4$^+$ cell population in the enriched fraction was >95%, as determined by flow cytometry analysis. CD4$^+$ isolated T cells were pooled and stained with carboxy-fluorescein diacetate succinimidyl ester (CFDA-SE; 7.5 µM Invitrogen) for 10 min at 37° C. $5 \cdot 10^6$ of CF SE-labeled T cells were transferred into recipient mice by retro-orbital injection. One day later, mice were fed with C.a-OVA as described above. Mice were terminated after 10 days. Successful adoptive transfer was confirmed by analysis of the CD4$^+$ Thy 1.1$^+$ population in the spleen, MLNs, colon and small intestines.

Isolation of Intestinal Mucosa, Small and Large Intestine Lamina Propria Cells

Intestinal LP cells were isolated as previously described (Matteoli G et al 2010) with some modifications. Briefly, colons were isolated, opened longitudinally, washed of fecal contents and then cut into 1 cm pieces. Intestinal pieces were transferred into HBSS medium (Sigma), supplemented with 5% fetal bovine serum (FBS) and 2 mM EDTA, and were shaken for 8 min at 37° C. The suspensions were filtered through a mesh and the filtrate containing epithelial cells fraction were washed twice with PBS and used further for RNA and DNA isolation. The remaining tissue was washed, cut in small pieces and subsequently incubated in digestion medium consisting of RPMI 1640, 5% FBS, 0.5 mg/ml collagenase type VIII (Sigma), 5 U/ml DNase (Roche Diagnostics), 100 IU/ml penicillin and 100 µg/ml streptomycin for 25 min at 37° C. by gentle shaking. The cell suspensions were filtered through a mesh and then centrifuged at 1700 rpm. The obtained cells were filtered through a 70 µm filter, washed twice and used as LP cells.

Antibodies and Flow Cytometry

Cell suspensions were prepared as described above, blocked with CD16/CD32 (Mouse BD Fc Block™, 2.4G2, BD Biosciences) and stained with antibodies against CD4 (GK1.5, eBioscience), CD45 (30-F11, Tonbo), CD90.1 (OX-7, Biolegend), CD11b (M1/70, Tonbo), CD11c (N418, Tonbo), CD64 (X54-5/7.1 FC, Biolegend), CD103 (2E7, eBioscience), MHC-II (I-A/I-E, M5/114.15.2, eBioscience), CX3CR1 (SA011F11, Biolegend) NK1.1 (eBioscience, PK136) Ly-6G (RB6-8C5, Tonbo), CD40 (HM40, eBioscience), CD86 (G1-1, Biolegend), Dectin-1 (2A11, Bio-Rad), Dectin-2 (KVa7-6E7, Miltenyi). For intracellular staining of transcription factors, cells were stained with surface markers, fixed permeabilized and stained with FoxP3 (FJK-16s, eBioscience) and RORγt (B2D, eBioscience). For intracellular cytokine and Syk detection, cells were incubated with 50 ng/ml phorbol 12-myristate 13-acetate (PMA; Sigma-Aldrich), 500 ng/ml ionomycin (Sigma-Aldrich) and 10 µg/ml Brefeldin A (BFA; Sigma-Aldrich) in complete RPMI media at 37° C. for 6 h. After surface staining with CD45, CD4, Thy 1.1 cells were fixed, permeabilized and staining was performed using PE-labeled anti-IL-17 mAb (eBio17B7; eBiosciences) or PE-labelled anti-Syk mAb (5F5; Biolegend) according to the manufacturer's instructions. Flow cytometry was performed using a LSRFortessa (BD Biosciences) and data were analyzed with FlowJo software (TreeStar Inc.).

DNA Isolation, Fungal and Bacterial rDNA Gene Quantitative Analysis

Fecal pellets were collected as indicated in the text, DNA for fungal and bacterial sequencing and validation RT-qPCR was isolated from 2-3 fecal pellets following lyticase treatment, bead beating, and processing using QIAmp DNA mini kit (Qiagen) as described. (Tang J et al 2015)

Microbiome Sequencing Analysis, Illumina Library Generation and Sequencing

Mouse fungal and bacterial microbiomes were sequenced using the Illumina MiSeq platforms. Fungal ITS1-2 regions and bacterial 16S regions were amplified by PCR using primers modified to include sample barcodes and sequencing adaptors:

```
Fungal primers:
ITS1F
                                        ((SEQ ID NO: 17)
CTTGGTCATTTAGAGGAAGTAA ITS2R
                                        (SEQ ID NO: 18)
GCTGCGTTCTTCATCGATGC Bacterial primers:
16S-27F
                                        (SEQ ID NO: 19)
AGAGTTTGATCMTGGCTCAG 16S-B5R357R
                                        (SEQ ID NO: 20)
CTGCTGCCTYCCGTA Forward overhang:
                                        (SEQ ID NO: 21)
5' TCGTCGGCAGCGTCAGATGTGTATAAGAGACAG-[locus-
specific sequence]

Reverse overhang:
                                        (SEQ ID NO: 22)
5' GTCTCGTGGGCTCGGAGATGTGTATAAGAGACAG-[locus-
specific sequence]
```

ITS1 amplicons were generated with 35 cycles, whereas 16S amplicons were generated with 25 cycles using Invitrogen AccuPrime PCR reagents (Carlsbad, Calif.). Amplicons were then used in the second PCR reaction, using Illumina Nextera XT v2 (San Diego, Calif.) barcoded primers to uniquely index each sample and 2×300 paired end sequencing was performed on the Illumina MiSeq (Illumina, Calif.). DNA was amplified using the following PCR protocol: Initial denaturation at 94° C. for 10 min, followed by 40 cycles of denaturation at 94° C. for 30 s, annealing at 55° C. for 30 s, and elongation at 72° C. for 2 min, followed by an elongation step at 72° C. for 30 min. All libraries were subjected to quality control using qPCR, DNA 1000 Bioanalyzer (Agilent), and Qubit (Life Technologies) to validate and quantitate library construction prior to preparing a Paired End flow cell.

Data Analysis

Raw FASTQ ITS1 sequencing data were filtered to enrich for high quality reads, removing the adapter sequence by cutadapt v1.4.1 or any reads that do not contain the proximal primer sequence. (Tang J et al 2015) Sequence reads were then quality-trimmed by truncating reads not having an average quality score of 20 (Q20) over a 3 base pair sliding window and removing reads shorter than 100 bp. (Tang J et al 2015) These high quality reads were then aligned to Targeted Host Fungi (THF) ITS1 database, using BLAST v2.2.22 and the pick_otus.py pipeline in the QIIME v1.6 wrapper with an identity percentage ≥97% for operational taxonomic unit (OTU) picking. (Altschul S F et al 1990) The THF database can be downloaded freely at: risccweb.csmc.edu/microbiome/thf/. The alignment results were then tabulated across all reads, using the accession identifier of the ITS reference sequences as surrogate OTUs and using a Perl script. (Tang J et al 2015) For Illumina bacterial analysis, because of the abundance of Illumina reads and higher overall sequence quality of the reads, we used the QIIME package with minimal customization. (Edgar RC 2010) Shannon diversity index (Shannon C E 1997) (H) was calculated at the OTUs levels as in Whitfield J et al 2015:

$$H^I = -\sum_{i=1}^{S} p_i \ln(p_i) \tag{1}$$

where $p_i$ is the proportional abundance of OTUs i.

Simpson Diversity Index (1-D) (Simpson E H 1949) was calculated as in Withers D R et al 2016

$$1 - D = 1 - \frac{\sum_{i=1}^{R} n_i(n_i - 1)}{N(N - 1)} \tag{2}$$

Where N=total number of individuals of all species, $n_i$=total number of individuals for each species i.

For the diversity analysis at the Phylum level, Shannon and Simpson diversity at the OTU level were calculated within the two major gut associated bacterial (Firmicutes and Becteroidetes) and Fungal (Ascomycota and Basidiomycota) Phyla.

| Real Time qPCR | | |
|---|---|---|
| Gene | Forward | Reverse |
| Eubacteria | ACTCCTACGGGAGGCAGCAGT (SEQ ID NO: 23) | ATTACCGCGGCTGCTGGC (SEQ ID NO: 24) |
| Fungi (18S) | ATT GGA GGG CAA GTC TGG TG (SEQ ID NO: 25) | CCG ATC CCT AGT CGG CAT AG (SEQ ID NO: 26) |
| Candida spp. | CCTGTTTGAGCGTCGTTT (SEQ ID NO: 27) | TCCTCCGCTTATTGATAT (SEQ ID NO: 28) |
| ITS5 | GGAAGTAAAAGTCGTAACAAGG (SEQ ID NO: 29) | |
| Ascomycota-specific-R | ITS5 | CGTTACTRRGGCAATCCCTGTTG3 (SEQ ID NO: 30) |
| Basidiomycota-specific-R | ITS5 | GCRCGGAARACGCTTCTC3 (SEQ ID NO: 31) |

Total fecal DNA isolated was isolated as described above. Real-time RT-PCR analyses were done on the Applied Biosystems 7500 Fast Real-Time PCR System with the SYBR Green PCR kit as instructed by the manufacturer (Applied Biosystems). Samples were analyzed for gene expression using the following primers:

Gene Expression Profiling by RNA-Seq and Bioinformatics Analyses

Live lineage negative (CD3, CD19, ab-TCR, SiglecF, Ly6G) $CD45^+$ $MHCII^+$ $CD11b^+$ $CD11c^+$ $CX3CR1^+$ and live lineage negative $CD45^+$ $MHCII^+$ $CD11b^+$ $CD11c^+$ $CD103^+$ cells were sorted from the colon of $Cx3cr1^{GFP/}+$ mice (FIG. 5A). cDNAs were prepared using the SMARTer Ultra Low Input RNA Kit for Sequencing version 3 following the user manual (Clontech Laboratories). Sequencing libraries were prepared using the Nextera XT DNA Library Prep Kit (Illumina). Cluster generation and 75-base pair single-end dual-indexed sequencing was performed on the Illumina NextSeq 500 system. The raw reads of RNA-seq were aligned to the mm10 genome using TopHat v1.0; packages Rsamtools v1.24.0, GenomicFeatures. (Trapnell C et al 2009) Genes where annotated to their Entrezid (package org.Mm.eg.db) leaving 24'451 total genes. Genes whose count per millions (CPM) was below 1 were removed from further processing, leaving 23707 total genes (Anders S et al 2013), Rawdata are deposited in GSE106594. The counts were analyzed for differential expression using EdgeR. For the analysis of genes involved in fungal recognition and antigen presentation expressed genes belonging to the following GO terms were selected: Fungal recognition: GO:0009620, GO:0071226, GO:0016046, GO:0002238, GO:0009610, GO:0001878; Antigen Presentation: GO:0042742.

Results

Figure 5:
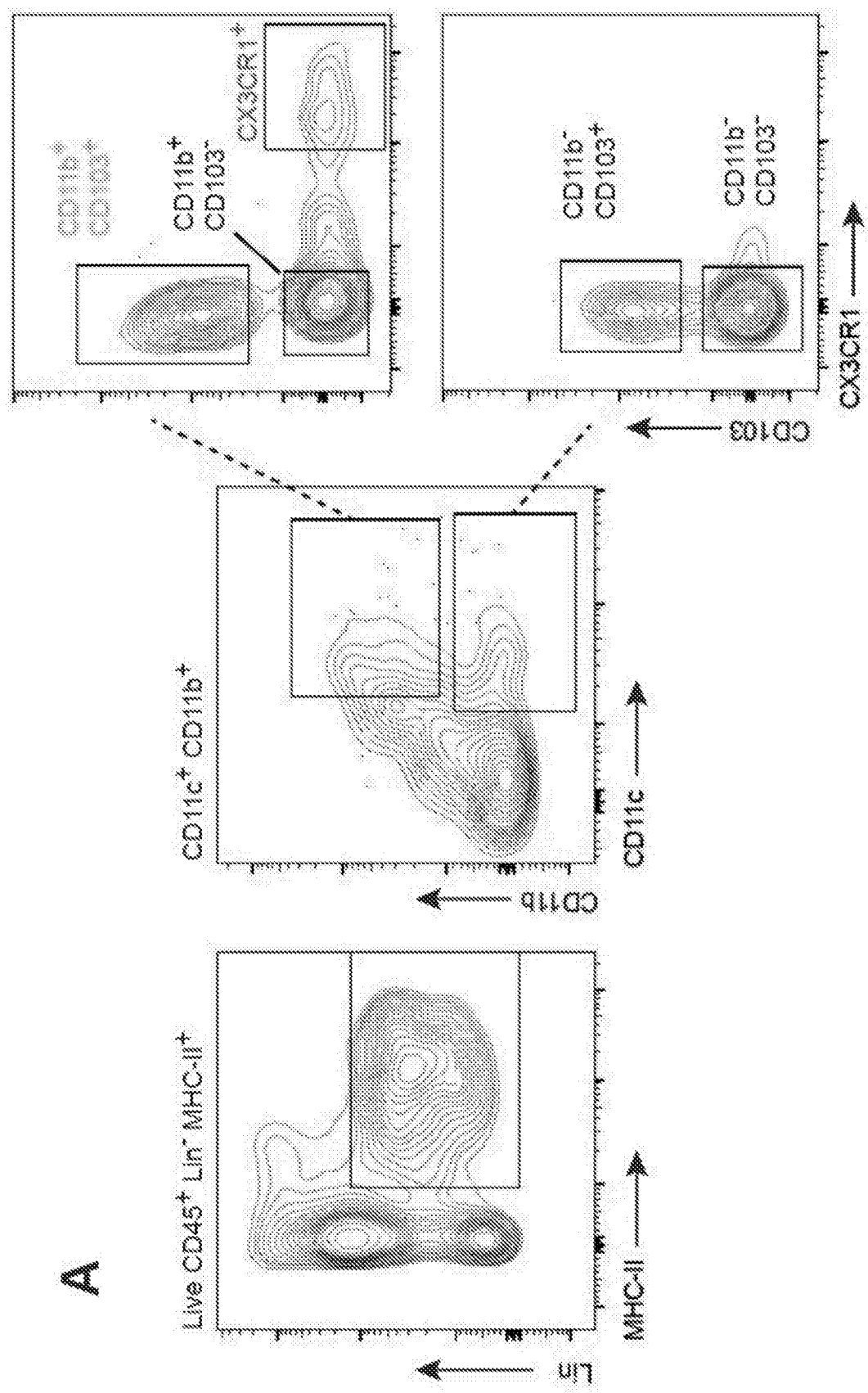
FIG. 5. Cell sorting strategy and costimulatory molecules expression by intestinal phagocytes upon *C. albicans* colonization. LP cells were isolated as described in the method section. Cell sorting strategy for purifying phagocytic populations from the colon of Cx3cr1$^{GFP/+}$ mice (A). For the quantification of CD40 and CD86 expression among phagocytic populations following *C. albicans* colonization, cells were first gated on singlet, live and lineage negative (CD3, CD19, TCRβ, Ly6c, NK1.1) populations, and subdivided into CD11c⁺ CD11b⁺ CD103⁺; CD11c⁺ CD11b⁺ CD103⁻ CD11c⁺ CD11b⁺ CX3CR1⁺; CD11c⁺ CD11b⁻ CD103⁺ and CD11c⁺ CD11b⁻ CD103⁻ subsets (B).
Figure 5:
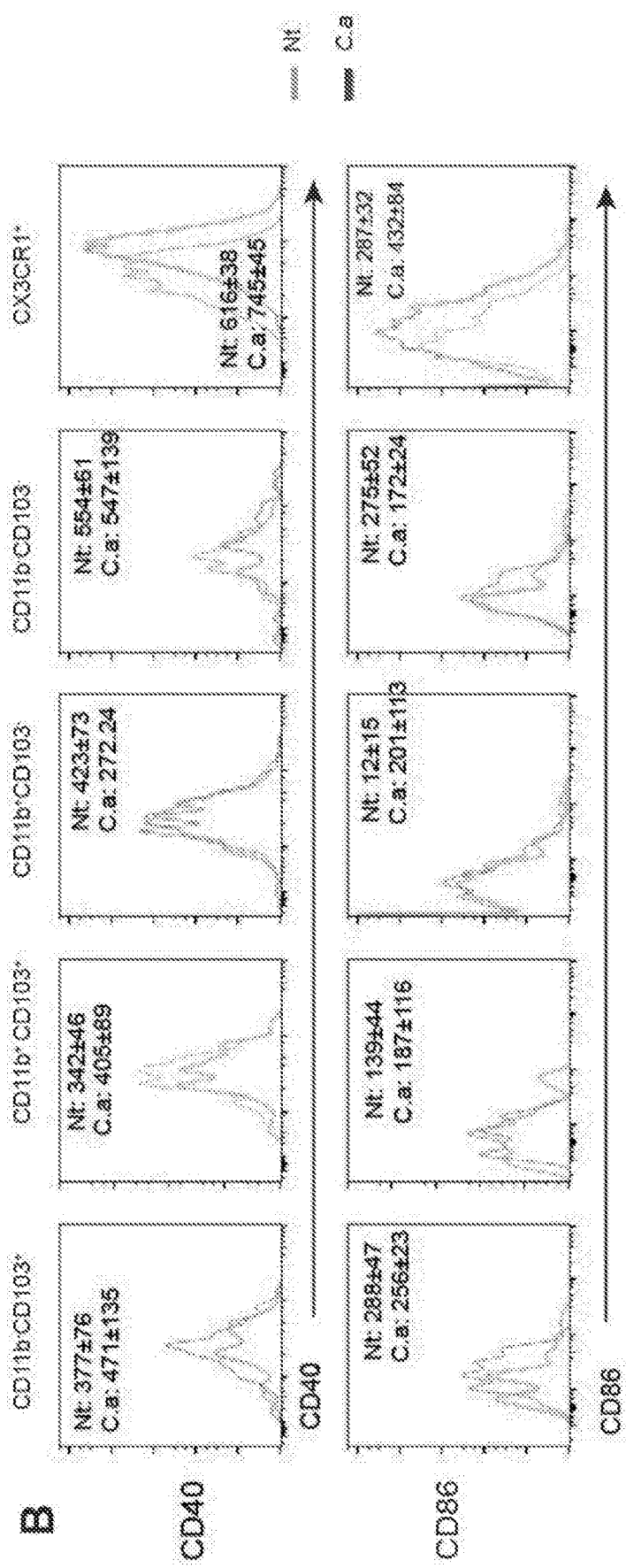
Figure 6:
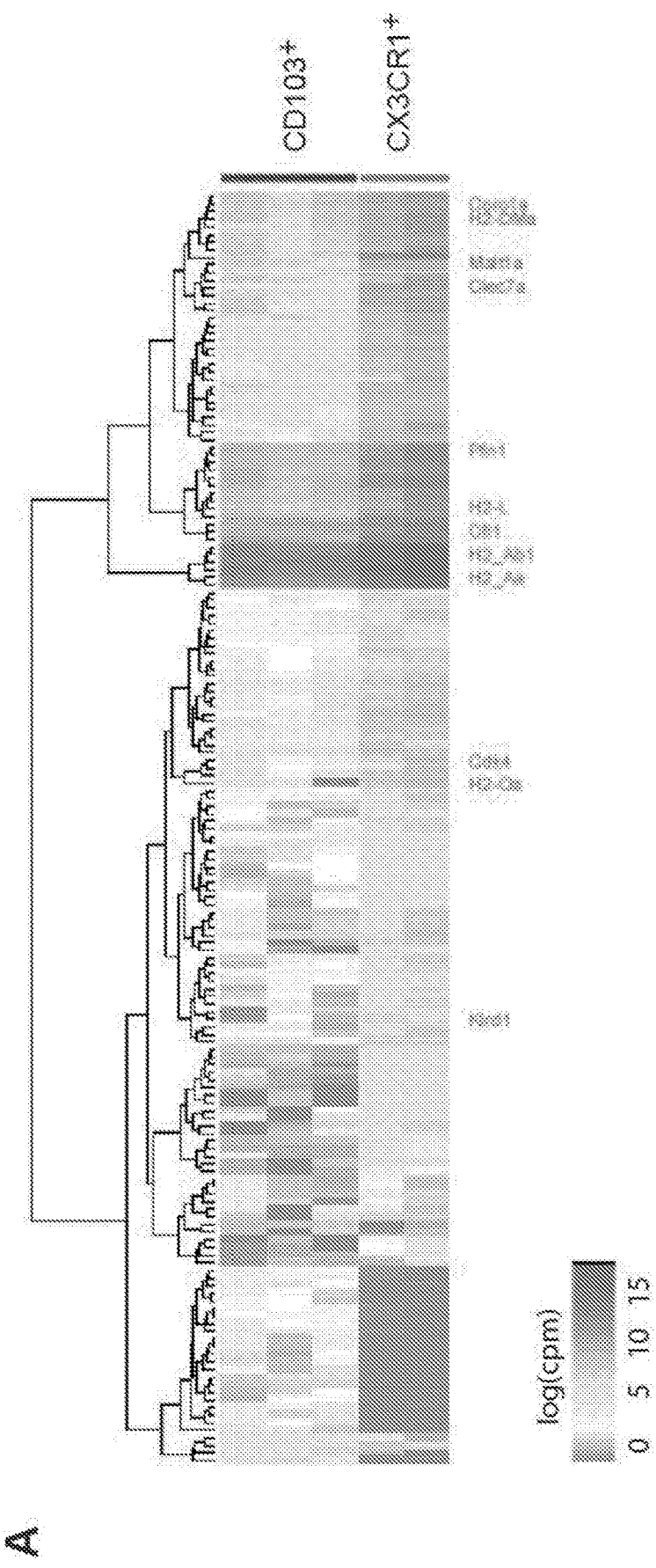
FIG. 6. RNA sequencing analysis of sorted CD11b⁺ CD103⁺ DCs and CX3CR1⁺ MNPs. Cells were sorted as in FIG. 5. Genes OTUs were clustered on the y axis based on Euclidean measures. Unsupervised clustering/heatmap on the left indicate log count per millions [log(cpm)] of the expressed genes in sorted CD11b⁺ CD103⁺ cells and CD11b⁺ CX3CR1⁺ cells (A). Network of expressed genes involved in fungal recognition was generated using Metacore (Thomson Reuter) Network was visualized with Cytoscape (B).
Figure 6:
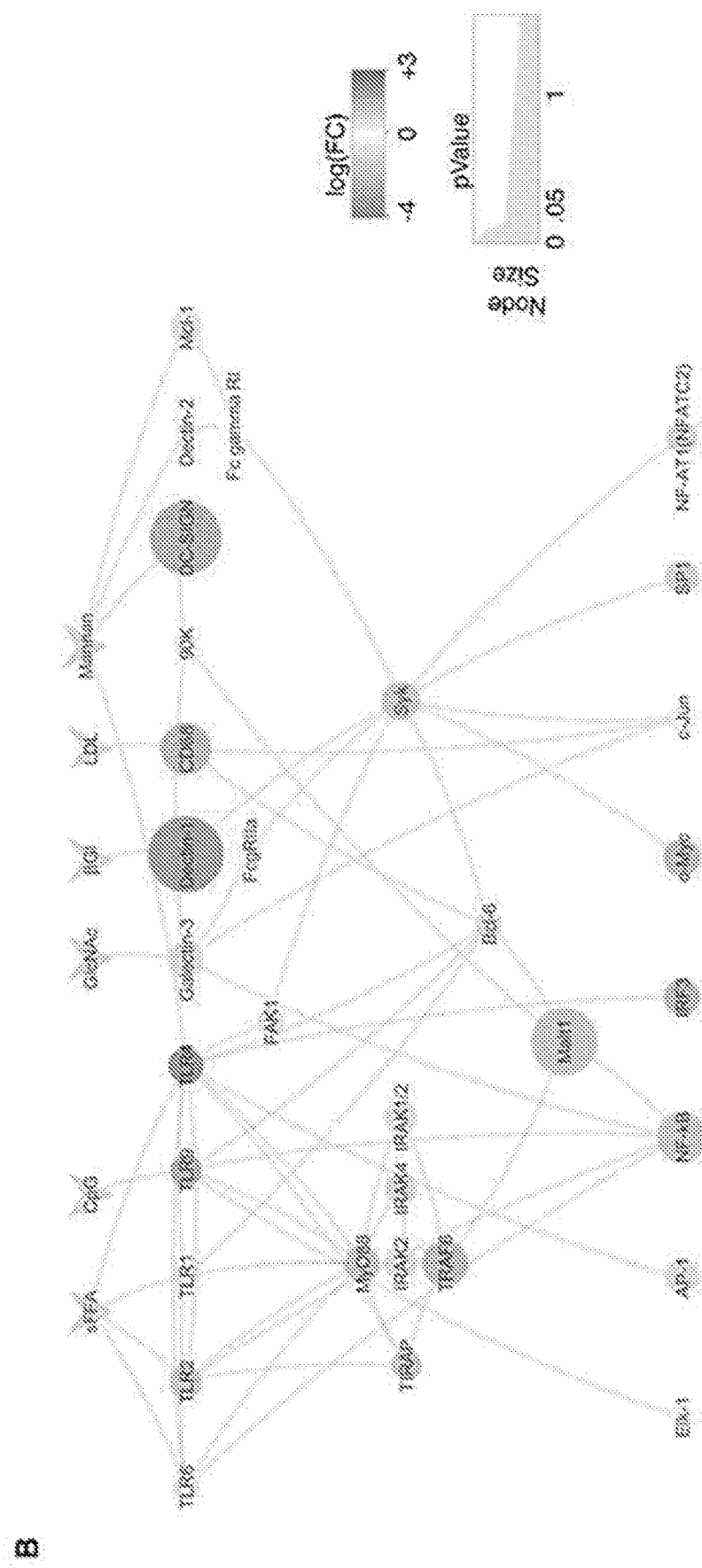
Figure 7:
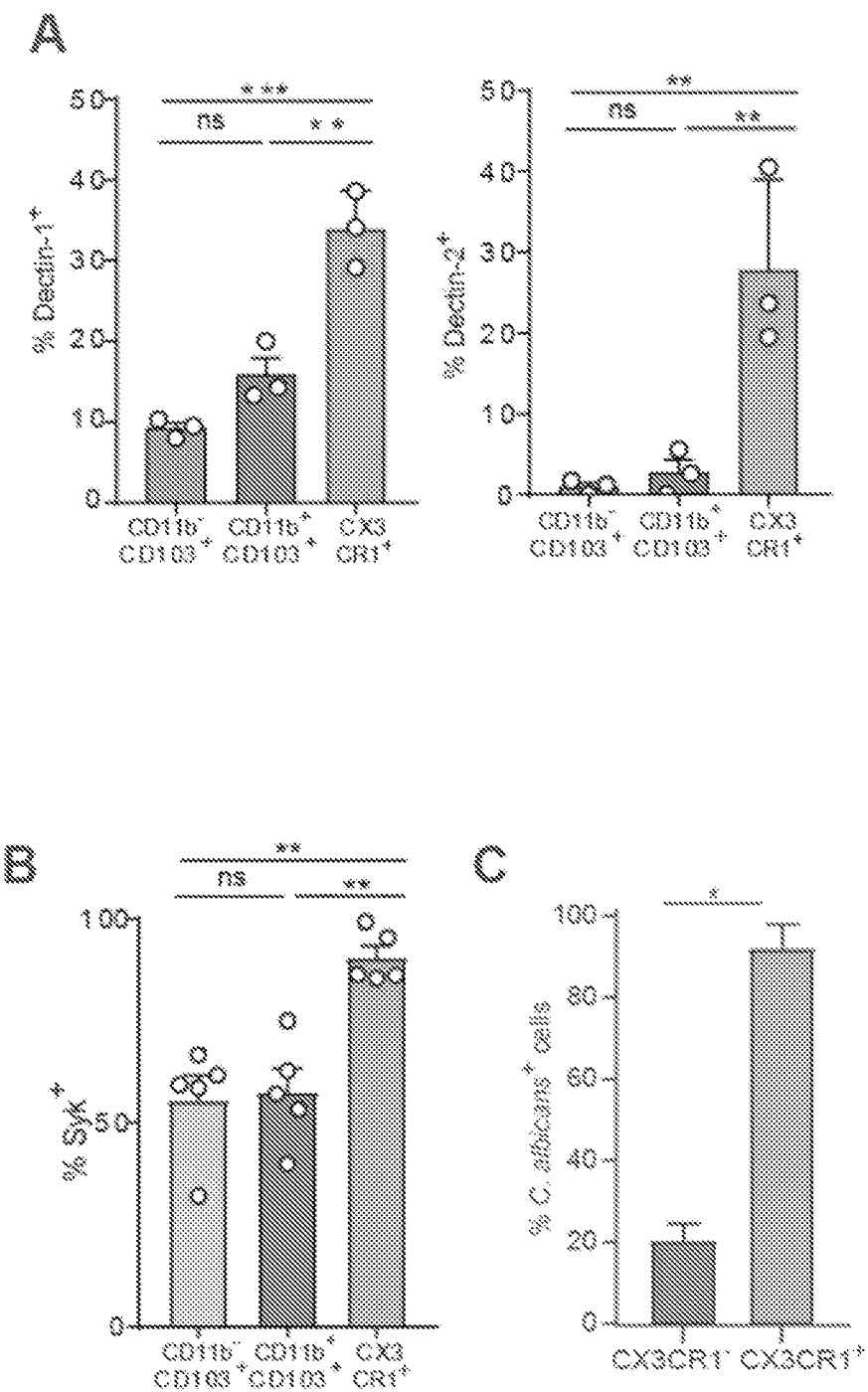
FIG. 7. CLR expression by intestinal phagocytes and *C. albicans* uptake by CX3CR1⁺ MNPs. Quantification of dectin-1, dectin-2 (A) and Syk (B) expression by flow cytometry among CD11c⁺ CD11b⁻ CD103⁺; CD11c⁺ CD11b⁺ CD103⁺ and CD11c⁺ CD11b⁺ CX3CR1⁺ cells in C57BL6 mice. Quantification (C) and 3D rendering (D) of confocal stack showing intake of RFP-*C. albicans* by CX3CR1⁺ and CX3CR1⁻ cells in the intestines of Cx3cr1$^{GFP/+}$.
Figure 7:
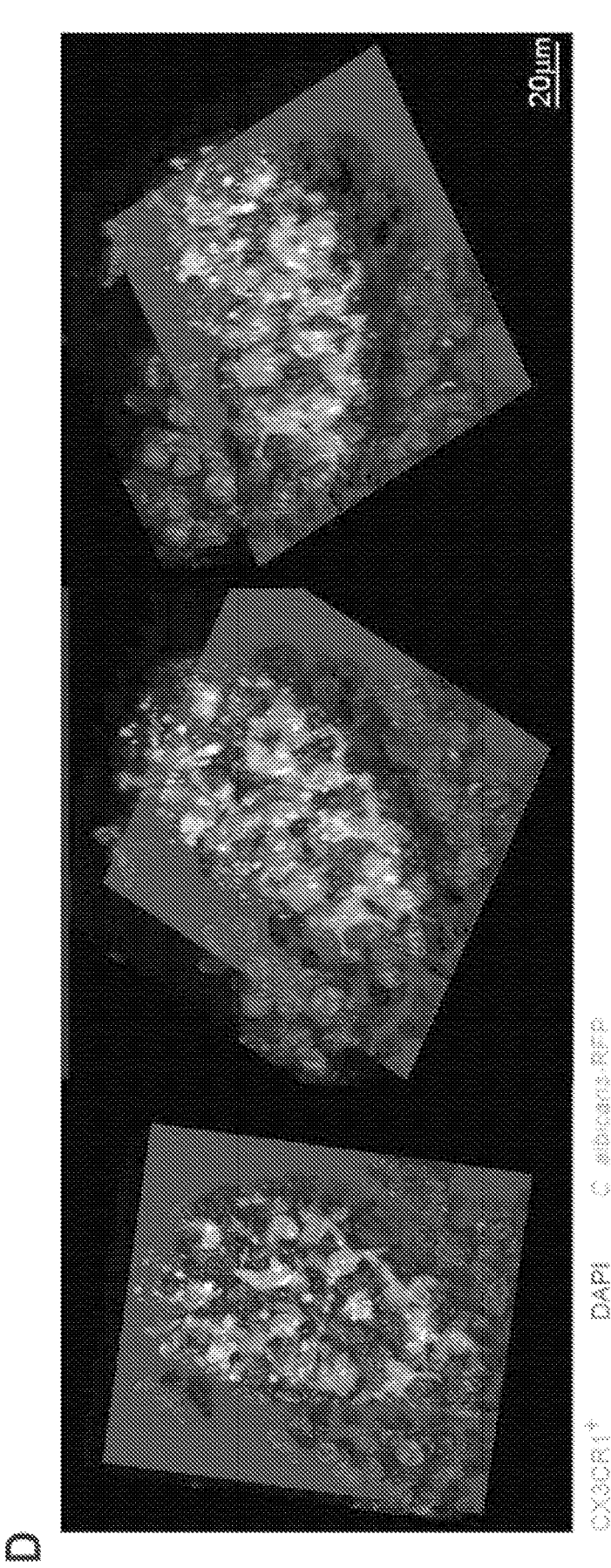

To assess the in vivo ability of gut resident phagocytes to respond to fungi, we colonized mice with the opportunistic human commensal *Candida albicans* and analyzed the surface expression of the costimulatory molecules CD40 and CD86 among those cells. We found that colonization with *C. albicans* increased the surface expression of CD40 and CD86 among $CX3CR1^+$ MNPs but not among the other subsets (FIG. 5A, B). We thus assessed the ability of $CX3CR1^+$ MNPs to recognize intestinal fungi. We purified $CX3CR1^+$ MNPs from the intestinal LP, performed RNA sequencing (RNA-Seq) and compared their expression profiles to those of $CD11b^+$ $CD103^+$ DCs (FIGS. 1A and B; FIG. 6), that have been shown to respond to lung fungal infection (Kinnebrew et al., 2012, Immunity 36(2): 276-287; Schlitzer et al., 2013, Immunity 38(5): 970-983). While both $CD11b^+$ $CD103^+$ DCs and $CX3CR1^+$ MNPs expressed genes involved in antigen presentation, $CX3CR1^+$ MNPs showed a higher expression of genes involved in fungal recognition (FIG. 1B; FIG. 6A, B). Quantitative PCR confirmed that transcripts encoding the fungal C type lectin receptors (CLRs) dectin-1 (Clec7α), dectin-2 (Clec6α) and mincle (Clec4e) were highly present in $CX3CR1^+$ MNPs (FIG. 1C) and results obtained by flow cytometry supported those findings (FIGS. 1D and 7A). Further, we examined the in vivo intake of *Candida* by phagocytes in the murine small intestine and the colon. Confocal microscopy examination revealed that *Candida* was efficiently recognized by intestinal phagocytes in vivo, with over 80% of all $CX3CR1^+$ MNPs intaking *Candida* FIG. 1E, FIG. 7C, D). These results indicate that gut resident $CX3CR1^+$ MNPs are equipped to efficiently recognize and respond to intestinal fungi in vivo.

Figure 8:
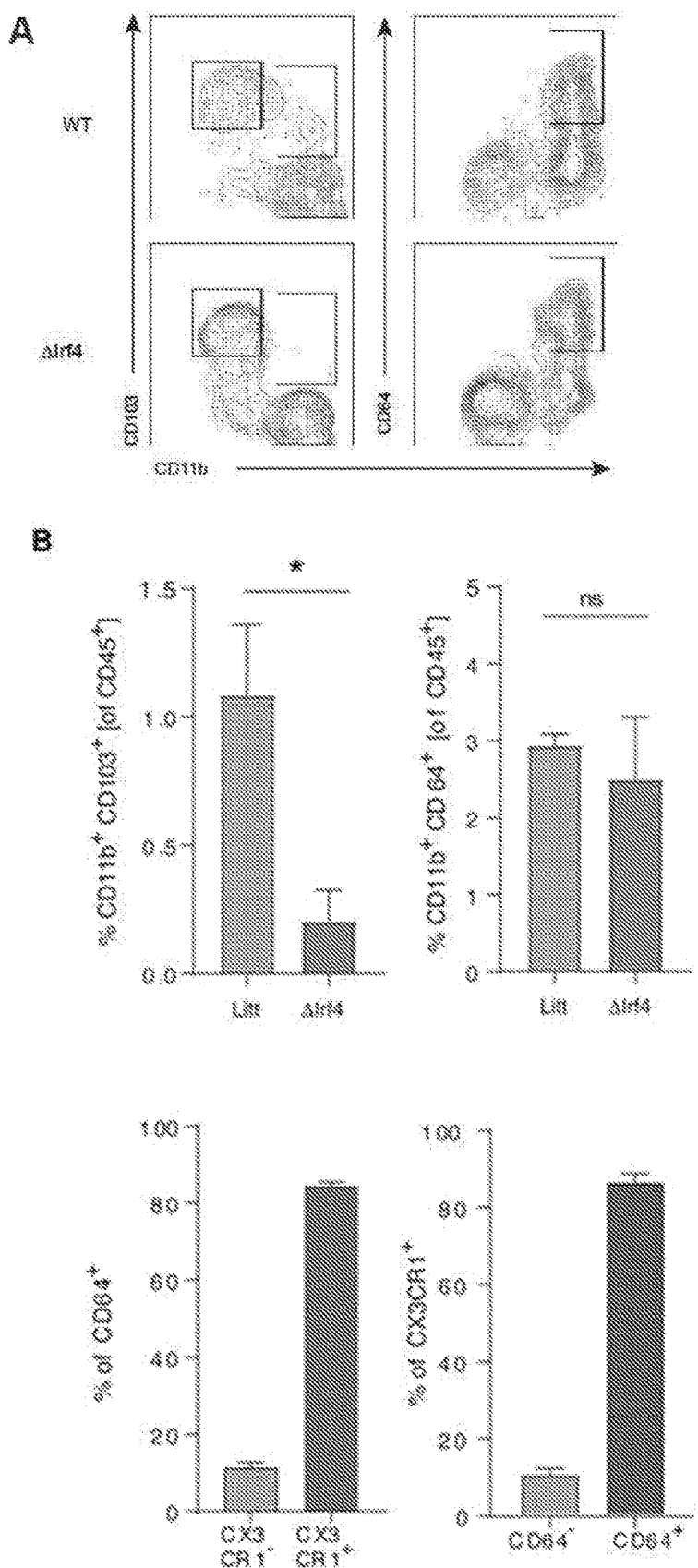
FIG. 8. Depletion of gut resident phagocytes. Representative flow cytometry plot of the colonic, Lin⁻ CD45⁺ MHC-II⁺ CD11c⁺ lymphocytes in 4Irf4 (Cd11c-cre⁺/⁻ Irf4$^{fl/fl}$ mice) mice or wild type (Cd11c-cre⁻/⁻ Irf4$^{fl/fl}$ mice) littermates (A). Quantification of the CD11b⁺ CD103⁺ and CD11b⁺ CD64⁺ subsets among and CD45⁺ cells (B). Expression of CX3CR1 among, Lin⁻ CD45⁺ MHC-II⁺ CD11c⁺ CD11b⁺ CD64⁺ cells and of CD64 among Lin-CD45+MHC-II+ CD11c+ CD11b+ CX3CR1+ cells. CD64 is expressed on CX3CR1⁺ MNPs and is used to quantify their depletion in D and E (C). Representative flow cytometry plot of colonic, Lin⁻ CD45⁺ MHC-II⁺ CD11c⁺ cells in ΔCX3CR1 mice (Cd11c-cre⁺/⁻ Cx3cr1$^{DTR}$+DT) or wild type (Cd11c-cre⁻/⁻ Cx3cr1$^{DTR}$+DT) littermates (D). Quantification of the CD11b⁺ CD64⁺ and CD11b⁺ CD103⁺ subsets among CD45⁺ cells (E). Data expressed as mean±SEM of individual mice, representative of at least two independent experiments.
Figure 8:
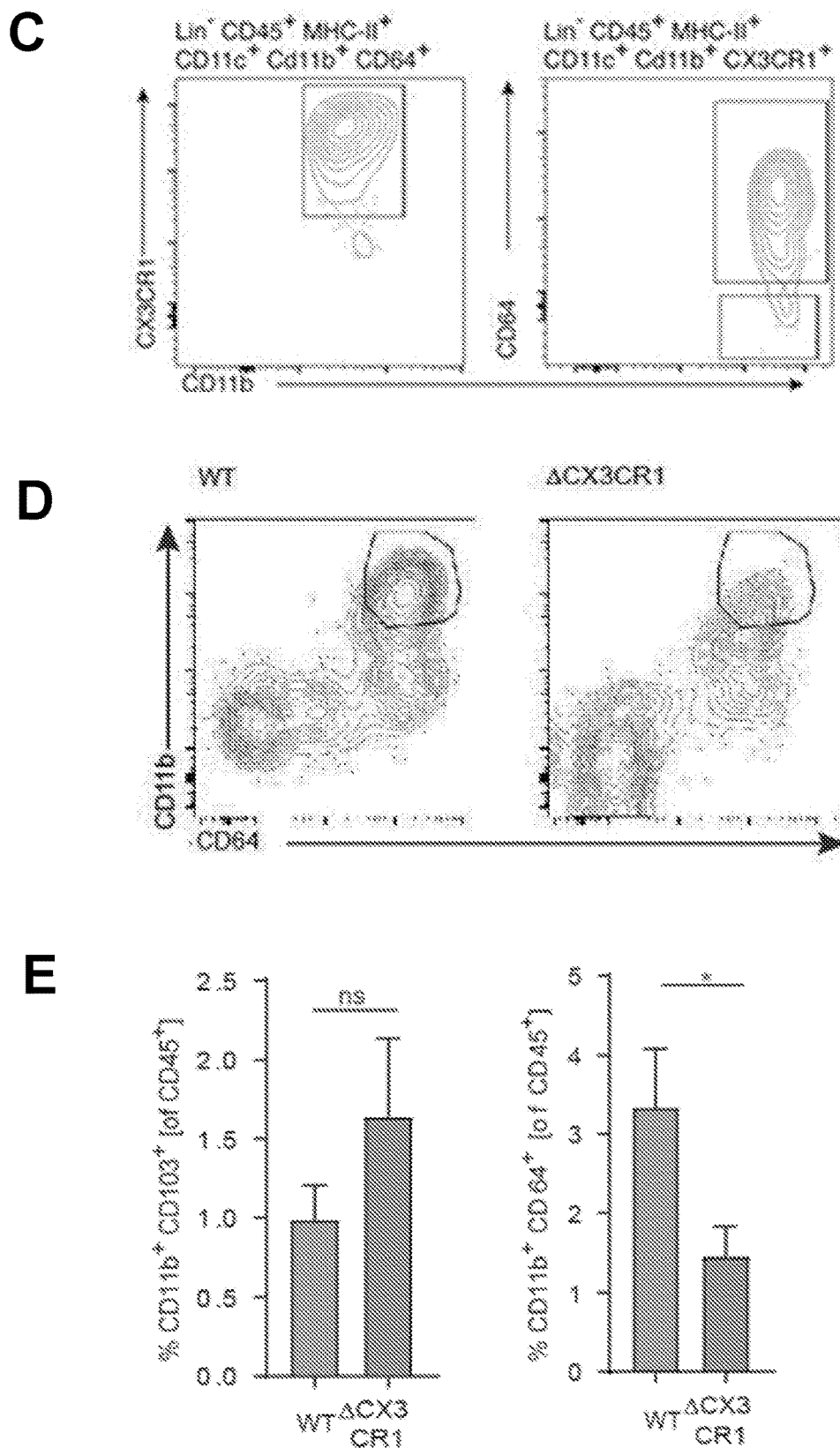

Both $CX3CR1^+$ MNPs and $CD11b^+$ $CD103^+$ DCs have been shown to play a role in the regulation of adaptive immunity to commensal and pathogenic bacteria (Rescigno et al., 2001, Nat Immunol 2(4): 361-367; Niess et al., 2005, Science 307(5707): 254-258; Persson et al., 2013, Immunity 38(5): 958-969; Schlitzer et al., 2013, Immunity 38(5): 970-983; Aychek et al., 2015, Nat Commun 6: 6525; Panea et al., 2015, Cell Rep 12(8): 1314-1324). $CX3CR1^+$ MNPs are involved in the induction of Th17 responses to intestinal bacteria and are essential for the killing of Candida in the kidneys during systemic infection (Lionakis et al., 2013, J Clin Invest 123(12): 5035-5051). Conversely, several studies have suggested a central role for IRF4-dependent $CD11b^+$ $CD103^+$ DCs in intestinal Th17 cell differentiation, as well as Th17-induced bacterial and fungal clearance in the lung (Persson et al., 2013, Immunity 38(5): 958-969; Schlitzer et al., 2013, Immunity 38(5): 970-983). Further, conventional migratory $CD103^+$ $CD11b^-$ DCs have been shown to be a cellular entry point to other opportunistic pathogens and are absent in $Batf3^{-/-}$ mice (Edelson et al., 2011, Immunity 35(2): 236-248) (FIGS. 14A and B). To directly assess the role of intestinal $CD11b^+$ $CD103^+$ DCs and $CX3CR1^+$ MNPs in the induction of anti-fungal immune responses, we crossed flox inducible $Irf4^{fl/fl}$ allele mice (Klein et al., 2006, Nat Immunol 7(7): 773-782) or flox inducible $Cx3cr1^{DTR}$ mice (Diehl et al., 2013, Nature 494 (7435): 116-120), with transgenic Cd11c-Cre mice (Caton et al., 2007, J Exp Med 204(7): 1653-1664). The first strategy allowed the specific ablation of Irf4 in DCs leading to the loss of intestinal $CD11b^+$ $CD103^+$ DCs (referred as ΔIrf4 mice), but intact $CX3CR1^+$ MNPs (Schlitzer et al., 2013, Immunity 38(5): 970-983) (FIG. 8A, B). The second strategy allowed for the selective depletion of intestinal $CX3CR1^+$ MNPs upon administration of diphtheria toxin (DT, mice referred as ΔCX3CR1), without affecting $CD11b^+$ $CD103^+$ DCs (Diehl et al., 2013, Nature 494(7435): 116-120) (FIG. 8C-E).

Figure 2:
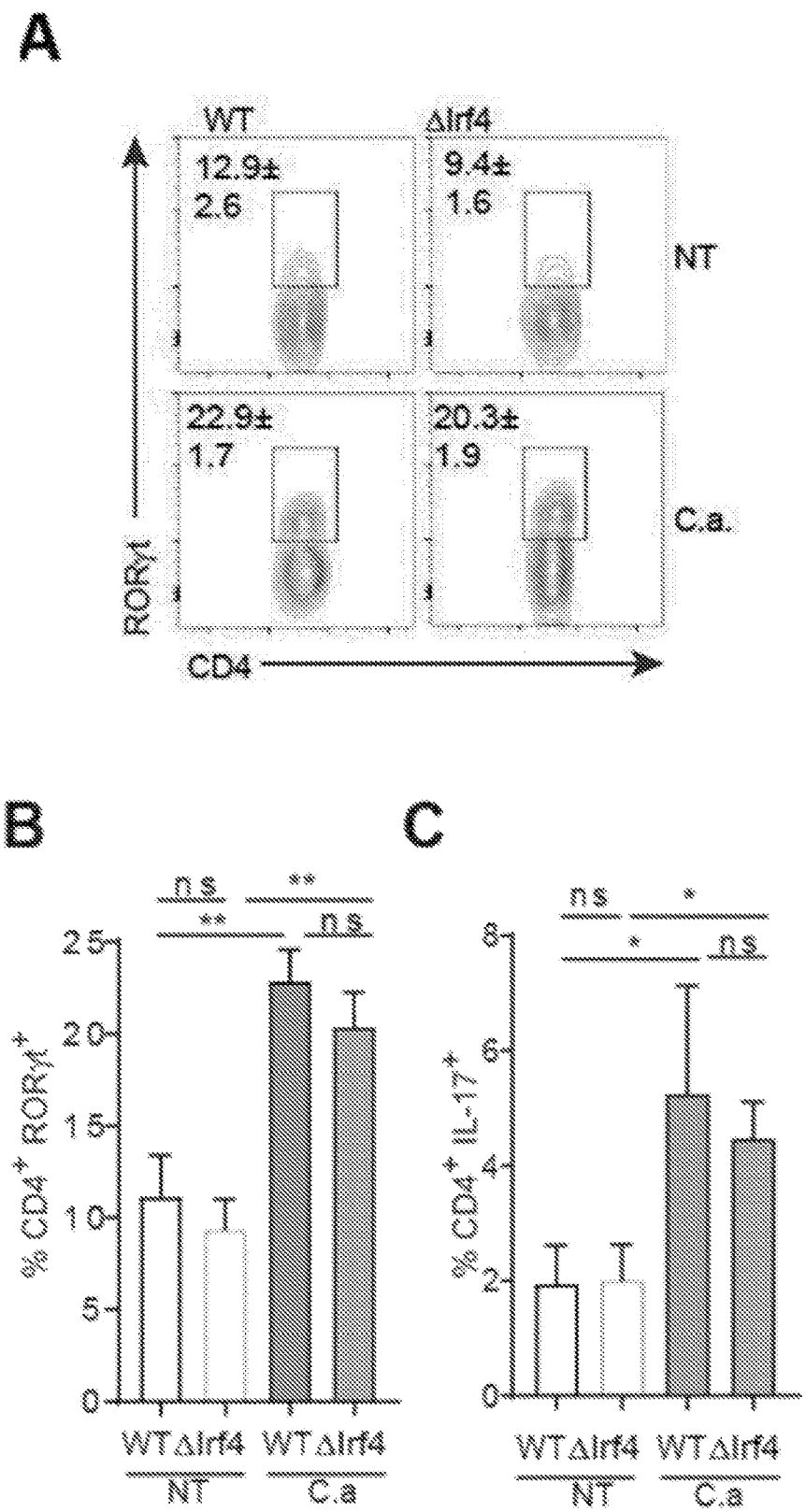
FIG. 2. CX3CR1+ MNPs control gut antifungal immunity. *Colonic lamina propria* cells were collected from ΔIrf4 mice or control littermates (WT) fed with 5·10⁸ CFU *C. albicans* (C.a) every 3 days for 10 days and expression of RORγt (A, B) and IL-17 (C) by CD4⁺ T cells in the colon were assessed. Cd11c-Cre⁺/⁻ $^{CX}$3CR1$^{DTR}$ mice (ΔCX3CR1) or Cd11c-Cre⁻/⁻ CX3CR1$^{DTR}$ littermates (WT) were treated with diphtheria toxin (DT), and fed with *C. albicans*. RORγt (D, E) and IL-17 (F) expression by the CD4⁺ T cells in the colon were assessed. *C. albicans* cfu/g in the feces of control, ΔIrf4 and ΔCX3CR1 mice at day 10 (G). IgG responses against the commensal *C. tropicalis* and flagellin in non-treated ΔCX3CR1 mice and littermate controls (H). ΔCX3CR1 mice were injected i.p with *C. albicans* and systemic IgG responses were assessed at day 1, 2 and 5 (I). ΔCX3CR1 mice and control littermates were transferred with purified CD4⁺ Thy1.1⁺ OT-II cells, fed *C. albicans*-OVA and sacrificed after 10 days. Representative plots (J), and quantification (K) of CD4⁺ Thy1.1⁺ OT-II cells proliferation in colon (left panel) and mLNs (right panel). RORγt expression by the CD4⁺ T cells in the colon of Cx3cr1-Cre-ERT⁺/⁻ Syk$^{fl/fl}$ mice (ΔSyk) or littermates (WT) treated with tamoxifen was assessed (L). *C. albicans* cfu/g in the feces of WT and ΔSyk mice at day 7 (M). IgG responses against *C. tropicalis* in WT and ΔSyk mice at day 10 (N). Quantification of proliferating CF SE⁻ CD4⁺ Thy1.1⁺ OT-II cells in colon (left panel) and mLNs (right panel) in (ΔSyk) or littermates (WT) treated with tamoxifen (O). Data expressed as mean±SEM (n=4-7), representative of at least two independent experiments. Dots represent individual mice. *P<0.05, P<0.01, *P<0.001 (Mann Whitney Test (G, H, K, M, N), one-way ANOVA (B, C, E, F)).
Figure 2:
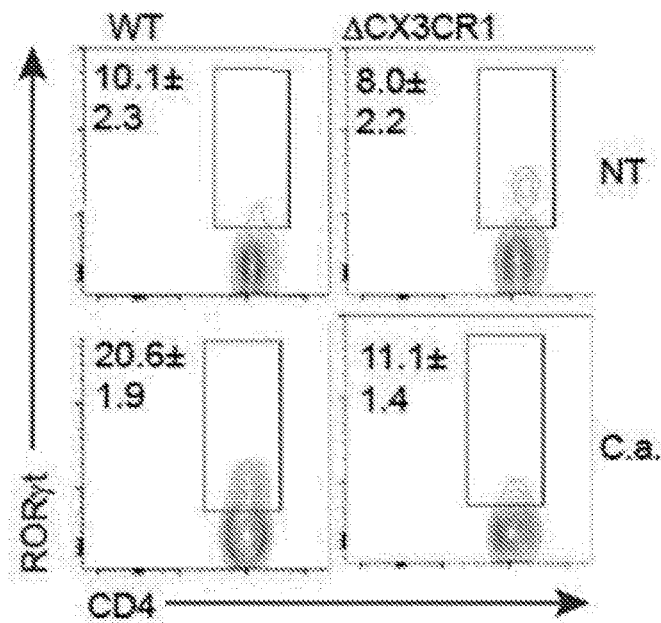
Figure 2:
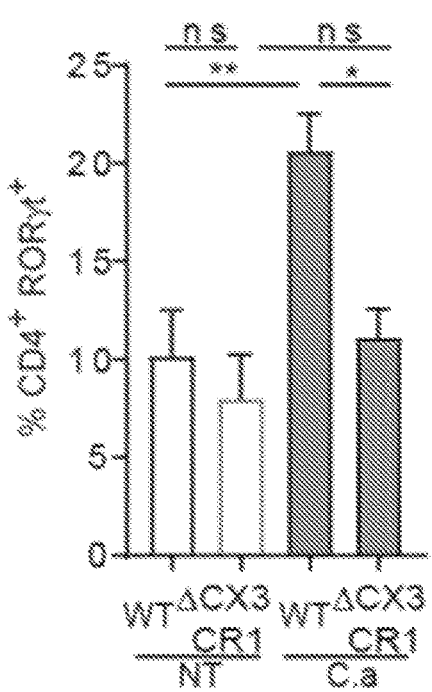
Figure 2:
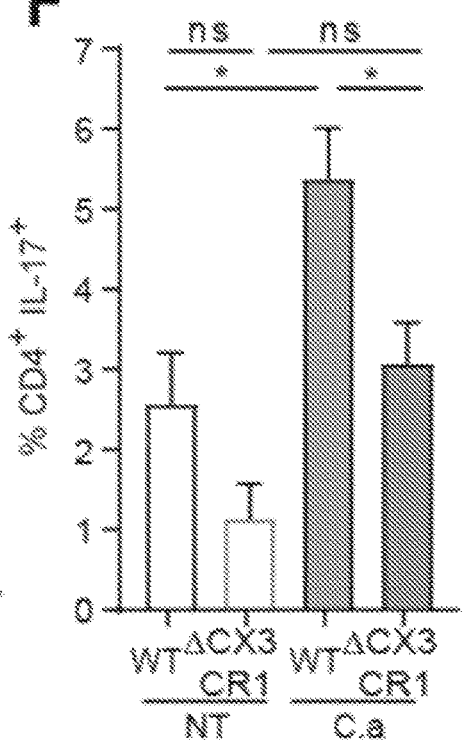
Figure 2:
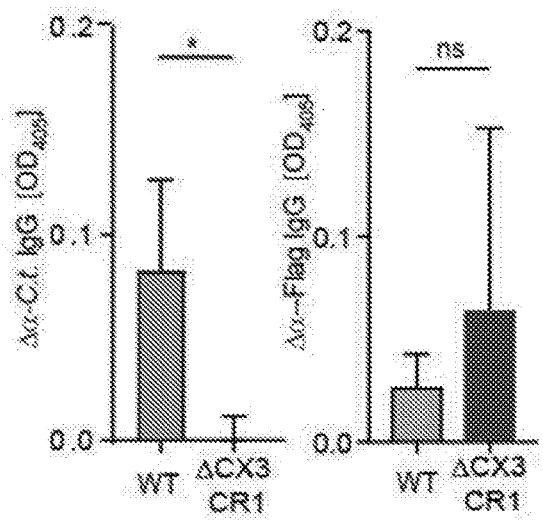
Figure 2:
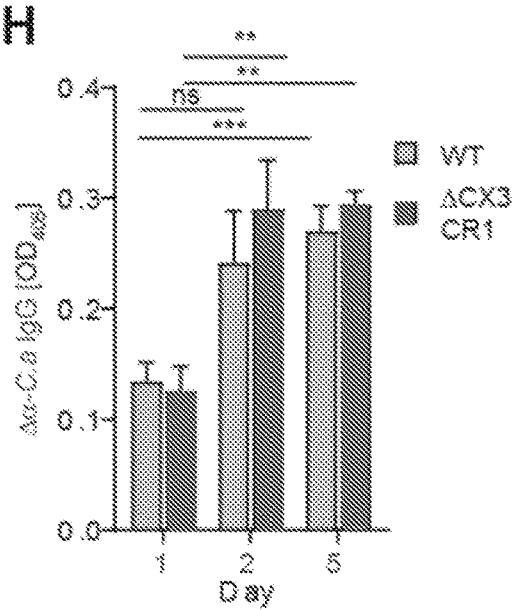
Figure 2:
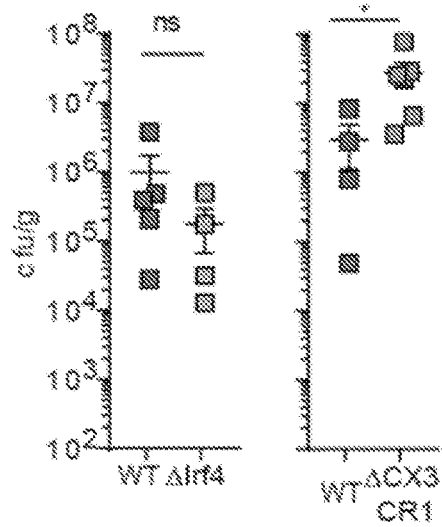
Figure 2:
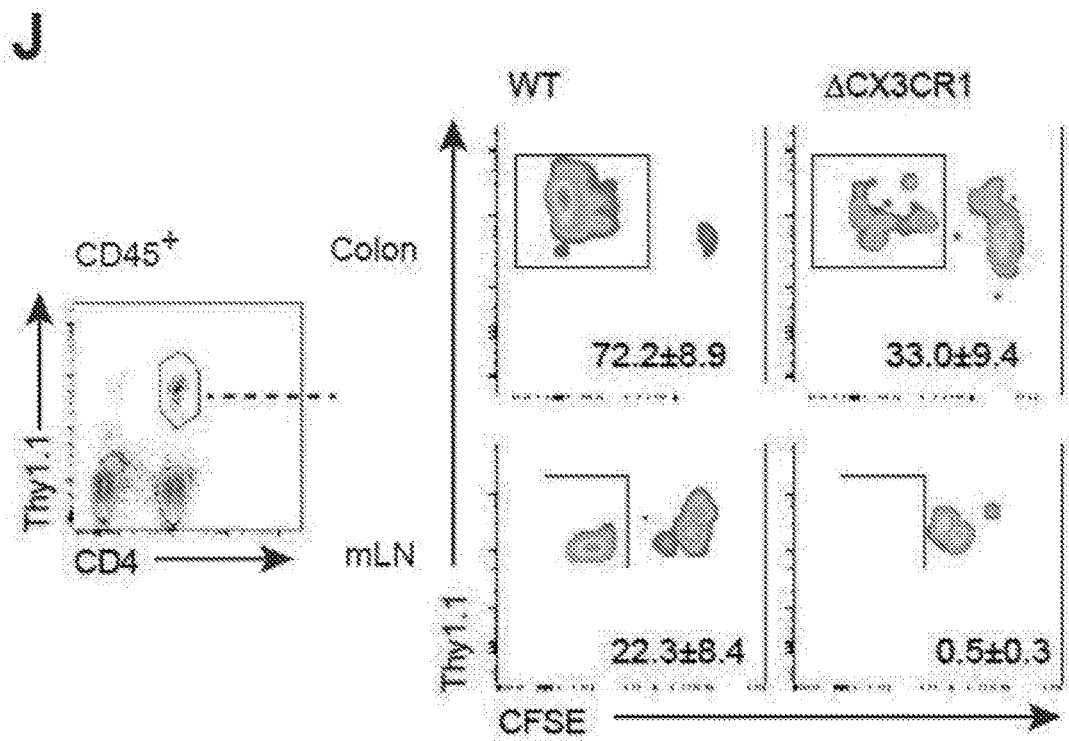
Figure 2:
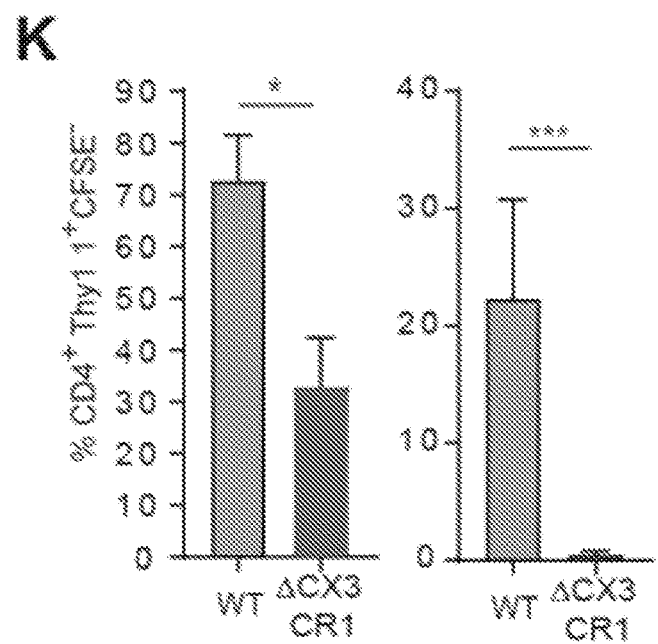
Figure 2:
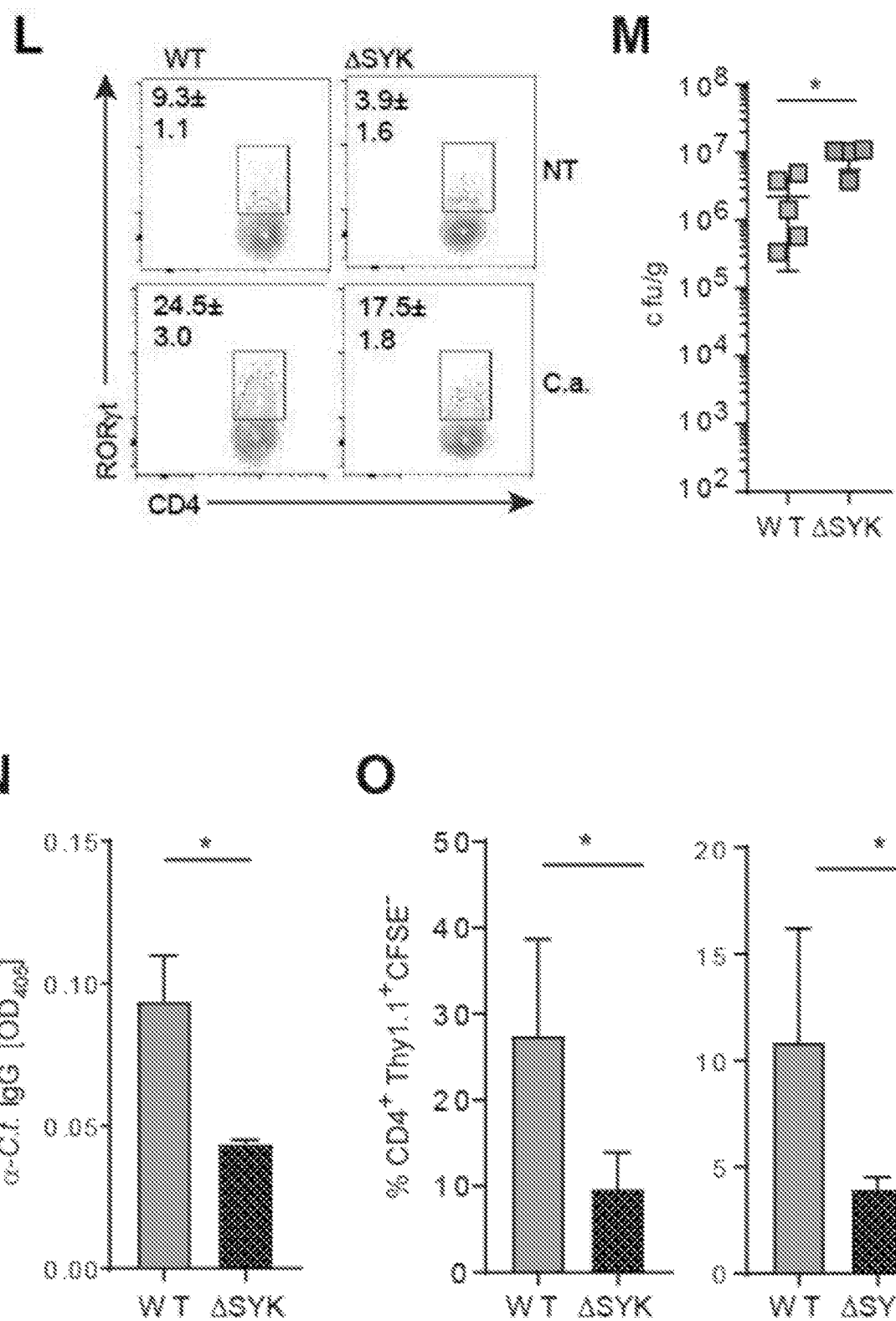
Figure 4:
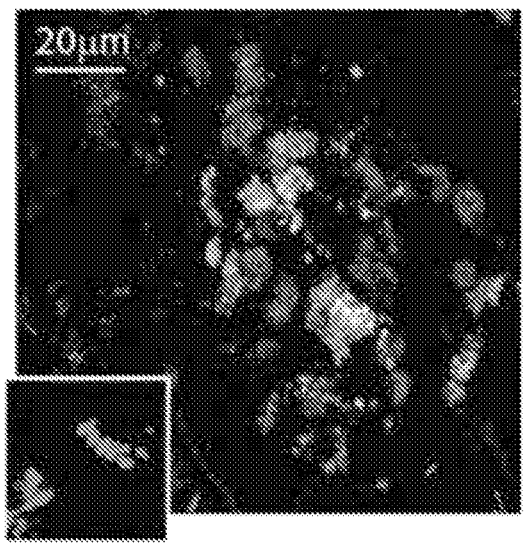
FIG. 4. Polymorphism in the coding region of CX3CR1 gene is associated with decreased anti-fungal IgG responses in CD patients. Representative pictures of the intake of different fungal species (colored) by CX3CR1⁺ MNPs (grey) in the colon (A). Association between the missense mutation rs3732378 and the systemic serologic markers anti-neutrophil cytoplasmic antibodies (anca), flagellin (cbir), *Pseudomonas fluorescens*—associated sequence I-2 (i2), and anti *S. cerevisiae* IgG antibodies (igg.asca). FA, frequency affected; FU, frequency unaffected; L95 and U95, lower and upper 95th confidence interval (B). IgG ASCA and anti-flagellin (cbir) IgG responses were assessed in the sera from rs3732378 homozygous (GG), heterozygous (AG) and control (AA) CD patients by ELISA (C). IgG responses against different commensal fungi (*Candida parapsilosis, Pichia kudrazevii, Saccharomyces cerevisiae, Aspergillus amstellodamii Malessizia restricta, Wallemia sebi, Rhodotorula mucilaginosa, Cladosporium cladosporioides*, and cbir were assessed (D). Dots represent individual patients. *P<0.05, P<0.01, *P<0.001 (Mann Whitney test (D), one-way ANOVA (C).
Figure 4:
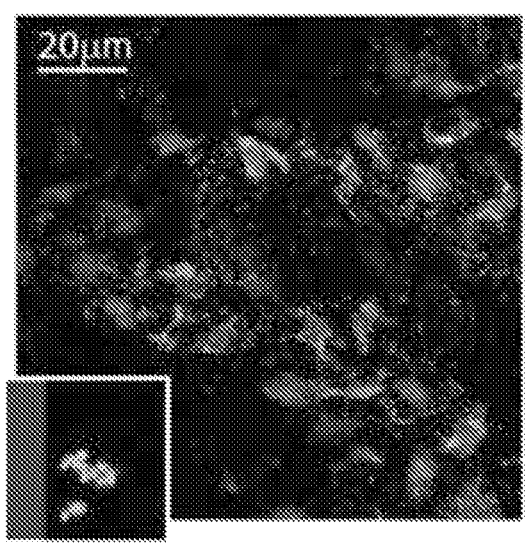
Figure 4:
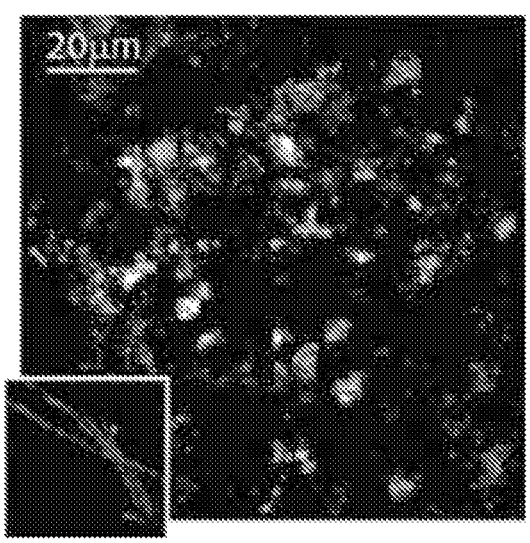
Figure 4:
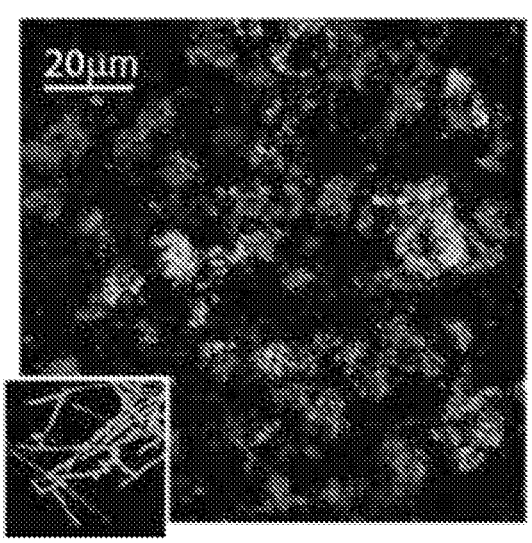
Figure 4:
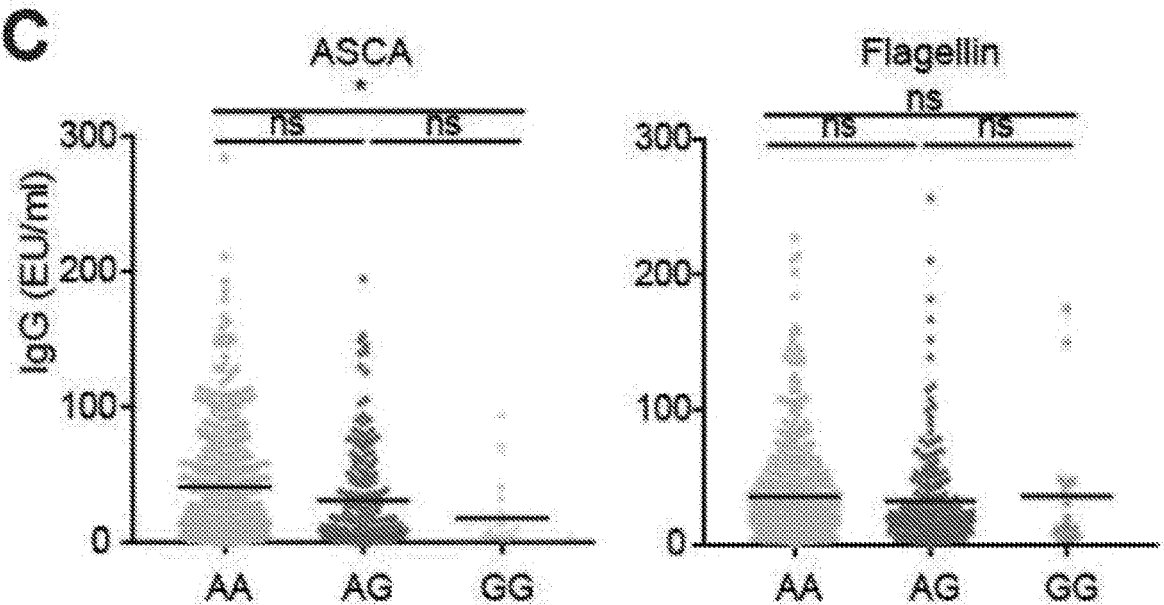
Figure 4:
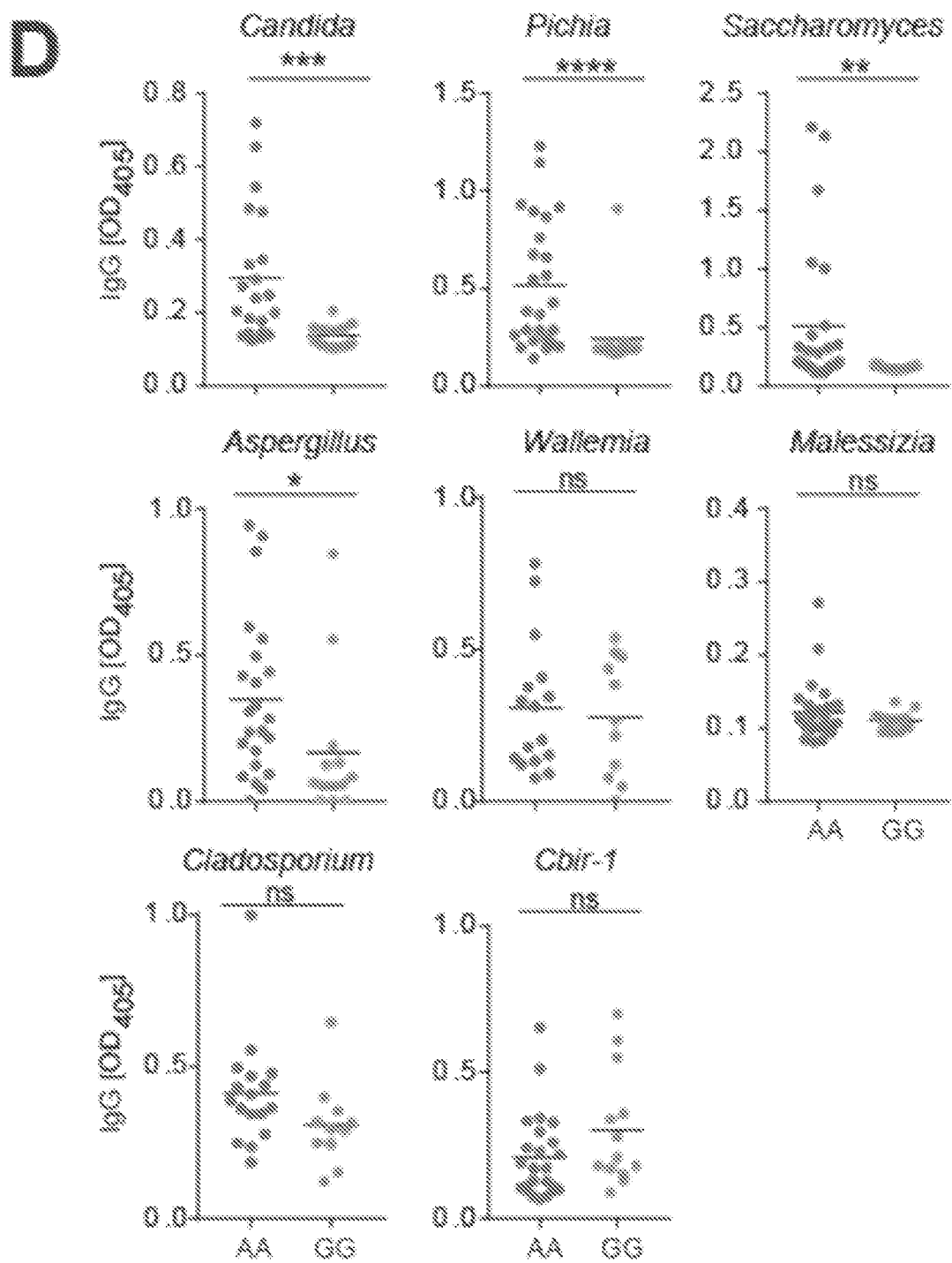
Figure 9:
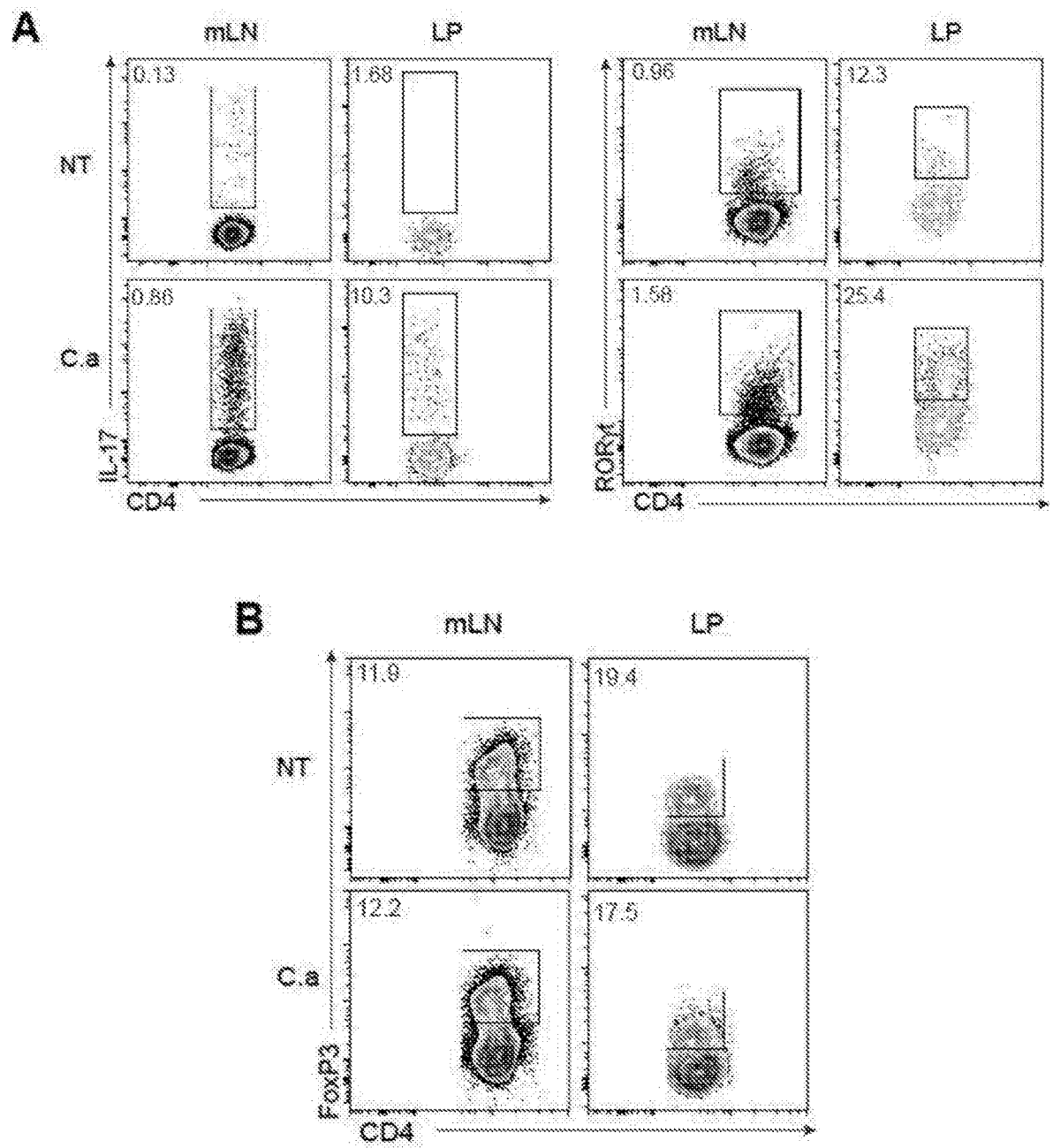
FIG. 9. Quantification of Th17 and Treg cells in the intestine following *C. albicans* colonization. Representative plot of IL-17 and RORγt expression among CD4⁺ T cells in the mLN (left) and colonic lamina propria (right) following *C. albicans* administration (A). Representative plot of FoxP3 expression among CD4⁺ T cells in the mLN (left) and colonic lamina propria (right) following *C. albicans* administration (B). Expression of RORγt in the colon of ΔIrf4 mice or control littermates (Litt) (C). Quantification of the FoxP3+ Treg cells among the CD4+ T cells in the colon of ΔCX3CR1 mice or wild type littermates (D). Data expressed as mean±SEM of individual mice, representative of at least two independent experiments.
Figure 9:
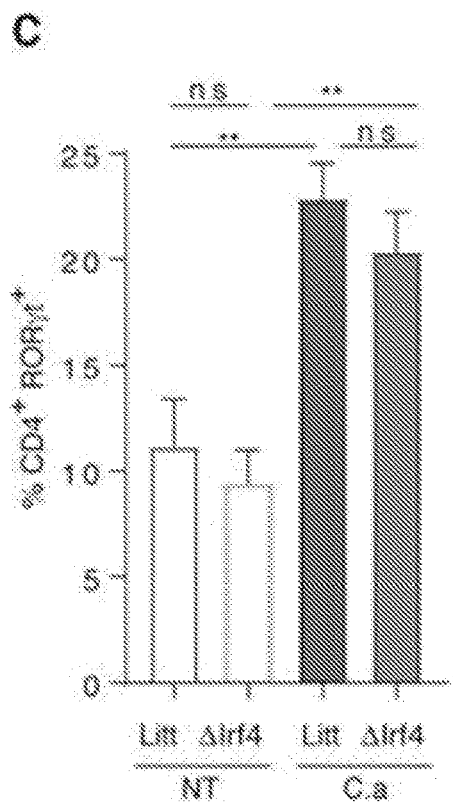
Figure 9:
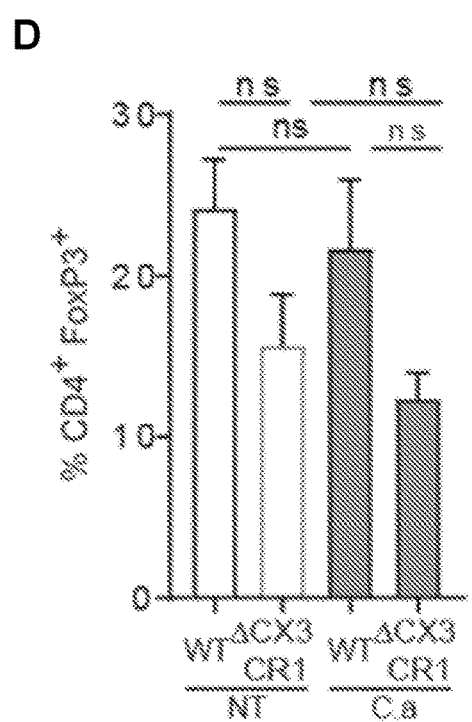
Figure 10:
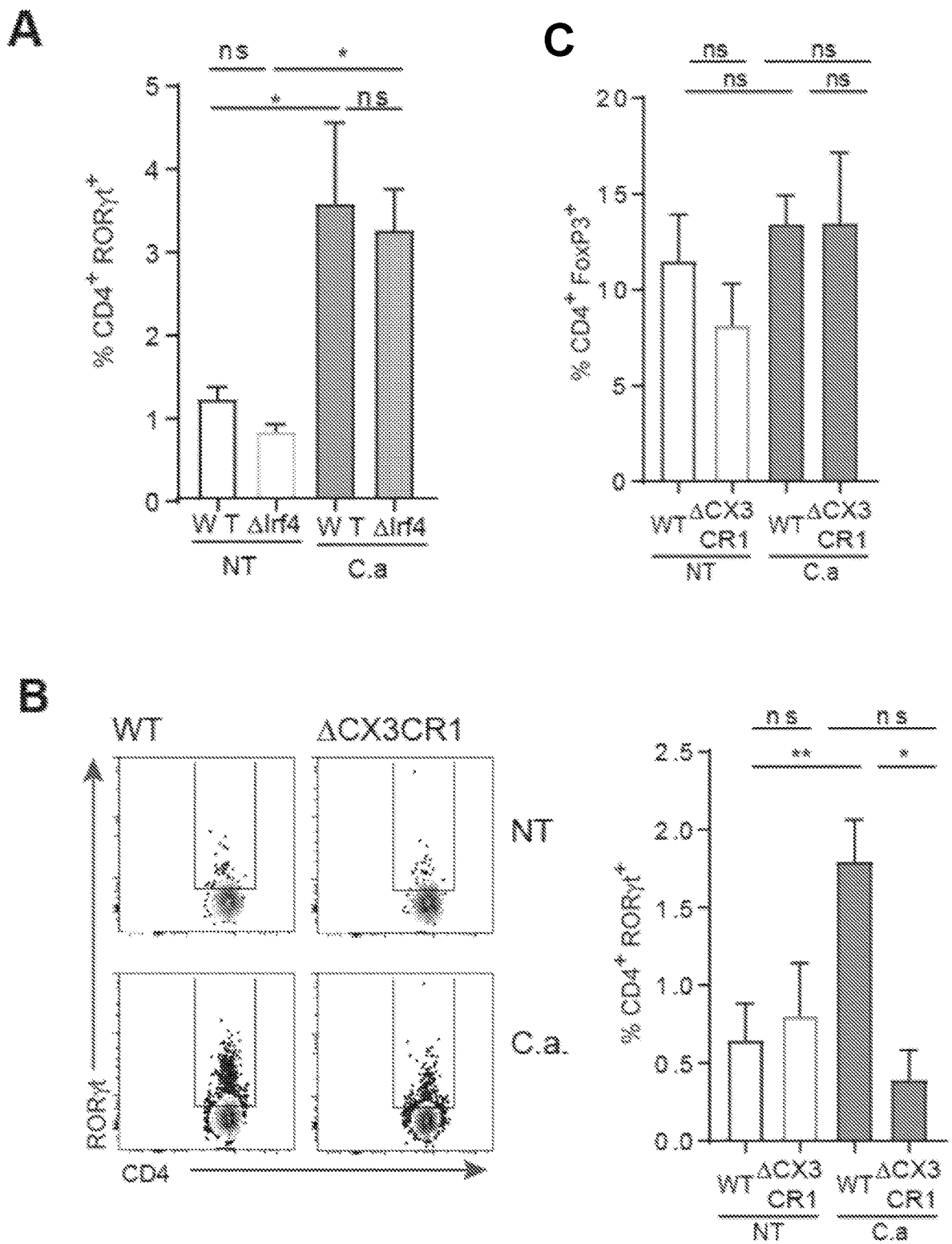
FIG. 10. Quantification of Th17 and Treg cells in the mesenteric LN (mLN) following *C. albicans* colonization. Quantification of RORγt+ Th17 among the CD4+ T cells in ΔIrf4 mice or wild type littermates (A). Representative flow cytometry plot and quantification of RORγt+ Th17 (B) and FoxP3+ Treg cells among the CD4+ T cells in ΔCX3CR1 mice or wild type littermates (C). Data expressed as mean±SEM of individual mice, representative of at least two independent experiments. *$P<0.05$, $P<0.01$, *$P<0.001$, one-way ANOVA.
Figure 14:
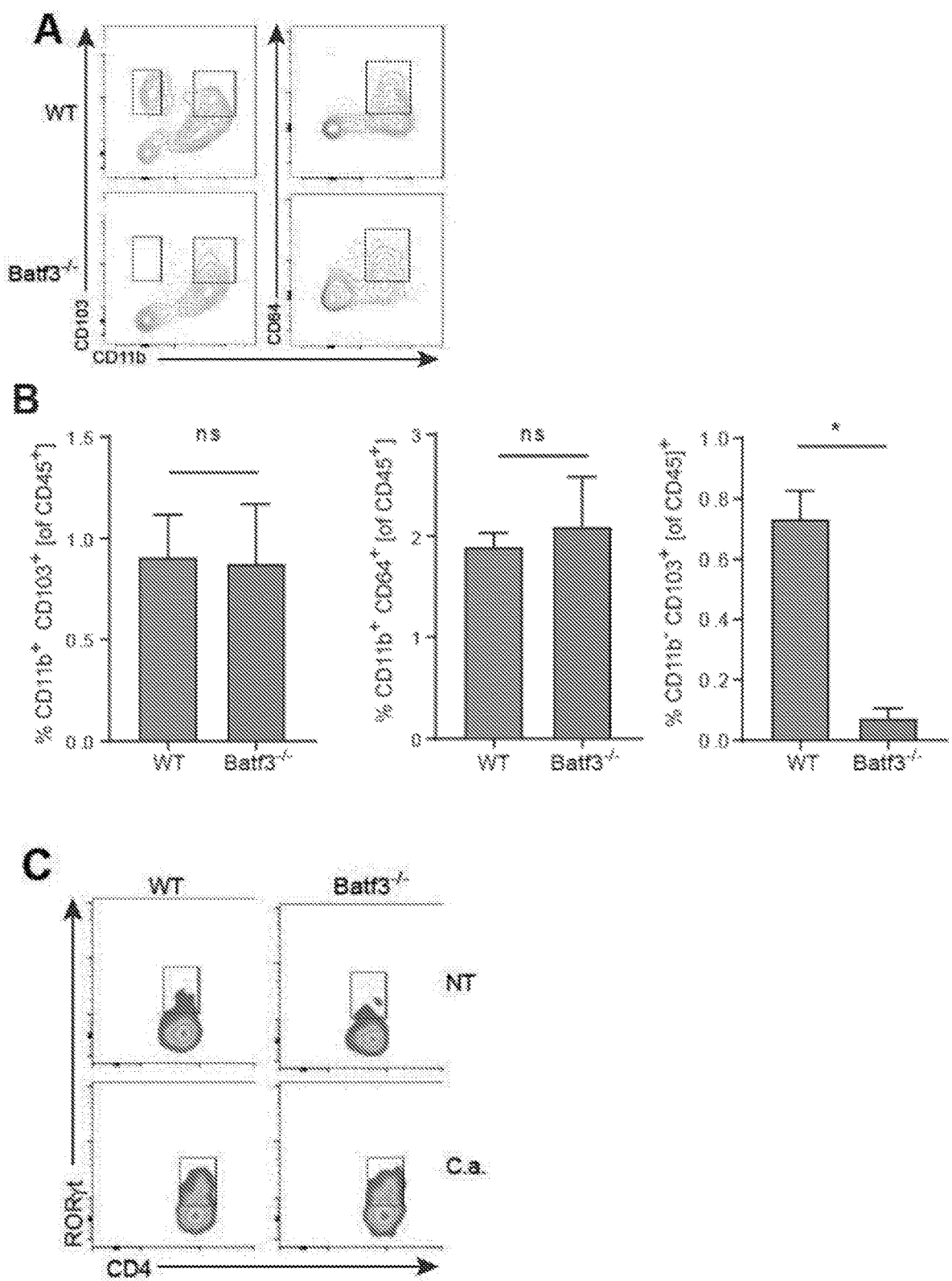
FIG. 14. Role of CD11b− CD103+ DCs in the induction of antifungal responses. Representative flow cytometry plot (A) and quantification of the CD11b+ CD103+, the CD11b+ CD64+, CD11b− CD103+ subsets among CD45+ cells (B) in Batf3−/− mice (B6.129S(C)-Batf3$^{tm1Kmm}$/J) or wild type (WT) mice. Representative flow cytometry plot (C) and quantification (D) of RORγt+ Th17 among colonic CD4+ T cells. Quantification of colonic IL-17+ Th17 (E) and FoxP3+ Treg cells (F) among CD4+ T cells in Batf3−/− and WT mice. Representative flow cytometry plot (G) and quantification (H) of RORγt+ Th17 among mLN CD4+ T cells in Batf3−/− or WT mice. Quantification of mLN IL-17+ Th17 (I) and FoxP3+ Treg cells (J) among CD4+ T cells in Batf3−/− mice or WT controls. Induction of systemic IgG responses (K) and *Candida* load in the feces (L) in Batf3−/− mice or WT controls fed with *C. albicans*. Quantification of proliferating CFSE− CD4+ Thy1.1+ OT-II cells in colon (M) and mLNs (N) in Batf3−/− and WT mice. Data expressed as mean±SEM of individual mice, representative of two independent experiments. *$P<0.05$, $P<0.01$, *$P<0.001$, Mann Whitney (B, K-N) and one-way ANOVA (D-F,H-J).
Figure 14:
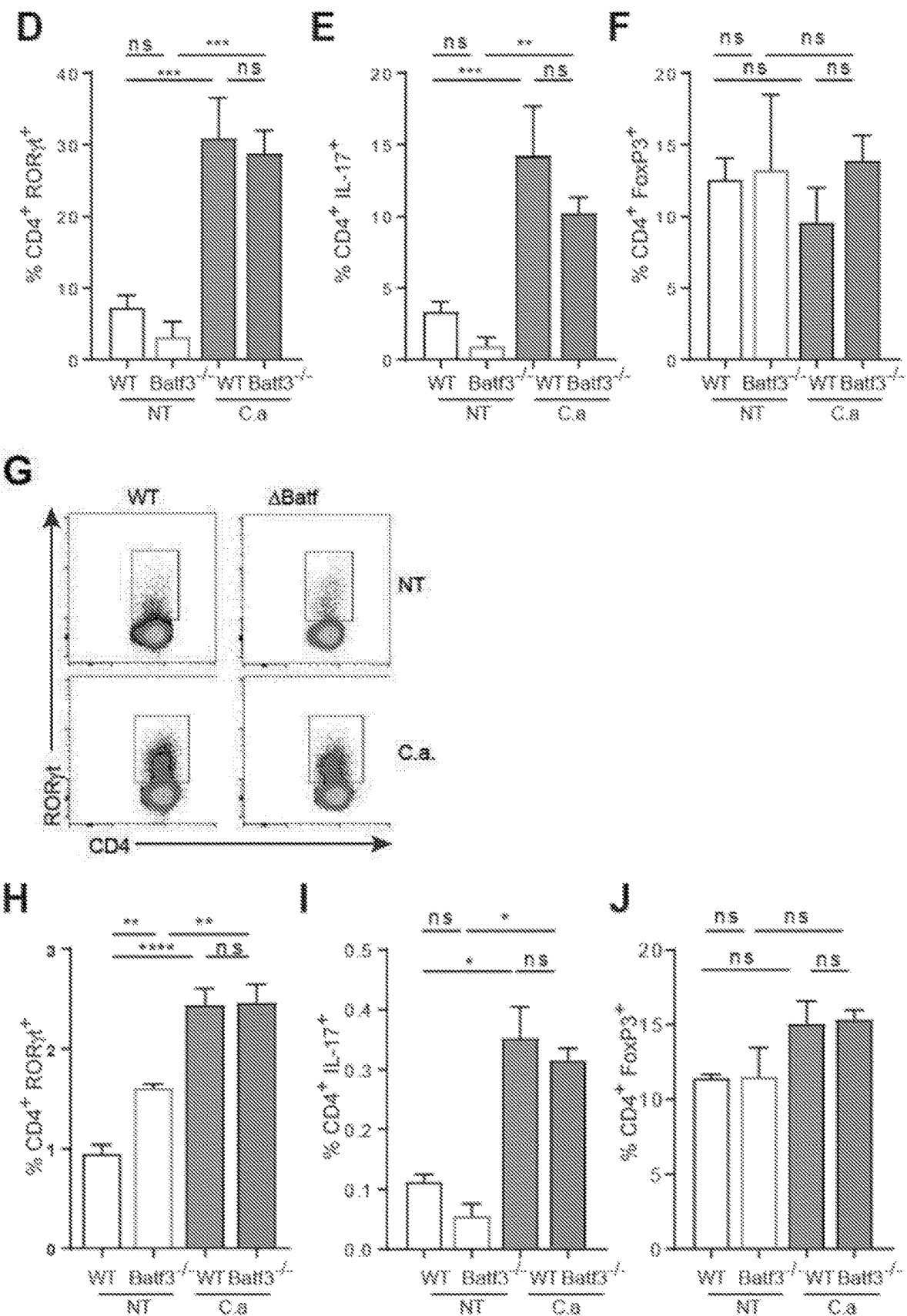
Figure 14:
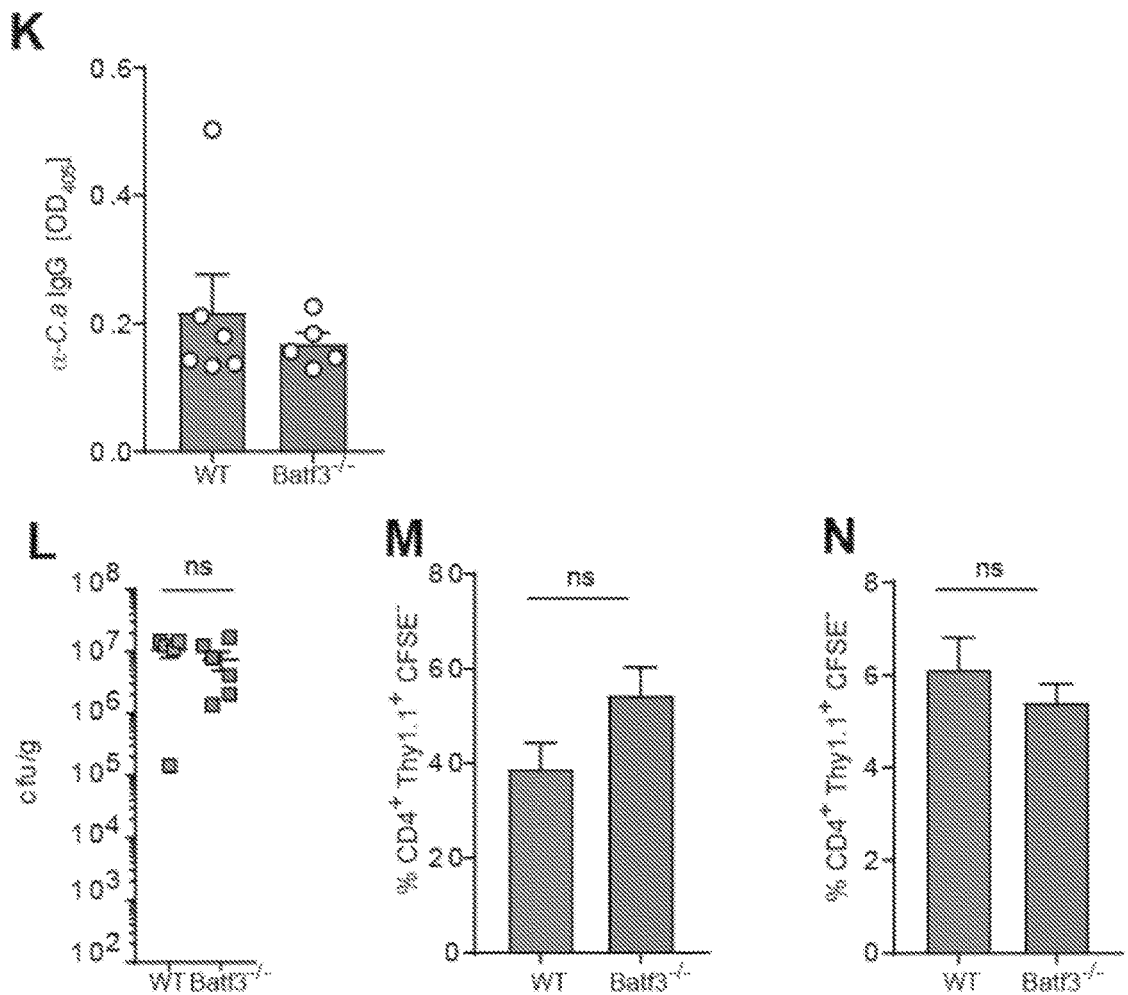

Th17 cells are crucial for the control of fungi at other gastrointestinal (GI) sites such as the oral cavity (Conti et al., 2009, J Exp Med 204(7): 1653-1664; Trautwein-Weidner et al., 2015, PLoS Pathog 11(10): e1005164), while Treg cells suppress fungal infection-related host damage and create an environment that supports fungal persistence (Romani, 2011, Nature reviews. Immunology 11(4): 275-288). Upon colonization with *C. albicans* we observed a strong Th17 response in the colon that was consistent with other studies (FIG. 2A to F, FIG. 9A) (Atarashi et al., 2015, Cell 163(2): 367-380) while the numbers of $Foxp3^+$ Treg cells was not affected (FIG. 9B, C). Thus, we next determined whether specific subsets of intestinal phagocytes are involved in Th17 and $Foxp3^+$ Treg responses to intestinal fungi and compared the frequencies of Th17 cells in colons, small intestines and mesenteric lymph nodes (mLNs) of *C. albicans* colonized. *Candida* colonization induced a consistent increase in Th17 cell frequencies that were not affected by depletion of $CD11b^+$ $CD103^+$ DCs (FIG. 2A-C; FIG. 9C, FIG. 10A) or lack of $CD11b^-$ $CD103^+$ DCs (FIG. 14 C-J). In contrast, a dramatic decrease in the number of Th17 cells was observed upon depletion of $CX3CR1^+$ MNPs in the colon and mLN (FIG. 2D to F, FIG. 10B) but not in the small intestine (FIG. 11A, B,). The observed Th17 induction was independent from segmented filamentous bacteria (SFB) that were absent in our colony (FIG. 4A-C). $Foxp3^+$ Treg cells were not dependent on the presence either phagocytic subset (FIG. 9D and FIG. 10C, 11C, FIG. 14 F, J).

Figure 12:
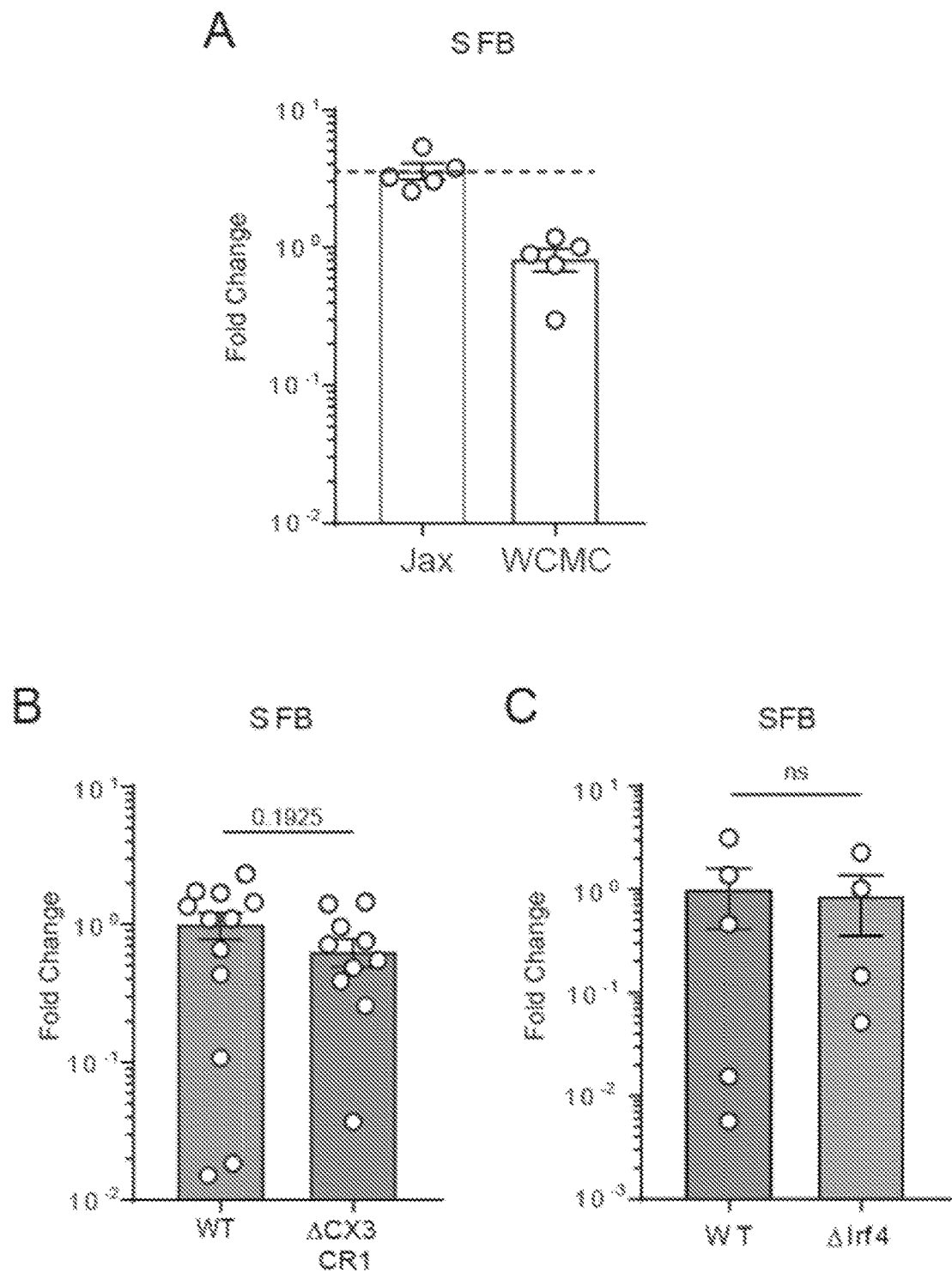
FIG. 12. RT-qPCR assessment of segmented filamentous bacteria (SFB) and *Candida tropicalis*. Relative abundance of SFB in C57BL6 mice purchased from Jaxon (Jax, considered SFB negative) relative to CD11c-cre− mice on a C57BL6 background housed in the Weill Cornell Medical Center (WCMC) facility after normalization to total bacteria (16S) (A). Abundance of SFB in ΔCX3CR1 mice relative to CD11c-cre− littermates after normalization to total bacteria (16S) (B). Abundance of SFB in ΔIrf4 mice relative to CD11c-cre− littermates after normalization to total bacteria (16S) (C). Relative abundance of *C. tropicalis* in C57BL6 mice purchased from Jaxon (Jax, considered SFB negative) relative to mice on a C57BL6 background housed in the Weill Cornell Medical Center (WCMC) facility after normalization to total fungi (18S) (D). Data expressed as mean±SEM, dot represent individual mice. ns: not significant (Student's t test).
Figure 12:
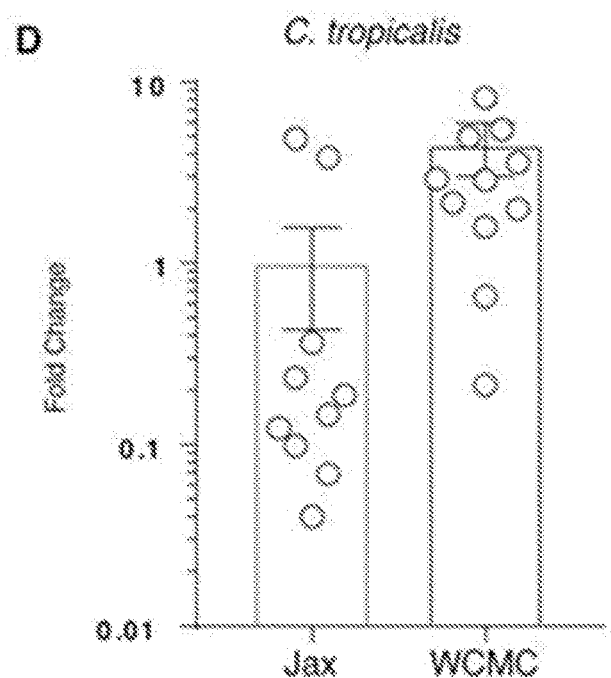
Figure 13:
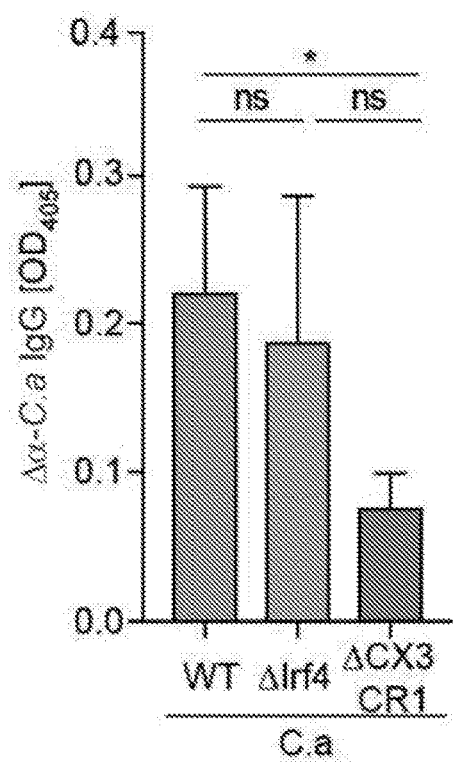
FIG. 13. RT-Induction of systemic IgG responses in ΔIrf4, ΔCX3CR1 and control littermates (WT) fed with *C. albicans*. Mice were fed with 5·108 CFU *C. albicans* (C.a) every 3 days for 10 days and blood was collected at day 10. Dots represent individual mice. *$P<0.05$, $P<0.01$, *$P<0.001$, one-way ANOVA.

Besides Th17 responses, the development of systemic ASCA IgG during intestinal inflammation is another hallmark of adaptive immunity activation in response to intestinal fungi (Standaert-Vitse et al., 2006, Gastroenterology 130(6): 1764-1775; Iliev et al., 2012, Science 336(6086): 1314-1317; Sokol et al., 2013, Gastroenterology 145(3): 591-601 e593). In addition to *S. cerevisiae*, *Candida* can act as an immunogen for ASCA production (Standaert-Vitse et al., 2006, Gastroenterology 130(6): 1764-1775). Thus we assessed whether a specific subset of intestinal phagocytes can also influence the production of systemic IgG antibodies against the commensal fungus *C. tropicalis* (Iliev et al., 2012, Science 336(6086): 1314-1317) commonly found in our colony (FIG. 12) during steady state. We found that CX3CR1$^+$ MNPs depletion reduced IgG-antibody responses against *C. tropicalis* without affecting the response against the commensal bacterial antigen flagellin (FIG. 2G). To assess whether the impaired induction of the antifungal IgG response is dependent on the disruption of the recognition of luminal fungal antigen by CX3CR1$^+$ MNPs we compared the induction of systemic IgG antibodies following *C. albicans* intestinal colonization or *C. albicans* systemic infection. Both approaches led to the generation of systemic anti-*C. albicans* IgG in WT mice (FIG. 2H and FIG. 13). In contrast, depletion of CX3CR1$^+$ MNPs led to a significant decrease of antibody production against *C. albicans* after intestinal colonization (FIG. 2H and FIG. 13) without affecting the antibody production upon systemic infection (FIG. 2H), suggesting that the defect in antifungal antibody production in ΔCX3CR1 mice is specific to the gut. In contrast, neither the depletion of CD11b$^+$ CD103$^+$ DCs nor the lack of CD11b$^-$ CD103$^+$ DCs influenced systemic anti-*Candida* antibody production (FIG. 13, FIG. 14K). Consistent with the decreased antifungal responses, further analysis revealed an overgrowth of *C. albicans* in the intestines of ΔCX3CR1, but not in ΔIrf4 and Batf3$^{-/-}$ mice (FIG. 2I, FIG. 14 L).

Figure 15:
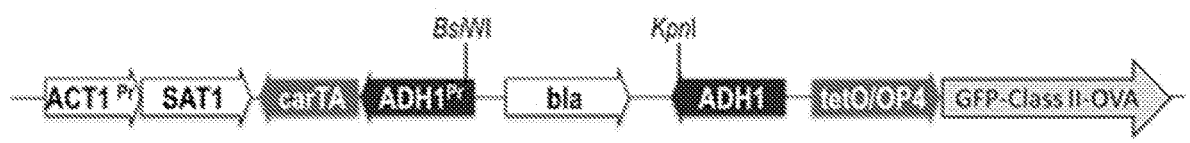
FIG. 15. Construct for the generation of *Candida albicans* strains expressing GFP-OVA Class II epitope fusion (C.a-OVA). The *C. albicans*-adapted reverse trans activator activates the expression of GFP/OVA Class II fusions via the tetO/OP4 promoter. Integration takes place at the ADH1 region of the genome via digestion with BsiWI and KpnI and selection is done on nursothricine (SAT) plates.
Figure 16:
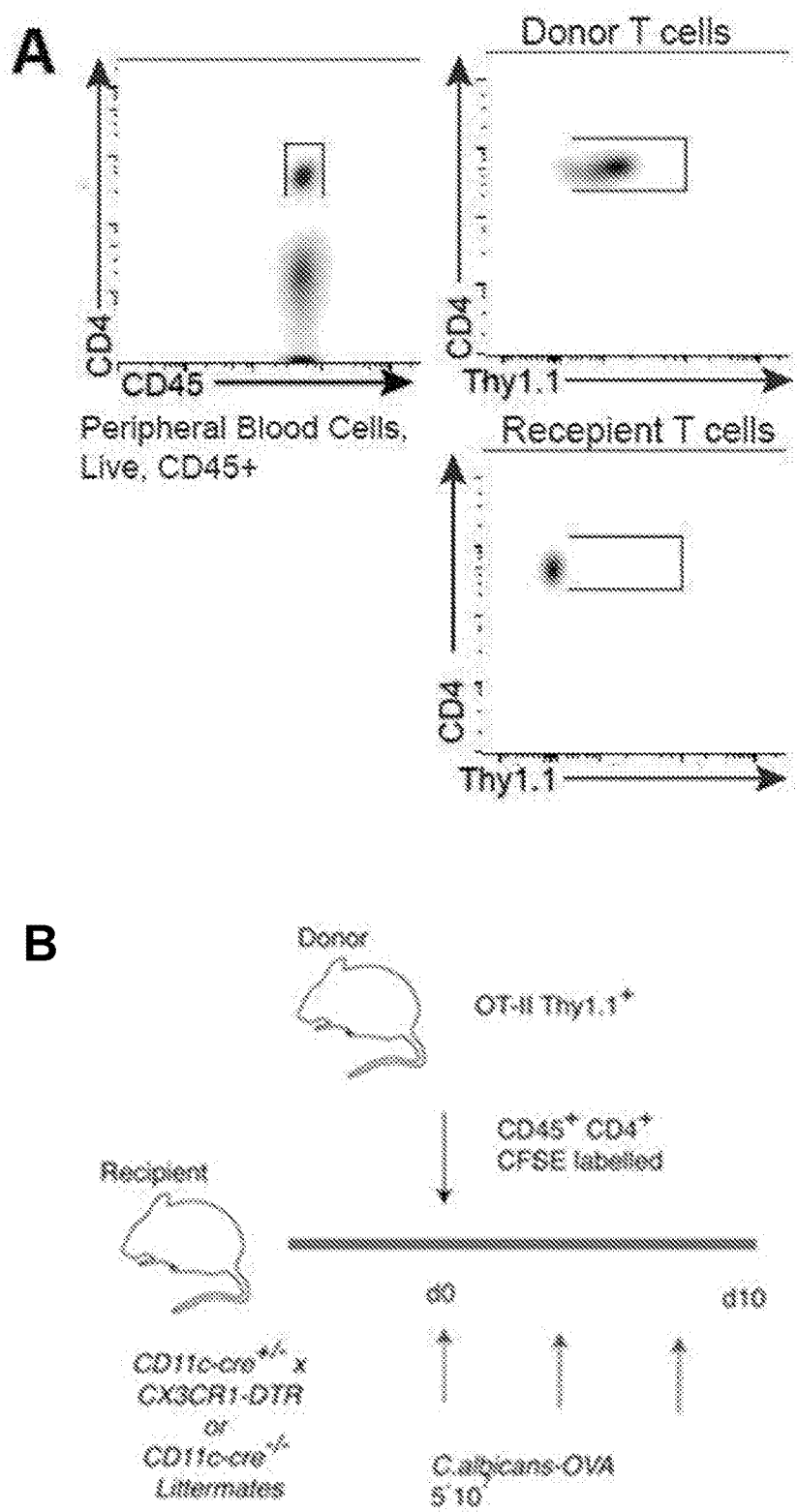
FIG. 16. (A) Characterization of antigen specific responses towards C.a-OVA. Detection of CD4+ Thy1.1+ OT-II donor cells in recipient mice. (B) Mice were transferred with purified CD4+ Thy1.1+ OT-II cells, fed *C. albicans*-OVA and sacrificed at day 10. (C) CD4+ Thy 1.1+ OT-II cells proliferation and RORγ expression in the colon (left) and mLNs (right) of control mice (not treated, NT) or mice fed with *C. albicans*-OVA. (D) Quantification of CD4+ Thy 1.1+ OT-II cells proliferation in the colon of ΔCX3CR1 mice or wild type littermates. (E) CD4+ Thy 1.1+ OT-II cells proliferation in the mLN of ΔCX3CR1 mice or wild type littermates. (F) Antigen specific Th17 responses in the colon of ΔCX3CR1 mice or WT mice. (G, H) ΔSYK mice and controls were transferred with CD4+ Thy 1.1+ OT-II cells, fed *C. albicans*-OVA and sacrificed at day 10. CD4+ Thy 1.1+ OT-II cells proliferation in colon (G) and mLNs (H). Data expressed as mean±SEM of individual mice, representative of three independent experiments.
Figure 16:
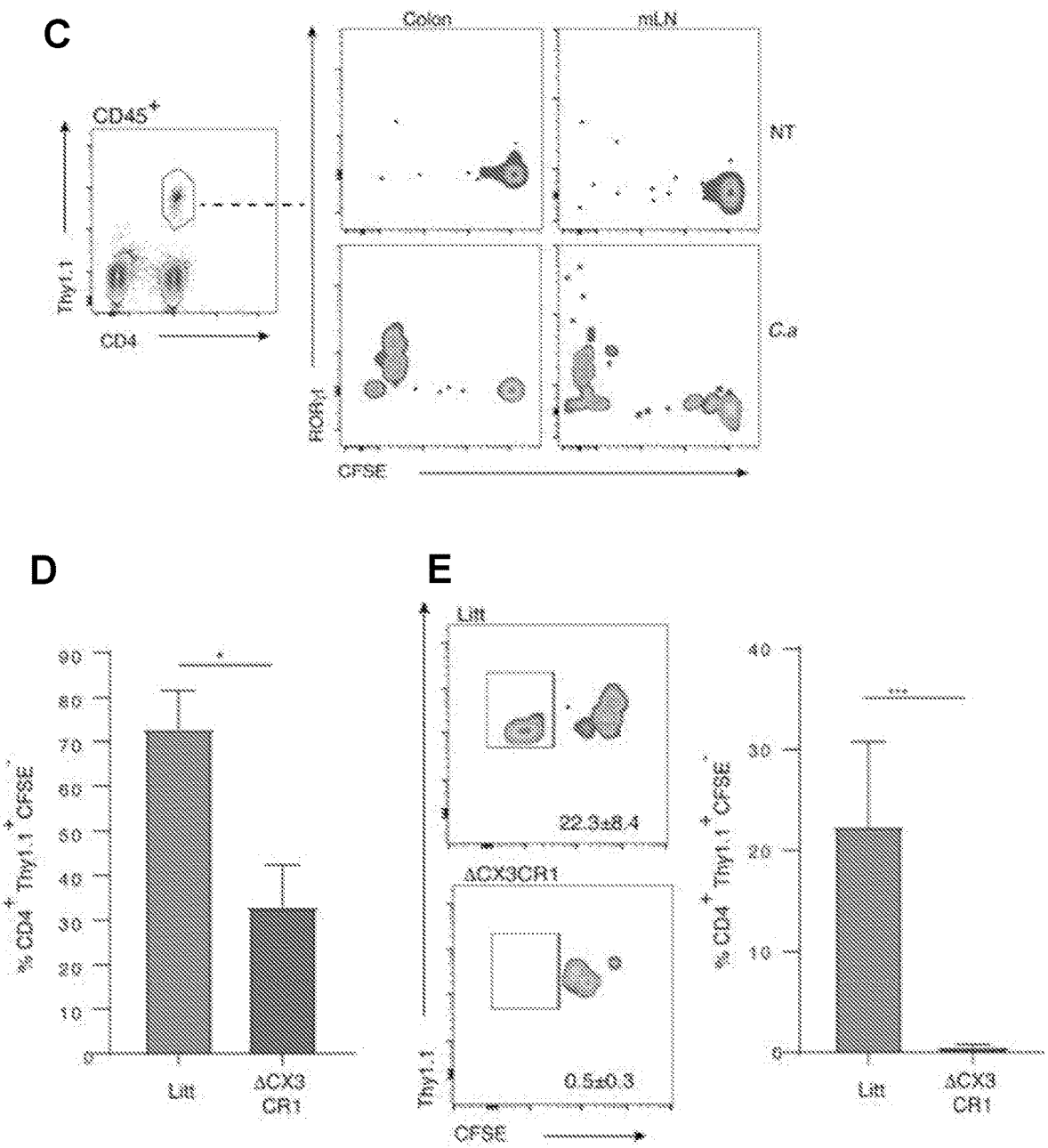
Figure 16:
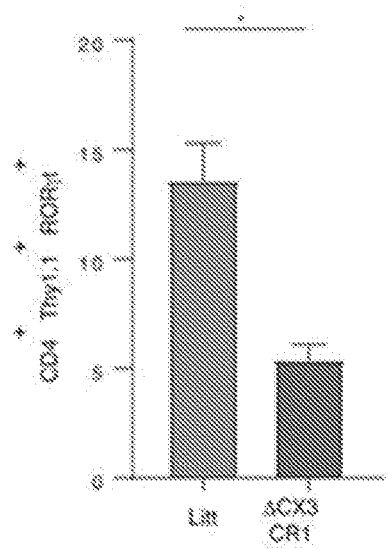
Figure 16:
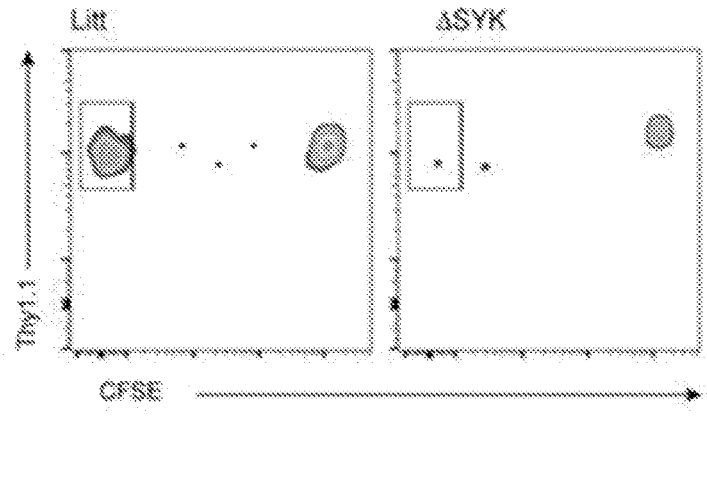
Figure 16:
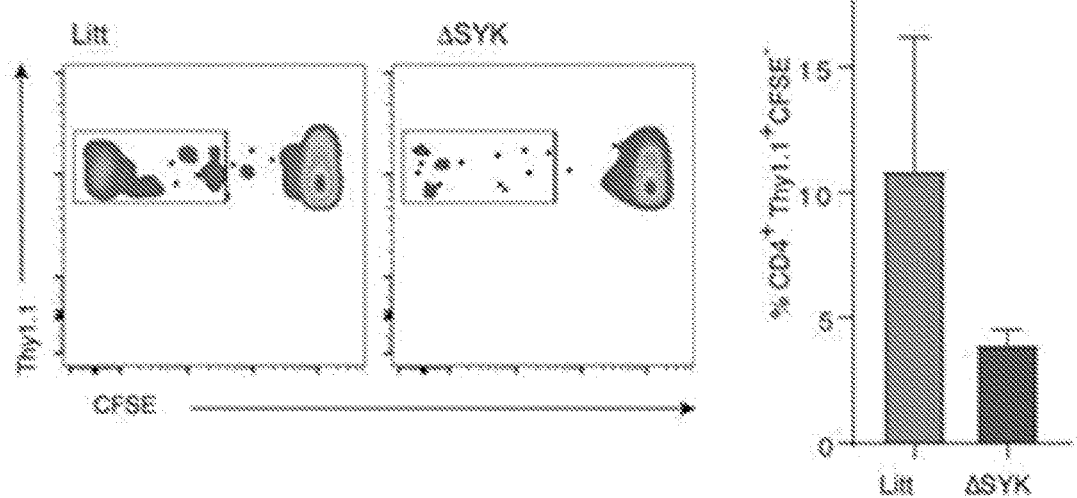

To further assess the role of CX3CR1$^+$ MNPs in the induction of responses to antigens delivered by intestinal fungi, we fed ΔCX3CR1 mice and control littermates a recombinant *C. albicans* strain expressing a model MHC-II-restricted OT-II peptide (C.a-OVA, FIG. 15) and adoptively transferred mice with CFSE-labelled CD4$^+$ Thy1.1$^+$ OT-II cell (FIG. 16B-C). We found that CX3CR1$^+$ MNPs depletion lead to decreased antigen specific proliferation of Th17 cells in response to *C. albicans* in both the colon and in the mLN (FIG. 2 J-K; FIG. 16D-F). CX3CR1$^+$ MNPs might either directly transport fungal antigens to the mLNs for T cell priming or pass the antigens to other population of migratory phagocytes, although both scenarios are possible (Diehl et al., 2013, Nature 494(7435): 116-120; Mazzini et al., 2014, Immunity 40(2): 248-261). Nevertheless, those data demonstrate that CX3CR1$^+$ MNPs play an important role in the induction of Th17 and antibody responses to intestinal fungi, while CD11b$^+$ CD103$^+$ DCs and CD11b$^-$ CD103$^+$ DCs are not crucial.

Figure 17:
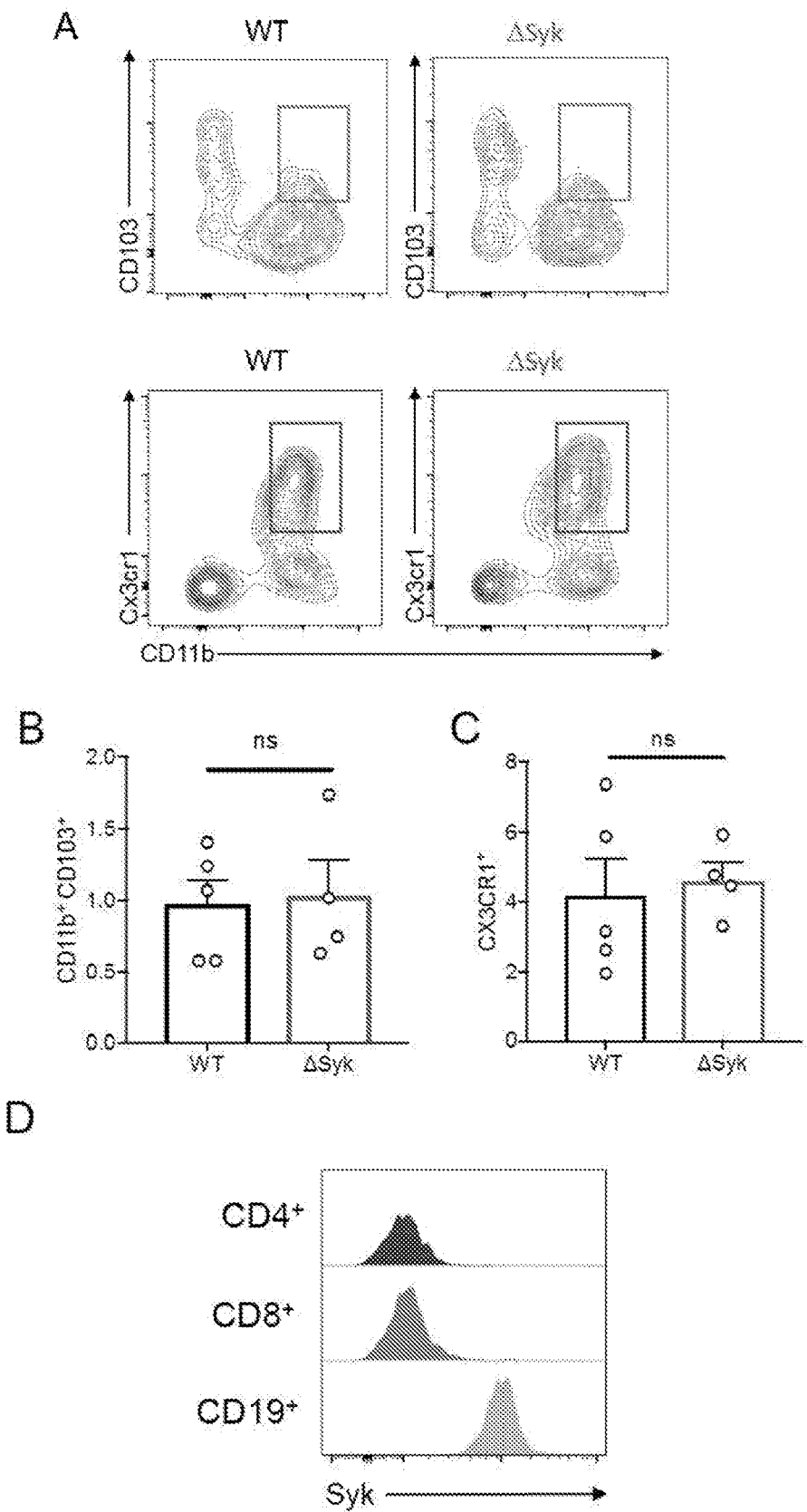
FIG. 17. Specific depletion of Syk in CX3CR1+ MNPs Representative flow cytometry plot of the colonic, Lin− CD45+ MHC-II$^{30}$CD11c+ lymphocytes in ΔSyk mice (Cx3cr1-cre/ERT2+/− Syk$^{fl/fl}$ mice) mice or wild type (Cd11c-cre−/− Irf4$^{fl/fl}$ mice) littermates (A). Quantification of Lin− CD45+ MHC-II+ CD11c+ CD11b+ CX3CR1+ cells (B) and of CD11b+ CD103+ DCs (C) among CD45+ cells. Syk is highly expressed among B cells but not among CD4+ T cells, CD8+ T cells CD4+ T cell, CD8+ T cells, representative flow cytometry plot of Syk expression by colonic CD4+ T cell, CD8+ T cells and CD19+ B cells in C57BL6 WT mice (D). Representative flow cytometry plot of Syk expression among CD11b+ CD103+ DCs, CD11b+ CX3CR1+ MNPs, CD4+ T cells, CD8+ T cells and CD19+ B in ΔSyk mice (Cx3cr1-cre/ERT2+/− Syk$^{fl/fl}$ mice) mice or wild type (Cd11c-cre−/− Irf4$^{fl/fl}$ mice) littermates. Syk expression was reduced upon Tamoxifen treatment in CD11b+ CX3CR1+ MNPs but not in CD19+ B cells, the other high Syk expressing cell type, confirming the selectivity of Syk depletion (E). Data expressed as mean±SEM of individual mice, representative of two independent experiments FIG. 18. Quantification of Th17 and Treg cells in the intestine of ΔSyk mice following *C. albicans* colonization. Quantification of RORγt+ Th17 (A) and FoxP3+ Treg cells (B) among the CD4+ T cells in the colon of ΔSyk mice or wild type littermates. Quantification of RORγt+ Th17 (C) and FoxP3+ Treg cells (D) among the CD4+ T cells in the mLN of ΔSyk mice or wild type littermates. Data expressed as mean±SEM of individual mice, representative of two independent experiments.
Figure 17:
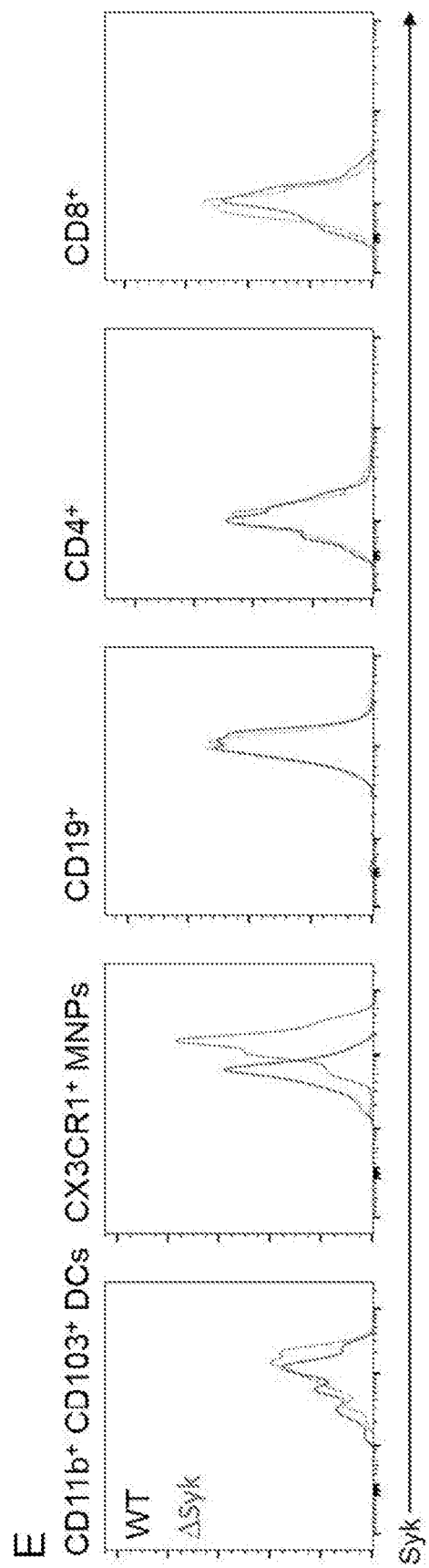
Figure 18:
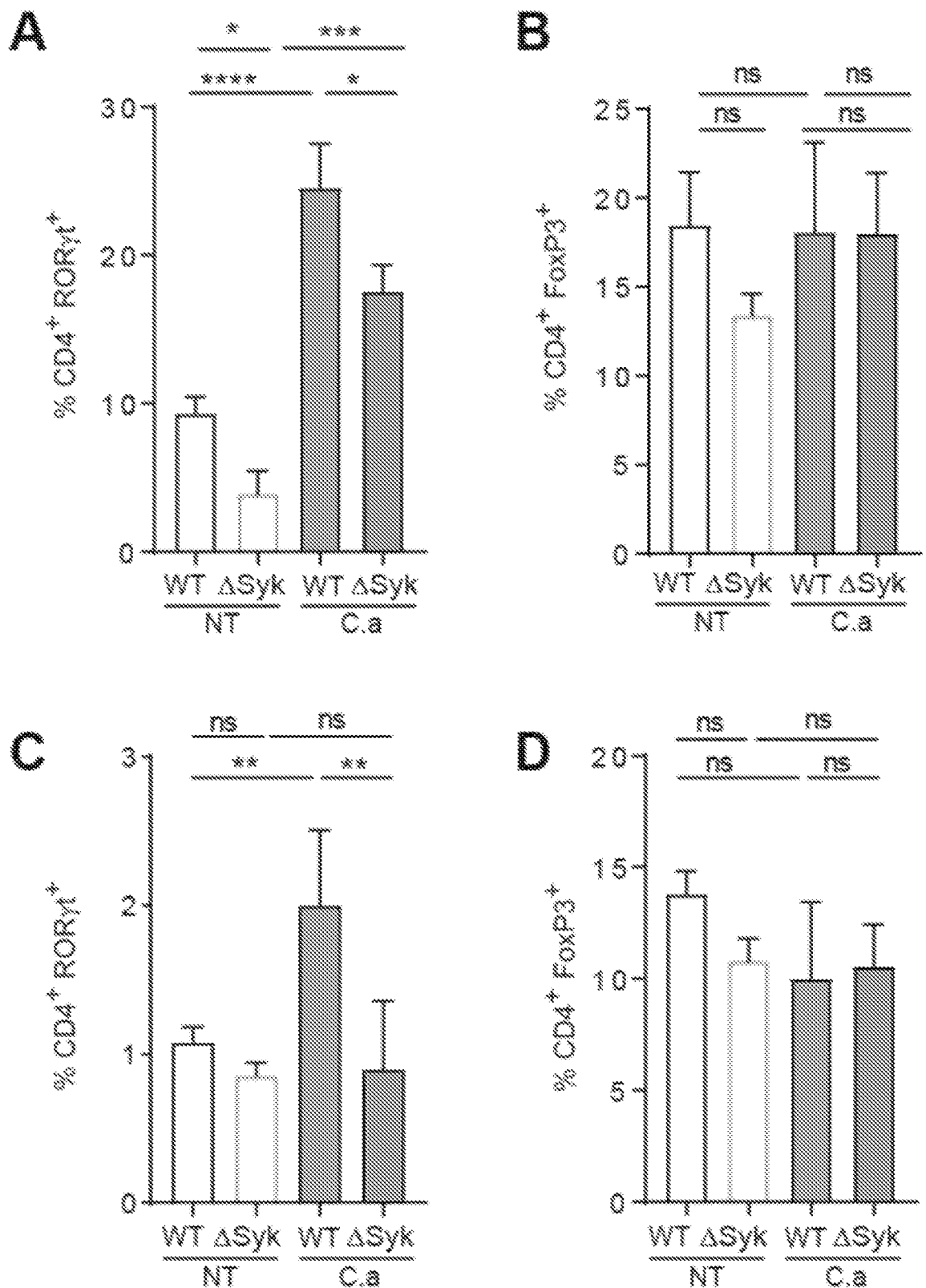

Spleen tyrosine kinase (Syk) is a primary signal transduction molecule acting downstream of several CLRs (FIG. 6). Syk expression is high in CX3CR1$^+$ MNPs but not on CD103$^+$ DCs, (FIG. 1B, D, FIG. 7B). We thus generated ΔSyk CX3CR1 mice (Syk$^{fl/fl}$×Cx3cr1-cre/ERT2$^{+/-}$) allowing to achieve selective Syk deletion in CX3CR1$^+$ cells without affecting the total numbers of CX3CR1$^+$ MNPs or CD11b$^+$ CD103$^+$ DCs (FIG. 17A-C). Consistently, we observed fungal outgrowth but impaired Th17 and antifungal antibody responses to intestinal *Candida* colonization (FIG. 2 L-O, FIGS. 16F and 18), suggesting that intact CLR signaling in CX3CR1$^+$ cells is required to control fungal colonization and to induce effective adaptive immunity to fungi in the gut.

Figure 3:
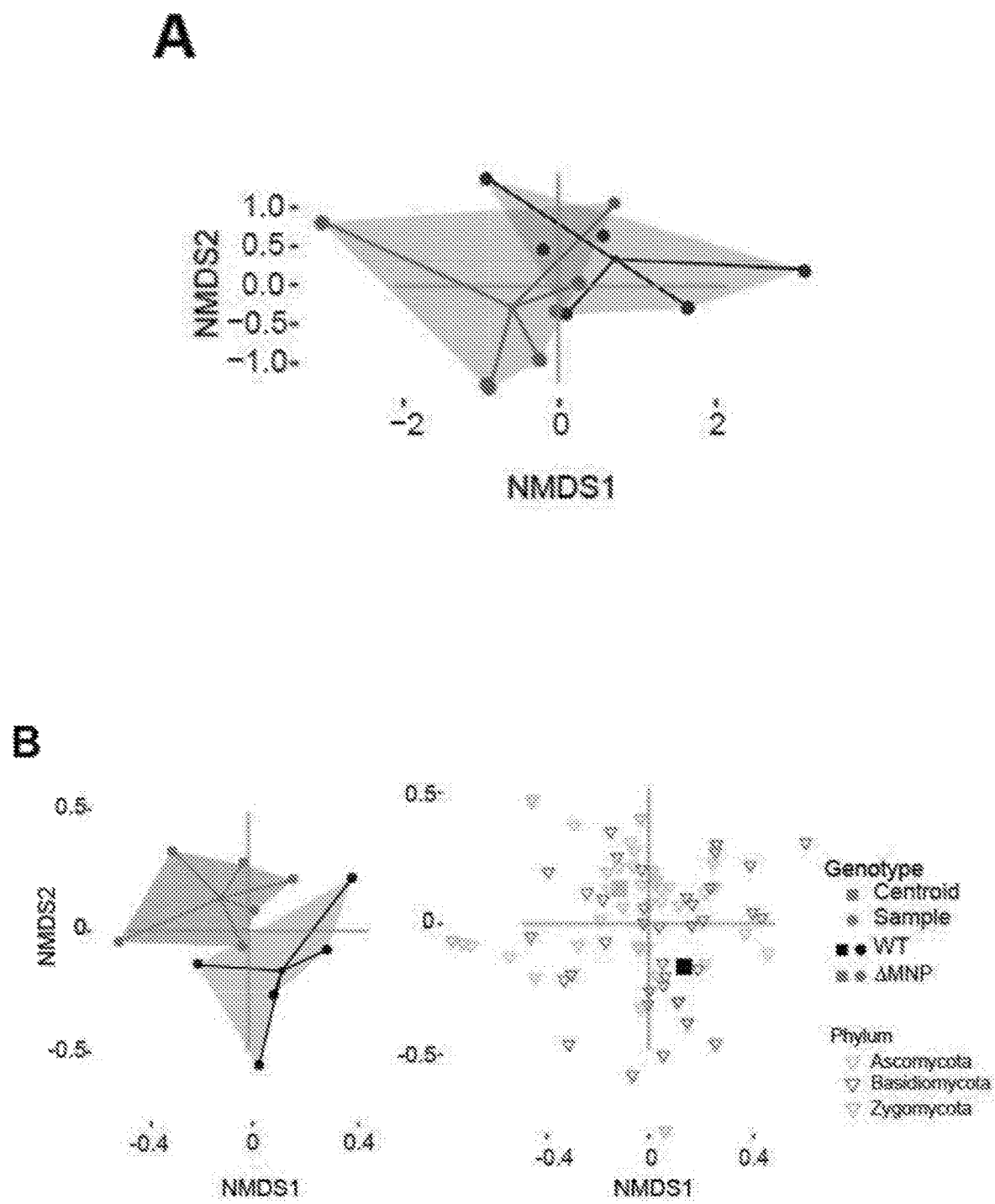
FIG. 3. Depletion of CX3CR1+ MNP affects the fecal mycobiota and results in exacerbated intestinal disease. Feces from ΔCX3CR1 or WT littermates mice were collected 7 days after administration of the first DT dose. NMDS plot of distance ordination based on Bray-Curtis dissimilarities in the colon for bacteria (A), fungi (B, left panel) and specific fungal phyla (B, right panel). Alpha diversity as computed using the Simpson diversity index among bacteria (C, left panel) and fungi (C, right panel). Simpson Diversity index among the Ascomycota (D, left panel) and Basidiomycota (D, right panel) phyla. DSS colitis was induced in ΔCX3CR1 or control (WT) littermates following short term treatment with fluconazole (Fl) or no treatment (Nt), and body weight change (E) and neutrophil infiltration (CD45⁺ CD11b⁺ Gr-1$^{high}$) in the colonic LP (F) were assessed. Representative hematoxylin and eosin (H&E) staining of colon tissue from untreated (NT, top) and fluconazole-treated (Fl, bottom) ΔCX3CR1 or WT littermates mice (G). DSS colitis was induced in ΔCX3CR1 or control (WT) littermates fed with *C. tropicalis* (C.t) and body weight change (H) and colon length (I) were measured. *C. tropicalis* was quantified by SDB plating of faecal material and expressed as cfu/g (J). Systemic IgG responses against *C. tropicalis* were assessed by ELISA (K). Dots represent individual mice. *P<0.05, P<0.01, *P<0.001 (Mann Whitney Test (I, J, K), two-way ANOVA (E, H)).
Figure 3:
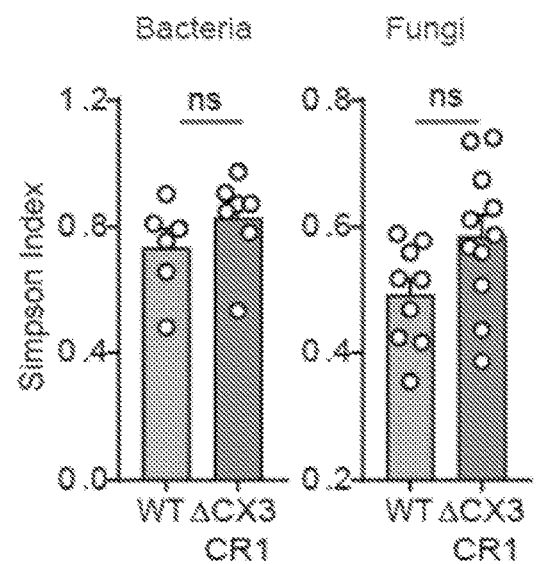
Figure 3:
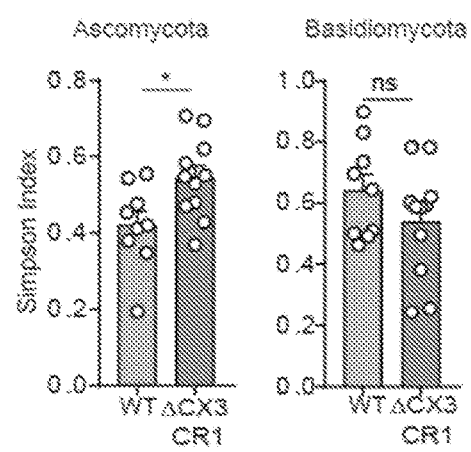
Figure 3:
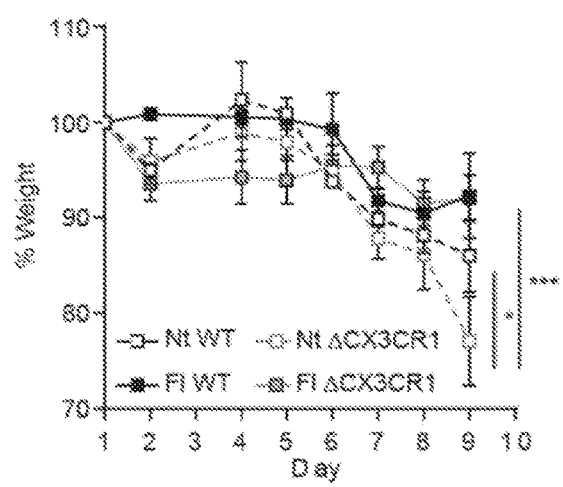
Figure 3:
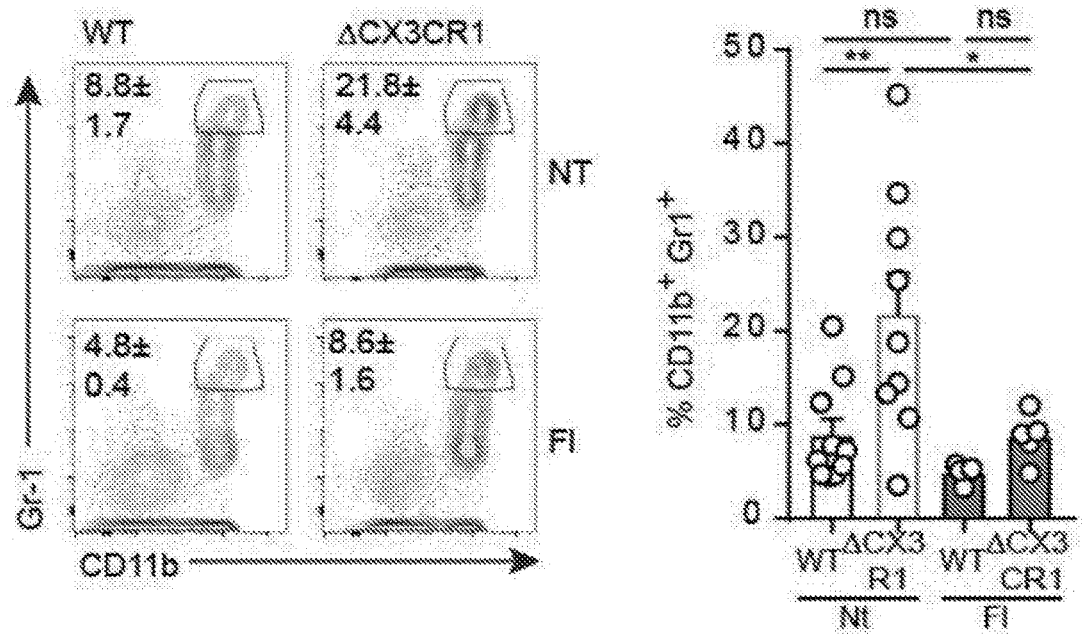
Figure 3:
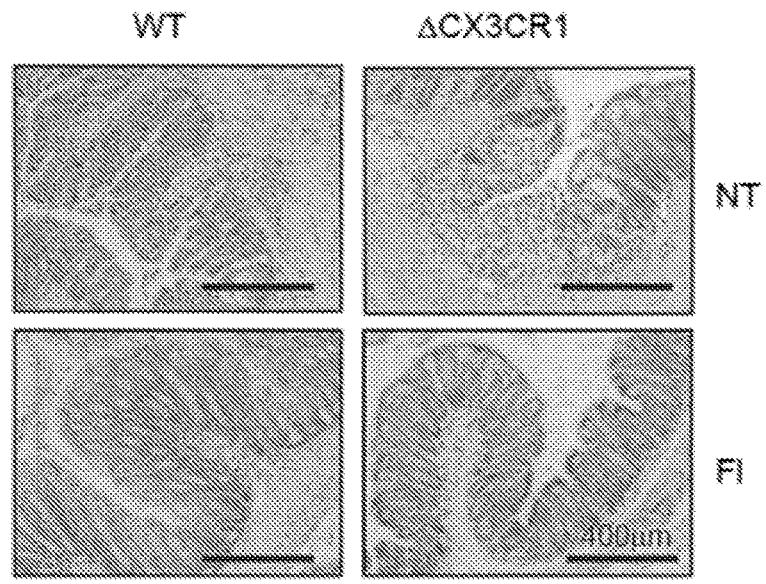
Figure 3:
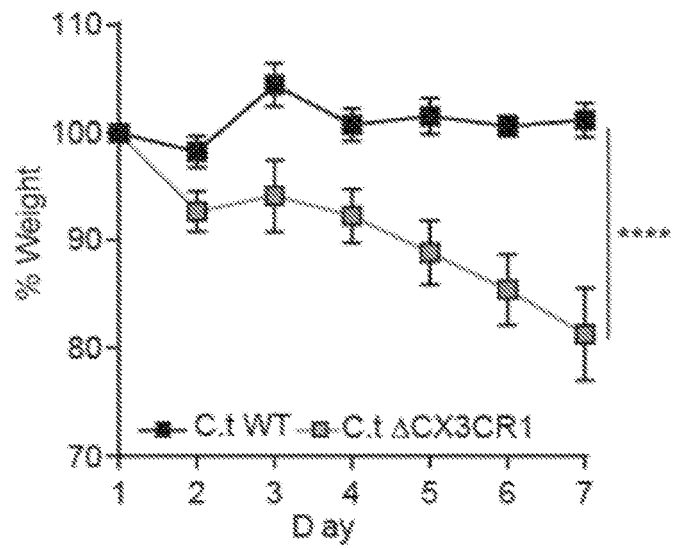
Figure 3:
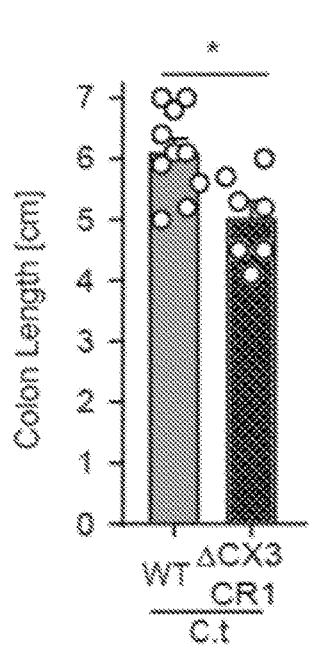
Figure 3:
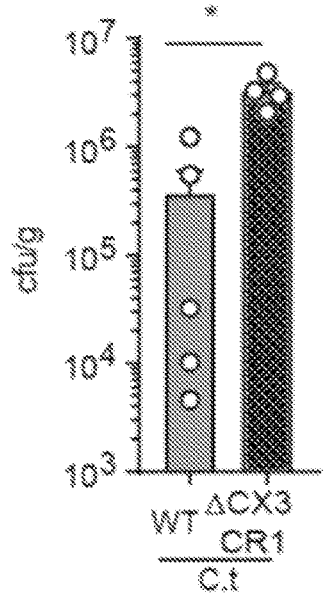
Figure 3:
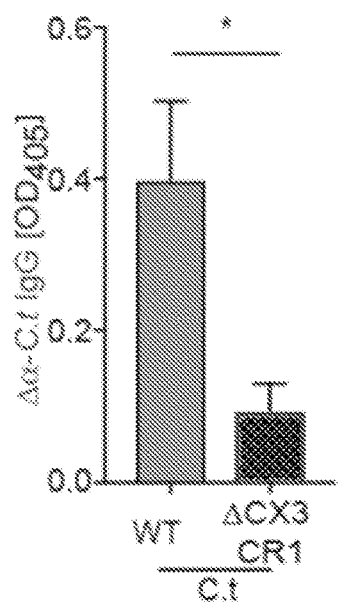
Figure 19:
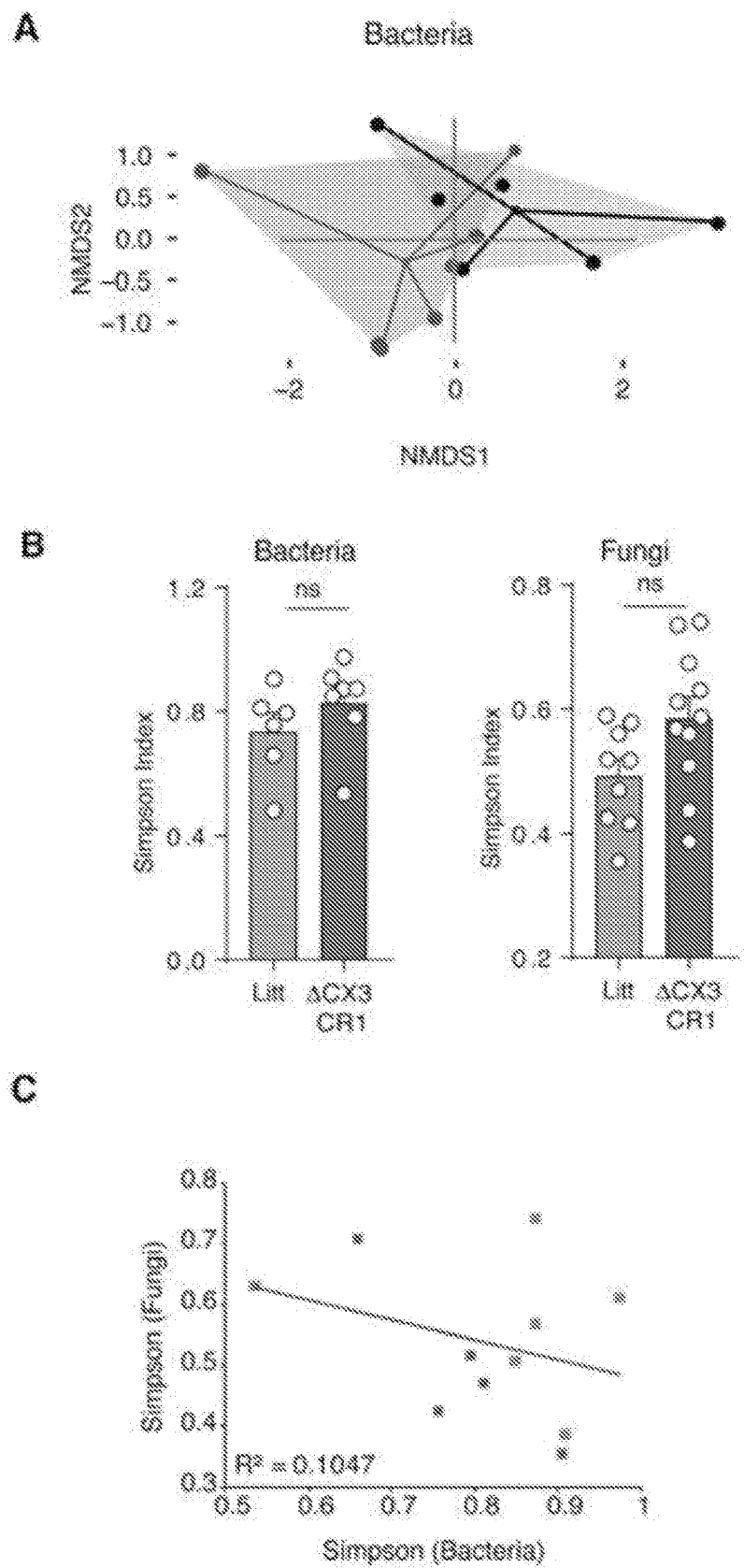
FIG. 19. Characterization of the fungal communities in the feces following CX3CR1+ MNPs depletion. Feces from ΔCX3CR1 or WT littermates mice were collected 7 days after administration of the first DT dose. (A) NMDS plot of distance ordination based on Bray-Curtis dissimilarities in the colon for bacterial OTUs. (B) Alpha diversity as computed using the Simpson diversity index among bacteria (left panel) and fungi (right panel). (C) Correlation between Simpson Diversity in the fungal community (left) or in the Ascomycota phylum (right) with the alpha diversity in the bacterial community. Of note, the increased diversity of the fungal community was independent from bacterial diversity. (D) Simpson diversity in the two major bacterial phyla (Firmicutes and Bacteroidetes). (E) Shannon diversity index among total bacteria, Firmicutes, Bacteroidetes, total fungi, Ascomycota and Basidiomycota. Statistic: data are pooled from two independent experiments, graphs show mean+/− SEM, each circle denotes one mouse. Data expressed as mean±SEM (Mann-Whitney Test).
Figure 19:
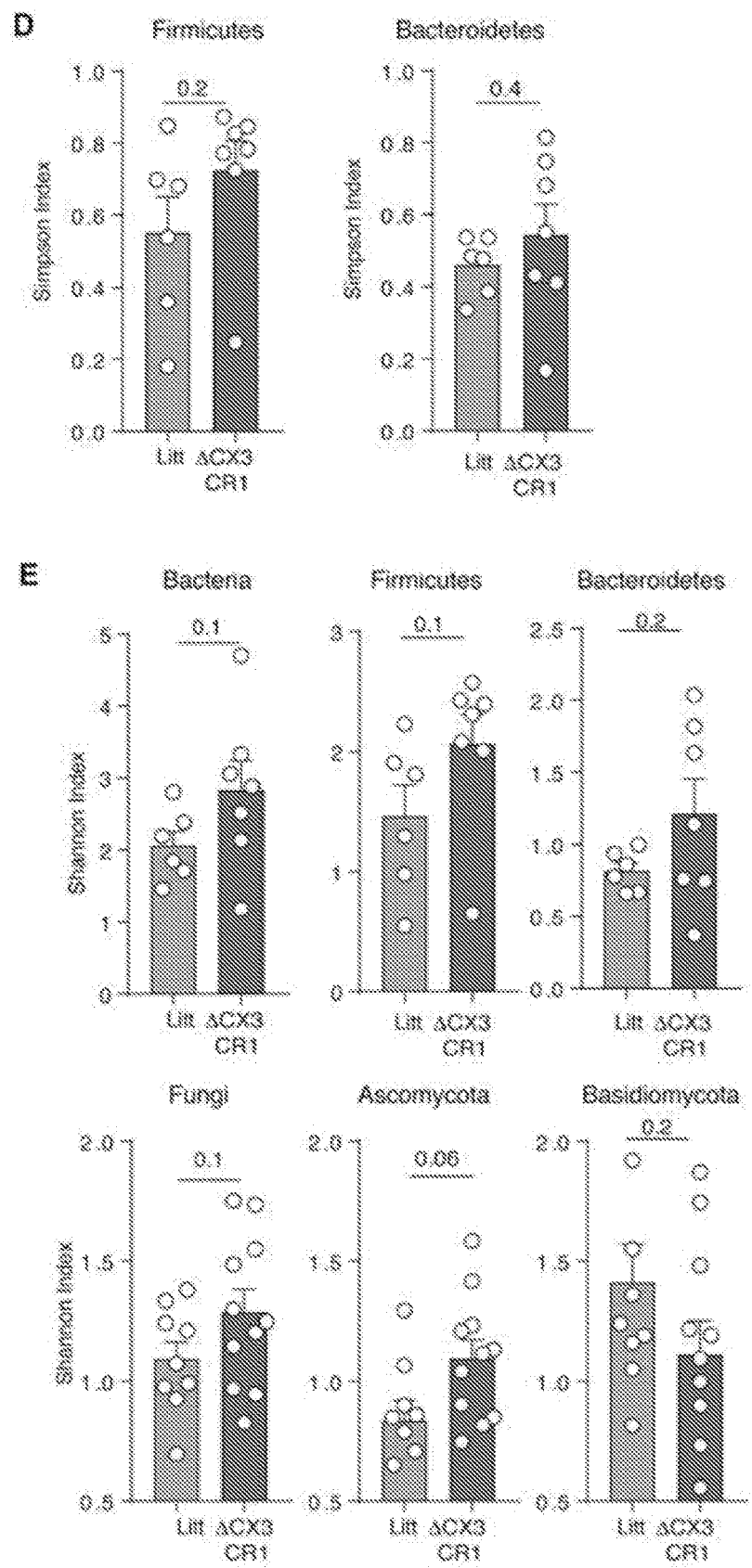
Figure 20:
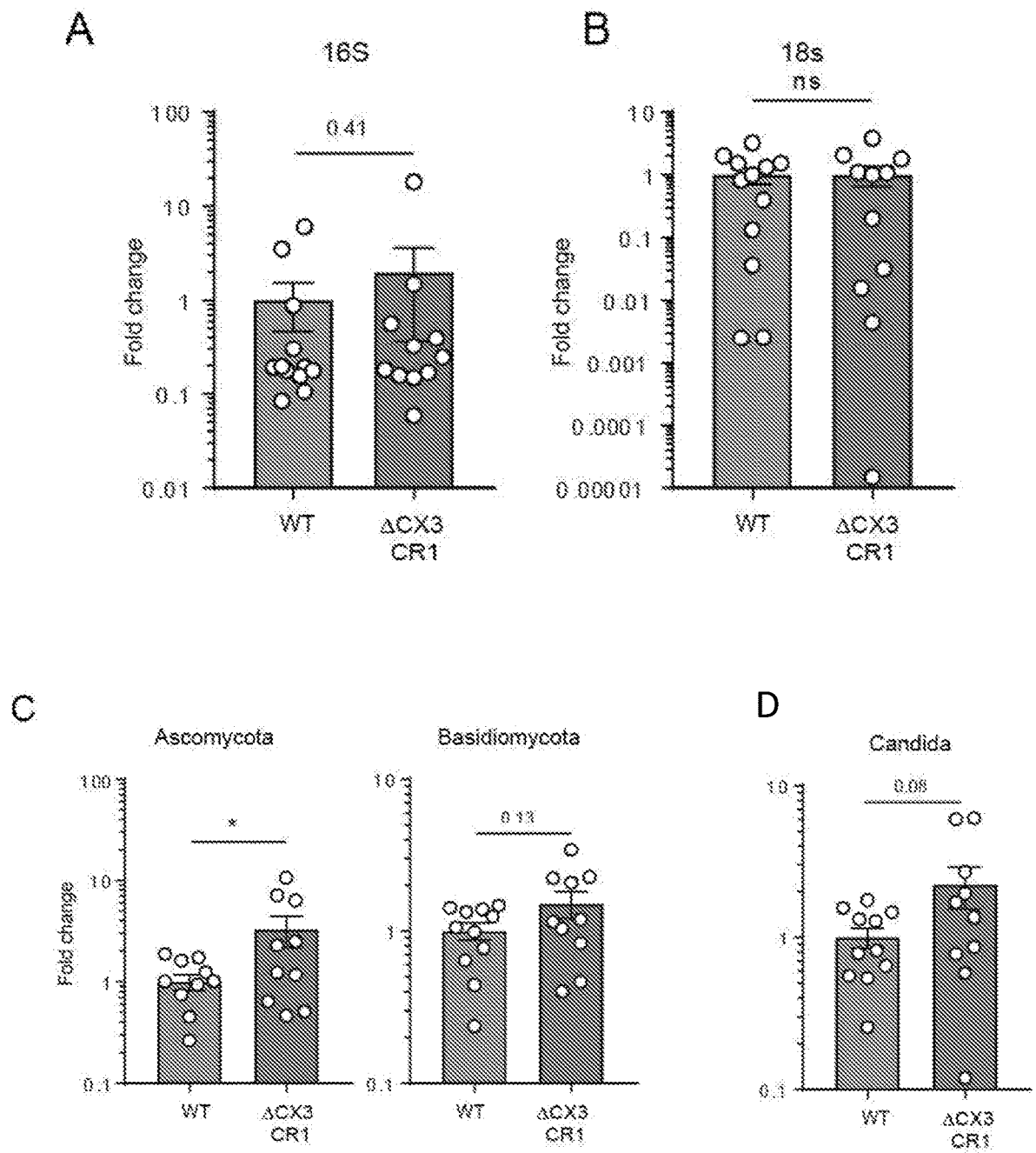
FIG. 20. RT-qPCR assessment of the microbiota following CX3CR1+ MNPs depletion. Abundance of bacteria as determined by 16S qPCR in mice following depletion of CX3CR1+ MNPs; $2^{\Delta CT}$ relative to 16S abundance in WT (CD11c-cre− littermates) (A). Relative abundance of fungi (18S) in ΔCX3CR1 mice relative to WT mice after normalization to total bacteria (16S) (B). Relative abundance of Ascomycota (C, left panel), Basidiomycota (C, right panel) and *Candida* (D) in ΔCX3CR1 mice relative to WT mice after normalization to total fungi (18S). Data expressed as mean±SEM, dot represent individual mice. Data are representative of two independent experiments with 4-5 mice per experiment. *P<0.05 (Student's t test)
Figure 21:
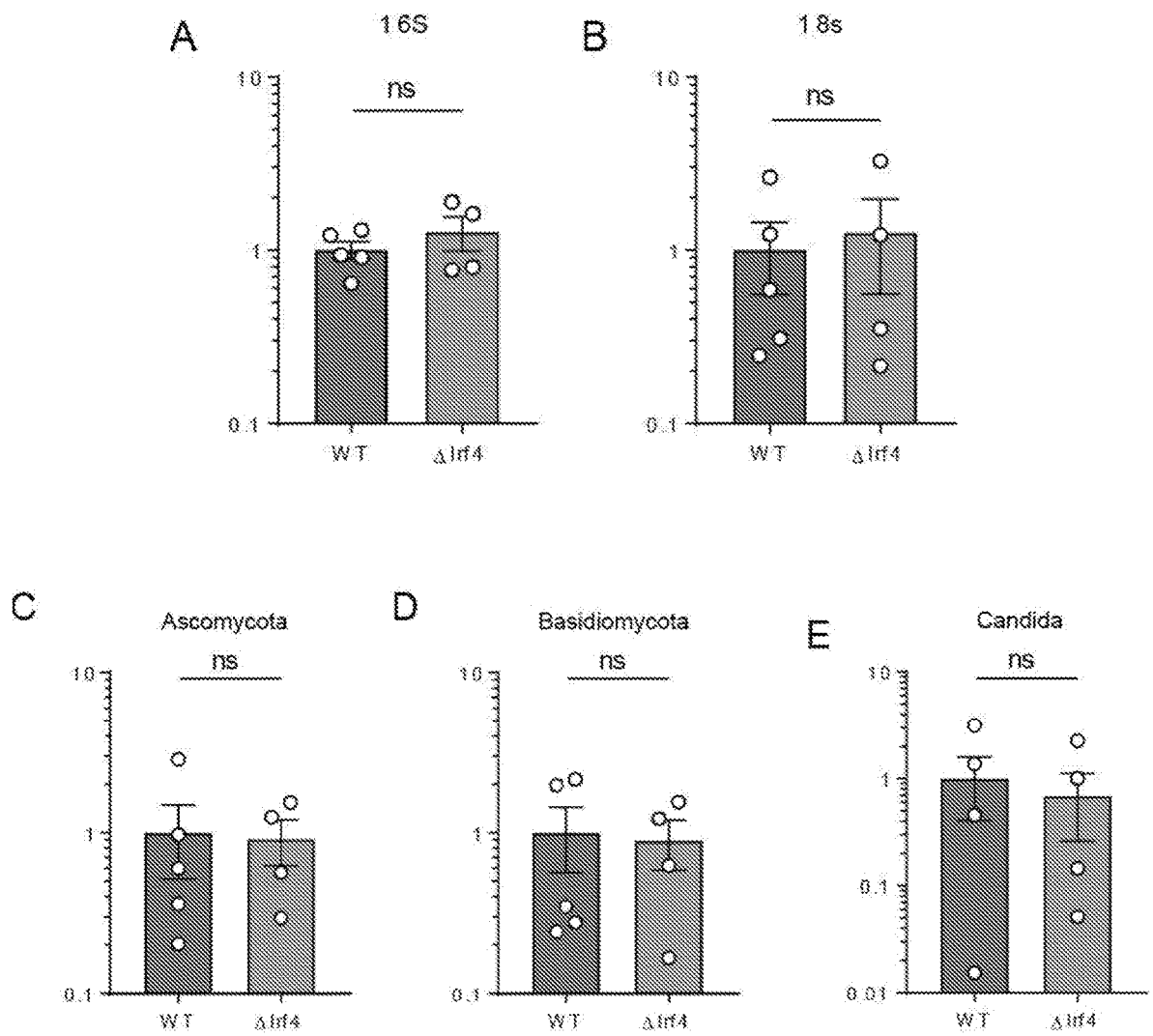
FIG. 21. RT-qPCR assessment of the microbiota in ΔIrf4 mice. Abundance of bacteria as determined by 16S qPCR in ΔIrf4 mice relative to 16S abundance in WT (CD11c-cre− littermates) (A). Relative abundance of fungi (18S) in ΔIrf4 mice relative to WT mice after normalization to total bacteria (16S) (B). Relative abundance of Ascomycota (C), Basidiomycota (D) and *Candida* (E) in ΔIrf4 mice relative to WT mice after normalization to total fungi (18S). Data expressed as mean±SEM, dots represent individual mice. Data are representative of two independent experiments with 4-5 mice per experiment. *P<0.05, ns: not significant (Student's t test).
Figure 22:
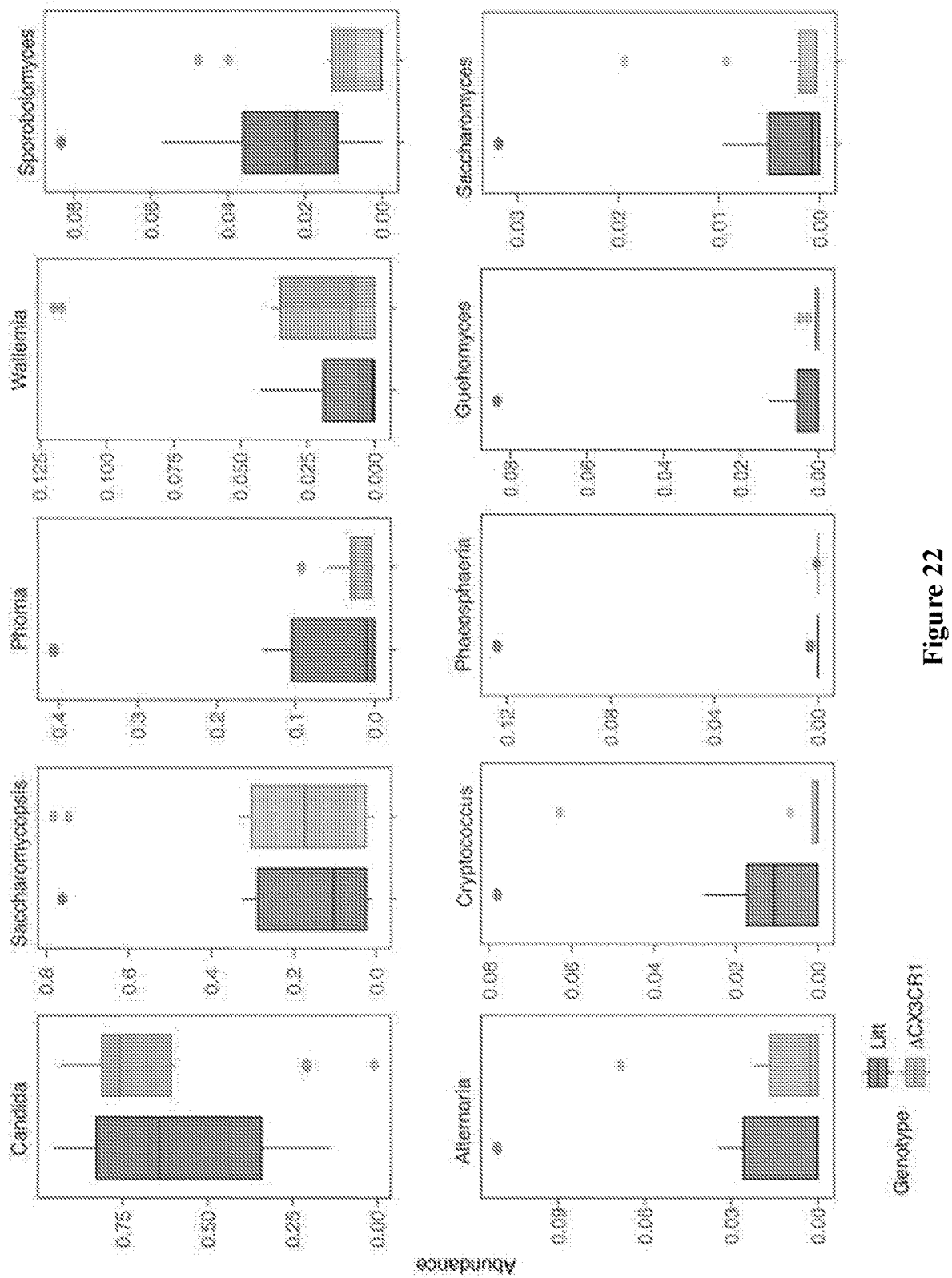
FIG. 22. Relative abundance of the 10 most abundant fungal genera in the feces of ΔCX3CR1 mice or control littermates (WT). Boxplot represent median and lower and upper hinges correspond to the 25th and 75th percentiles. Data are pooled from 2 independent experiments.
Figure 23:
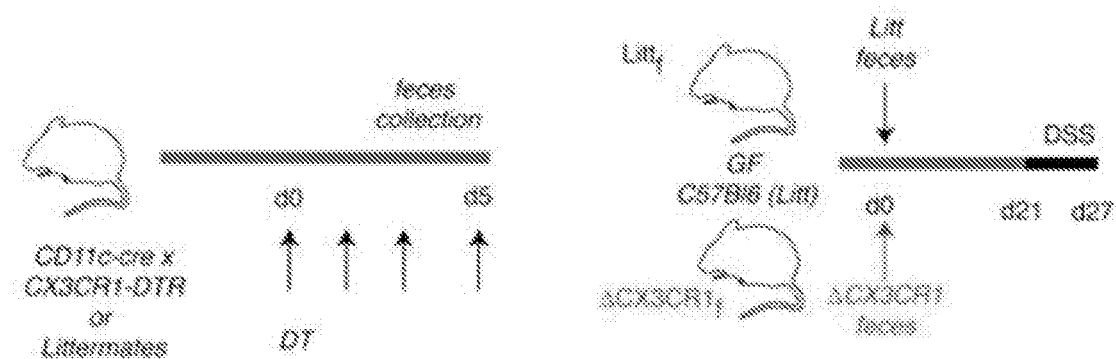
FIG. 23. Impaired antifungal-immunity increases susceptibility of ΔCX3CR1 mice to DSS colitis. (A) Outcome of DSS colitis in germ free (GF) C57BL6 WT mice transferred with feces from ΔCX3CR1 mice or control littermates both treated with diphtheria toxin for 5 days. (B) Weight loss from baseline at day 21, Xaxis shows day after start of DSS treatment. (C) Total 16s DNA in the feces of the recipient mice at day 27 (day of sacrifice). (D) Frequency of colonic Neutrophils (Live, CD45+ CD11b+ Gr1+) among CD45+ Lymphocytes. (E) Frequency of IL-17 producing CD45+ CD4+ cells. (F) Frequency of RORγt+ CD45+ CD4+ T cells. Data expressed as mean±SEM of individual mice (n=4-5), representative of two independent experiments. Statistical analysis: *P<0.05, P<0.01, *P<0.001 (Mann-Whitney Test).
Figure 23:
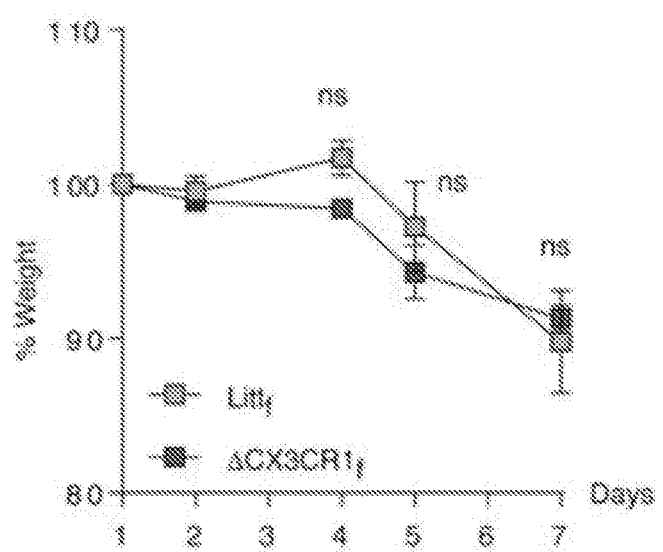
Figure 23:
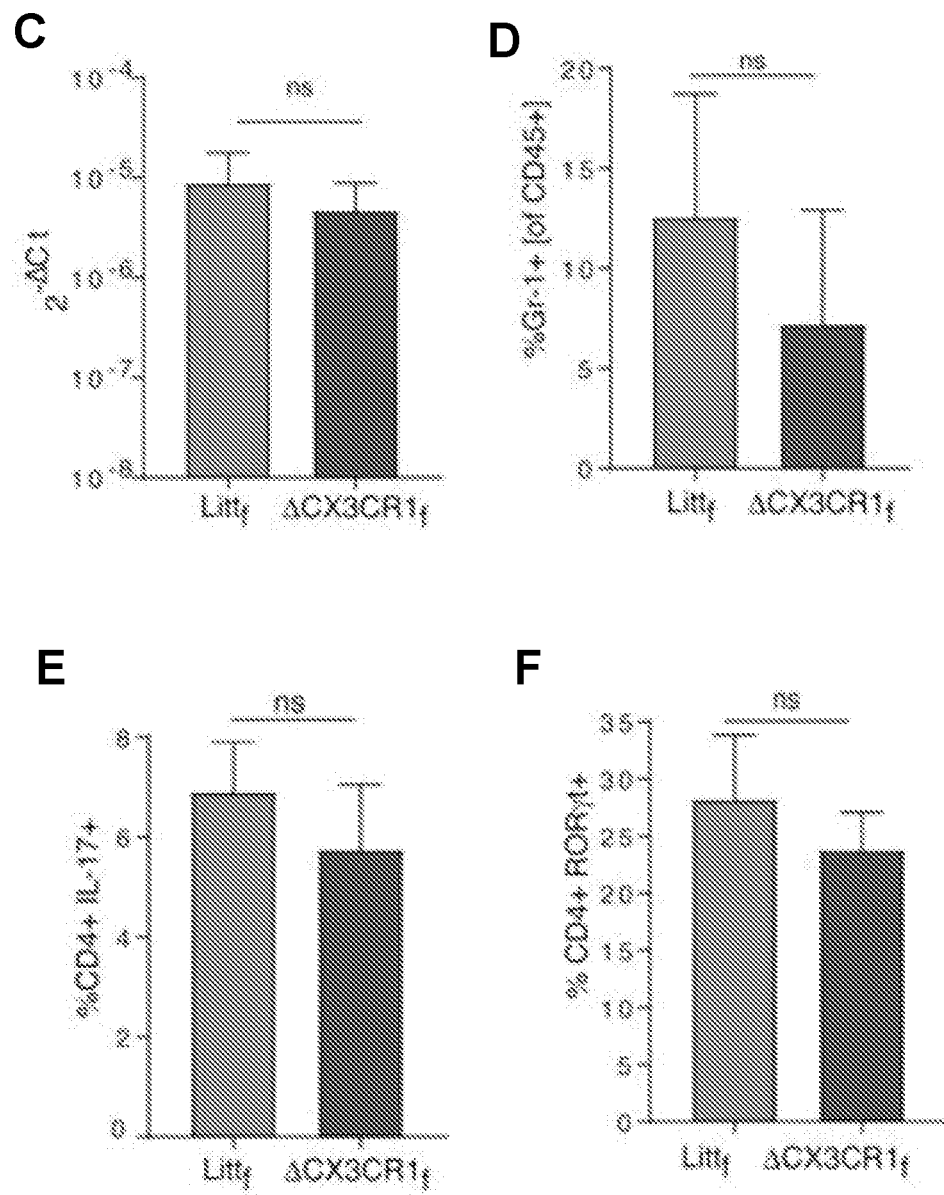
Figure 24:
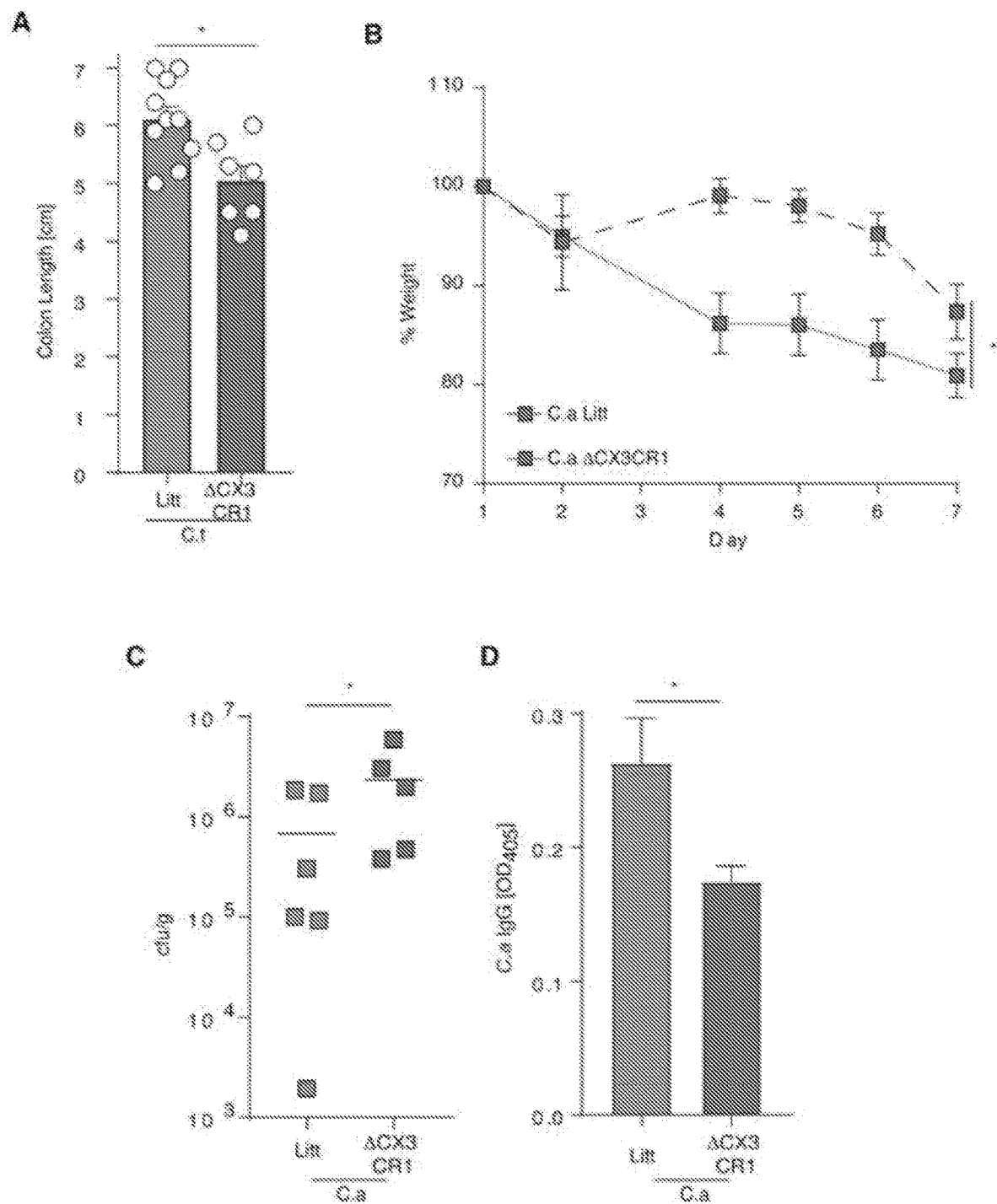
FIG. 24. Depletion of CX3CR1+ MNP results in exacerbated intestinal disease following *C. albicans* colonization. Shortening of the colon in ΔCX3CR1 mice or control littermates with *C. tropicalis* (C.t) after induction of DSS colitis (A). Percent weight loss in ΔCX3CR1 or control (WT) littermates fed with *C. albicans* (C.a) following DSS administration (B). *C. albicans* was quantified by SDB plating of faecal material and expressed as cfu/g (C). Systemic IgG responses against *C. albicans* were assessed by ELISA (D) Dots represent individual mice. *P<0.05. Mann Withney Test (B, C), two-way ANOVA (A).

Having determined that CX3CR1$^+$ MNPs recognize intestinal fungi and control gut antifungal immunity, we next explored whether these cells play a role in shaping the composition of gut fungal communities. Lack of CD11b$^+$ CD103$^+$ that are not necessary for the initiation of an antifungal-response also had no effect on the composition of the fecal mycobiota. To characterize the microbiota upon CX3CR1$^+$ MNPs depletion we used high-throughput ITS1 and 16S sequencing of fungal and bacterial rDNA respectively. Despite their known role in the control of commensal and pathogenic bacteria translocation from the intestinal lumen to the mLNs (Niess et al., 2005, Science 307(5707): 254-258; Medina-Contreras et al., 2005, J Clin Invest 121 (12): 4787-4795; Diehl et al., 2013, Nature 494(7435): 116-120), ablation of CX3CR1$^+$ MNPs did not affect beta and alpha diversity of the intestinal bacterial community (FIGS. 3A and C, FIG. 19A-E, FIG. 20A). In contrast, ablation of CX3CR1$^+$ MNPs altered the fungal community composition of mice as compared to control littermates (FIG. 3B, FIGS. 19A and D, FIG. 20B-D, FIG. 22). CX3CR1$^+$ MNPs depletion also led to an increase in fungal alpha diversity (FIG. 3C, FIG. 20), that was mainly driven by an increased abundance and diversity among the Ascomycota phylum (FIG. 3D, FIGS. 19B and E, FIG. 20). This suggest that CX3CR1$^+$ MNPs play a role in immune surveillance and maintenance of a balanced gut fungal community.

Since fungi are present at highest densities in the colon (They et al., 2012, Science 336(6086): 1314-1317) where fungal colonization induced a strong Th17 response (FIG. 2A-F, FIG. 9A), we focused our further studies on this gastrointestinal site. Thus, we next tested whether ΔCX3CR1 mice are more susceptible to DSS-induced colitis. Consistent with their inability to mount an efficient antifungal response, we found that DSS treatment caused greater body weight loss and inflammatory cells infiltration in the colons of ΔCX3CR1 mice as compared to their littermate controls (FIGS. 3E and G). Fluconazole targets most *Candida* species and other dimorphic fungi, and ameliorates colitis in mice with defects in antifungal immunity when used during the onset of intestinal disease (They et al., 2012, Science 336(6086): 1314-1317; Sokol et al., 2013, Gastroenterology 145(3): 591-601 e593). Since CX3CR1$^+$ MNPs depletion had a strong effect on Ascomycota, we treated ΔCX3CR1 mice with fluconazole. Notably, fluconazole treatment significantly ameliorated intestinal disease in ΔCX3CR1 mice (FIGS. 3E and G, and FIGS. 3F and G). Transfer of ΔCX3CR1 mice mycobiota did not affect the outcome of colitis in germ free mice (FIG. 23A-F), indicating that a dysbiotic mycobiota is not per-se pathogenic if the antifungal immune responses are intact. Further supplementation with *C. tropicalis*, previously shown to affect intestinal conditions in dectin-1 and dectin-3 deficient mice (They et al., 2012, Science 336(6086): 1314-1317; Tang et al., 2015, Cell Host Microbe 18(2): 183-197; Wang et al., 2016, PLoS Pathog 12(6): e1005662), or with *C. albicans*, led to severe wasting disease, colon shortening and overgrowth of *C. tropicalis* in the intestines of ΔCX3CR1 mice without worsening the disease in the littermate controls (FIG. 3H-J, FIGS. 24A and B). Despite the increased disease susceptibility and augmented *Candida* burden, ΔCX3CR1 mice failed to mount a systemic antifungal IgG antibody response (FIG. 3K, FIGS. 24C and D), consistent with the defects in antifungal immunity that we observed during the steady state. These results indicate that CX3CR1$^+$ MNPs play a crucial role in controlling fungal microbiota during intestinal disease.

Figure 25:
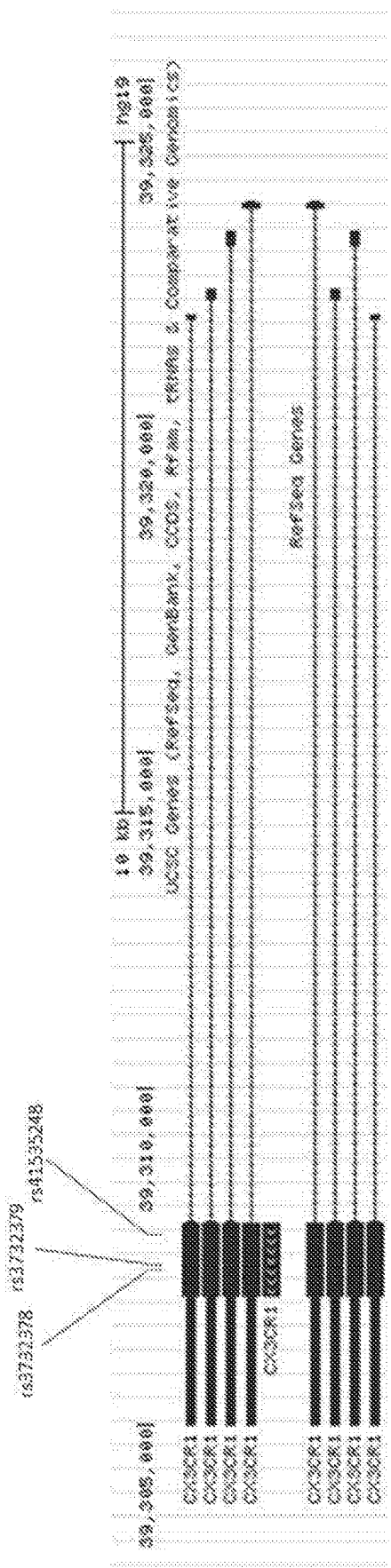
FIG. 25. Map of CX3CR1 gene region and 3 SNPs in the coding region.

Having established a role for CX3CR1+ MNPs in the control of gut fungi during intestinal disease, and finding that CX3CR1+ MNPs were able to intake other species of commensal fungi found in the gut of both humans and mice (FIG. 4A), we explored whether genetic variations of the human CX3CR1 gene affect immunity to fungi in inflammatory bowel disease (IBD). Defects in CX3CR1 have been shown to increase susceptibility of mice and humans to systemic candidiasis but not to vulvovaginal and oral candidiasis (Break et al., 2015, Infect Immun 83(3): 958-965). In contrast, the role of CX3CR1 in the initiation of antifungal responses in the gut has not been addressed. We focused on polymorphisms in the coding region of CX3CR1 gene (FIG. 25) that have been previously associated with human inflammatory diseases such as arteriosclerosis and coronary artery disease (McDermott et al., Circ Res 89(5): 401-407; Moatti et al., 2001, Blood 97(7): 1925-1928; Break et al., 2015, Infect Immun 83(3): 958-965). While none of these polymorphisms were associated with a predisposition to IBD (Table 1), we identified a striking association of CX3CR1 T280M (rs3732378) polymorphism specifically with IgG ASCA positivity in CD patients (FIG. 4B, OR=0.59, logistic regression p=3.73E$^{-03}$).

TABLE 1

Association of missense mutations in CX3CR1 with Crohn's Disease (CD)

| rsI | CH | Position* | FA# | FU$ | OR | L95 | U95 | P |
|---|---|---|---|---|---|---|---|---|
| rs3732378 | 3 | 39307162 | 0.18 | 0.17 | 1.04 | 0.97 | 1.12 | 0.25 |
| rs3732379 | 3 | 39307256 | 0.29 | 0.28 | 1.05 | 0.99 | 1.11 | 0.15 |
| rs41535248 | 3 | 39307962 | 0.01 | 0.01 | 1.08 | 0.84 | 1.39 | 0.54 |

*position in HG19;
Minor Allele Frequency (MAF) in CD cases;
$MAF in non-IBD controls In contrast, antibodies against bacterial and host antigens previously shown to increase in IBD (Prideaux et al., 2012, Inflamm Bowel Dis 18(7): 1340-1355) were not affected by this mutation (Table 2, FIG. 4B).

TABLE 2

Association of missense mutations in CX3CR1 with serological markers in CD patients

| SNP | serology | FA* | FU$ | OR | L95 | U95 | P |
|---|---|---|---|---|---|---|---|
| rs3732378 | anca | 0.181 | 0.174 | 1.13 | 0.77 | 1.64 | 0.535 |
|  | cbir | 0.165 | 0.182 | 0.88 | 0.63 | 1.23 | 0.459 |
|  | i2 | 0.159 | 0.202 | 0.69 | 0.48 | 0.98 | 0.041 |
|  | igg.asca | 0.135 | 0.205 | 0.59 | 0.41 | 0.84 | 3.73E-03 |
| rs3732379 | anca | 0.290 | 0.287 | 1.05 | 0.77 | 1.44 | 0.750 |
|  | cbir | 0.284 | 0.289 | 0.98 | 0.74 | 1.29 | 0.874 |
|  | i2 | 0.277 | 0.307 | 0.83 | 0.62 | 1.12 | 0.218 |
|  | igg.asca | 0.260 | 0.307 | 0.79 | 0.59 | 1.05 | 0.103 |
| rs41535248 | anca | 0.015 | 0.009 | 1.53 | 0.44 | 5.40 | 0.505 |
|  | cbir | 0.006 | 0.015 | 0.42 | 0.11 | 1.62 | 0.208 |
|  | i2 | 0.012 | 0.006 | 2.23 | 0.51 | 9.79 | 0.287 |
|  | igg.asca | 0.017 | 0.007 | 2.60 | 0.75 | 9.05 | 0.133 |

Figure 26:
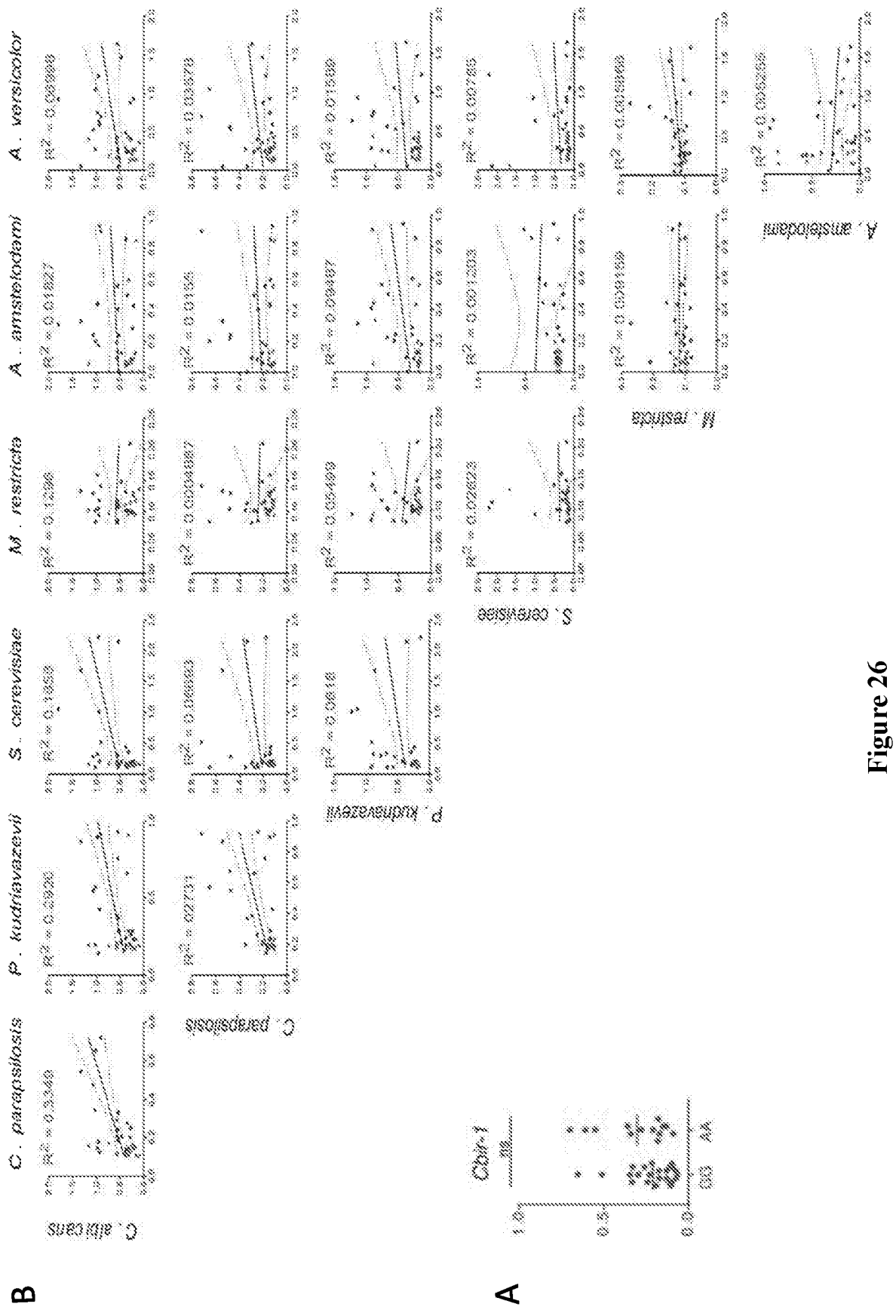
FIG. 26. Human serum IgG responses. (A) IgG responses against cbir. (B) Linear correlation between IgG responses against different fungal species. Values in red represent R2 value from the Pearson correlation coefficient. Weak correlation coefficient suggests lack of serum antibody cross-reactivity between the respective fungi. Red dots: AA patients, blue dots GG patients.
Figure 27:
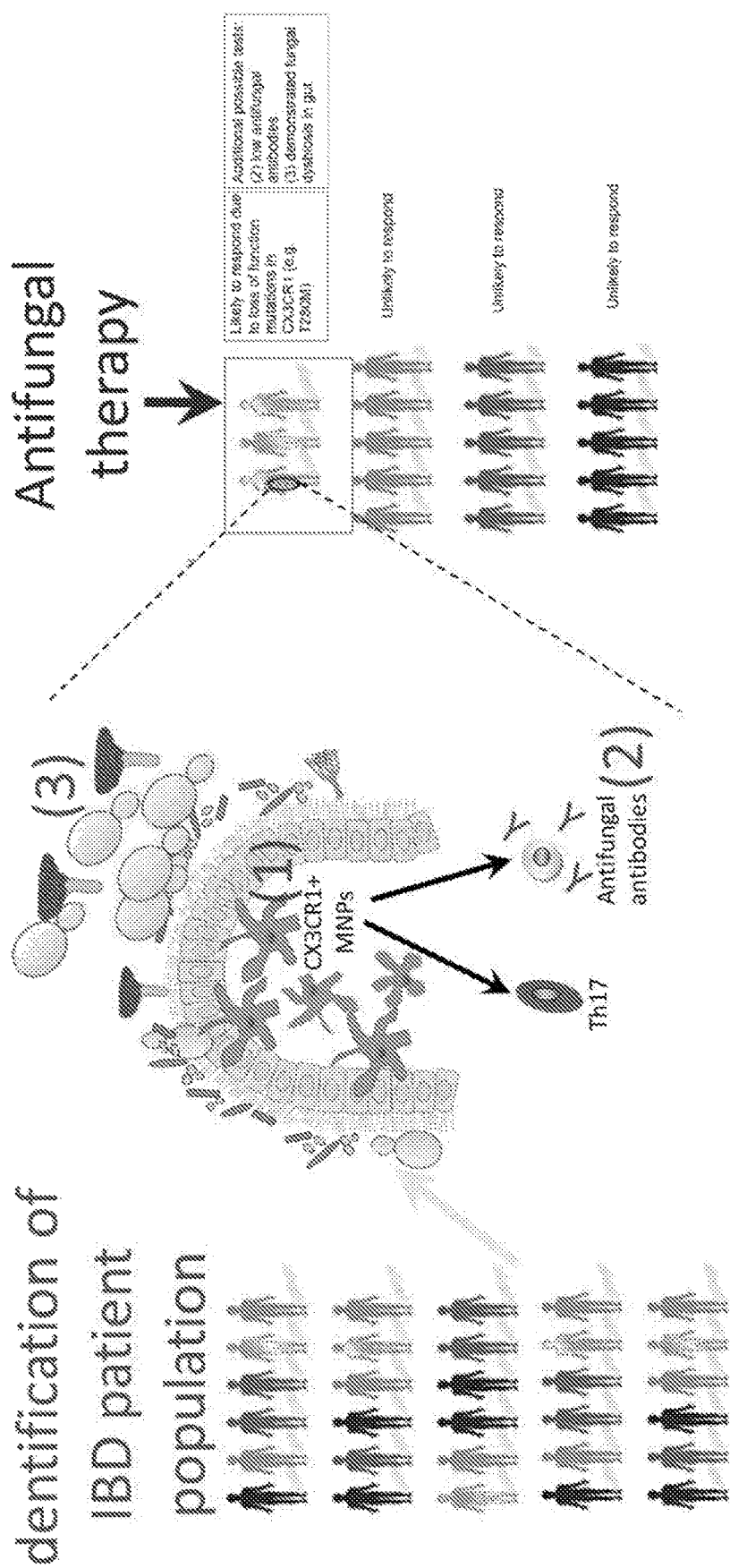
FIG. 27. Schematic of an embodiment of the invention. Among subjects with inflammatory bowel disease, subjects with one or more loss-of-function mutations in CX3CR1 are more likely to benefit from treatment with anti-fungal drugs. They may also be tested for lower levels of antibodies against fungi, and may also be tested for gut mycobiota dysbiosis prior to deciding to administer the antifungal.

*MAF in serology positive CD patients;
$MAF in serology negative CD patients;

Because ASCA antibodies are directed against both *S. cerevisiae* and *C. albicans*, we next assessed whether antifungal antibody responses to common human commensals are also affected by CX3CR1 T280M. Compared to heterozygous individuals, patients homozygous for CX3CR1 T280M were severely impaired in their ability to generate systemic IgG recognizing a variety of gut relevant fungi, while producing normal antibody responses against the bacterial antigen flagellin (FIGS. 4C and D, FIG. 26) consistent with the hypothesis that this mutation in CX3CR1 leads to impaired responses to fungi in the gut.

What is claimed is:

1. A method of treating inflammatory disease in a subject who has been diagnosed with one or more loss-or-function mutations in the CX3CR1 gene comprising administering to the subject a composition comprising a therapeutically effective amount of an anti-fungal agent, wherein the inflammatory disease is an inflammatory bowel disease (IBD).

2. The method of claim 1, wherein the IBD is Crohn's disease.

3. The method of claim 1, wherein the IBD is ulcerative colitis.

4. The method of claim 1, wherein the loss-of-function mutation comprises one or more of the following variants: rs3732378, rs3732379, and/or rs41535248.

5. The method of claim 4, wherein the loss-of-function mutation is the variant rs3732378.

6. The method of claim 1, wherein the anti-fungal agent is selected from the group consisting of voriconazole, fluconazole, terbinafine, caspofungin, natamycin, amphotericine, micafungin, anidulafungin, clotrimazole, isavuconazonium, itraconazole, flucytosine, griseofulvin, efungumab, posaconazole, efmaconazole, tavaborole, luliconazole, terbinafine, auric losene, ketoconazole, 5-FC, APX001, AR-12, ASP2397, F901318, MGCD290, T-2307, E-1224, VT-1161, NDV-3, NDV-3A, SQ-109, MGCD-290, ME-1111, LACTIN-V, and combinations thereof.

7. The method of claim 6, wherein the anti-fungal agent is fluconazole.

8. A method comprising identifying a subject having an inflammatory bowel disease as being suitable for treatment with an anti-fungal agent comprising detecting the presence of a loss-of-function mutation in the CX3CR1 gene, thereby identifying the subject as being suitable for anti-fungal therapy, the method further comprising administering to the subject a composition comprising an anti-fungal agent to thereby treat the inflammatory bowel disease.

9. The method of claim 8, wherein the loss-of-function mutation is a variant rs3732378, rs3732379, and/or rs41535248.

10. The method of claim 9, wherein the loss-of-function mutation is the variant rs3732378.

11. The method of claim 8, wherein the anti-fungal agent is selected from the group consisting of voriconazole, fluconazole, terbinafine, caspofungin, natamycin, amphotericine, micafungin, anidulafungin, clotrimazole, isavuconazonium, itraconazole, flucytosine, griseofulvin, efungumab, posaconazole, efmaconazole, tavaborole, luliconazole, terbinafine, auric losene, ketoconazole, 5-FC, APX001, AR-12, ASP2397, F901318, MGCD290, T-2307, E-1224, VT-1161, NDV-3, NDV-3A, SQ-109, MGCD-290, ME-1111, LACTIN-V, and combinations thereof.

12. The method of claim 11, wherein the anti-fungal agent is fluconazole.

* * * * *

SEQUENCE LISTING

<160> NUMBER OF SEQ ID NOS: 31

<210> SEQ ID NO 1
<211> LENGTH: 51
<212> TYPE: DNA
<213> ORGANISM: Homo sapiens

<400> SEQUENCE: 1
caggcaacaa tggctaaatg caaccatctc agtcacactg agggccagcc t          51

<210> SEQ ID NO 2
<211> LENGTH: 51
<212> TYPE: DNA
<213> ORGANISM: Homo sapiens

<400> SEQUENCE: 2
ttaagcgtct ccaggaaaat cataatgttg tagggtgtcc agaagaggaa a          51

<210> SEQ ID NO 3
<211> LENGTH: 51
<212> TYPE: DNA
<213> ORGANISM: Homo sapiens

<400> SEQUENCE: 3
ctgaatcagt gacagaaaac tttgattacg atgatttggc tgaggcctgt t          51

```
<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cttctggaca ccctacaacg                                              20

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
cctcttctgg acaccctaca aca                                          23

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
gagcttaagy gtctccagga aaatcat                                      27

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
ggccctcagt gtgactgaga c                                            21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ggccctcagt gtgactgaga t                                            21

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
gagaggattc aggcaacaat ggcta                                        25

<210> SEQ ID NO 10
<211> LENGTH: 17
<212> TYPE: PRT
<213> ORGANISM: Gallus gallus
```

-continued

<400> SEQUENCE: 10

Ile Ser Gln Ala Val His Ala Ala His Ala Glu Ile Asn Glu Ala Gly
1               5                   10                  15

Arg

<210> SEQ ID NO 11
<211> LENGTH: 95
<212> TYPE: DNA
<213> ORGANISM: Artificial Sequence
<220> FEATURE:
<223> OTHER INFORMATION: Primer

<400> SEQUENCE: 11
ccggggatcc gaatctttga aaatttctca agctgttcac gctgctcacg ctgaaattaa    60
cgaagctggt agagaagttg ttggtagatc tggcc                              95

<210> SEQ ID NO 12
<211> LENGTH: 94
<212> TYPE: DNA
<213> ORGANISM: Artificial Sequence
<220> FEATURE:
<223> OTHER INFORMATION: Primer

<400> SEQUENCE: 12
gccagatcta ccaacaactt ctctaccagc ttcgttaatt tcagcgtgag cagcgtgaac    60
agcttgagaa attttcaaag attcggatcc ccgg                               94

<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
ggccggatcc gcggccgcat gagtaaagga gaagaacttt tc                      42

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
ggccagatct tttgtatagt tcatccatgc catgtgt                            37

<210> SEQ ID NO 15
<211> LENGTH: 43
<212> TYPE: DNA
<213> ORGANISM: Artificial Sequence
<220> FEATURE:
<223> OTHER INFORMATION: Primer

<400> SEQUENCE: 15
atataaatac tcgagaaaga tgagtaaggg agaagaactt ttc                     43

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
atttagatct ttacatgatg cggccctcct gcag					34

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
cttggtcatt tagaggaagt aa					22

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gctgcgttct tcatcgatgc					20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
agagtttgat cmtggctcag					20

<210> SEQ ID NO 20
<211> LENGTH: 15
<212> TYPE: DNA
<213> ORGANISM: Artificial Sequence
<220> FEATURE:
<223> OTHER INFORMATION: Primer

<400> SEQUENCE: 20
ctgctgccty ccgta					15

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21
tcgtcggcag cgtcagatgt gtataagaga cag					33

<210> SEQ ID NO 22
<211> LENGTH: 34
<212> TYPE: DNA
<213> ORGANISM: Artificial Sequence
<220> FEATURE:
<223> OTHER INFORMATION: Primer

<400> SEQUENCE: 22
gtctcgtggg ctcggagatg tgtataagag acag					34

```
<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
actcctacgg gaggcagcag t                                              21

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
attaccgcgg ctgctggc                                                  18

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
attggagggc aagtctggtg                                                20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ccgatcccta gtcggcatag                                                20

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
cctgtttgag cgtcgttt                                                  18

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
tcctccgctt attgatat                                                  18

<210> SEQ ID NO 29
<211> LENGTH: 22
<212> TYPE: DNA
<213> ORGANISM: Artificial Sequence
<220> FEATURE:
<223> OTHER INFORMATION: Primer
```

```
<400> SEQUENCE: 29
ggaagtaaaa gtcgtaacaa gg                                              22

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
cgttactrrg gcaatccctg ttg                                             23

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31
gcrcggaara cgcttctc                                                   18
```